(12) United States Patent
Clark et al.

(10) Patent No.: US 12,083,285 B2
(45) Date of Patent: *Sep. 10, 2024

(54) AEROSOL SYSTEM AND INTERFACE TO DELIVER CLINICALLY AND ECONOMICALLY FEASIBLE INHALED DOSE WITH NEONATAL CPAP DEVICE

(71) Applicant: Stamford Devices Ltd., Galway (IE)

(72) Inventors: Andrew R. Clark, San Mateo, CA (US); James B. Fink, San Mateo, CA (US)

(73) Assignee: Stamford Devices Ltd., Dangan (IE)

( * ) Notice: Subject to any disclaimer, the term of this patent is extended or adjusted under 35 U.S.C. 154(b) by 918 days.

This patent is subject to a terminal disclaimer.

(21) Appl. No.: 16/883,677

(22) Filed: May 26, 2020

(65) Prior Publication Data

US 2020/0368457 A1 Nov. 26, 2020

Related U.S. Application Data

(60) Provisional application No. 62/852,867, filed on May 24, 2019, provisional application No. 62/

(51) Int. Cl.
*A61M 15/00* (2006.01)
*A61M 16/04* (2006.01)
*A61M 16/06* (2006.01)
*A61M 16/08* (2006.01)
*A61M 39/10* (2006.01)

(52) U.S. Cl.
CPC .... *A61M 16/0465* (2013.01); *A61M 16/0488* (2013.01); *A61M 16/0666* (2013.01); *A61M 16/0816* (2013.01); *A61M 16/0883* (2014.02); *A61M 11/005* (2013.01); *A61M 2039/1077* (2013.01); *A61M 2202/0488* (2013.01); *A61M 2205/0294* (2013.01); *A61M 2205/3379* (2013.01); *A61M 2205/581* (2013.01); *A61M 2205/583* (2013.01); *A61M 2205/8206* (2013.01); *A61M 2230/40* (2013.01); *A61M 2240/00* (2013.01)

(58) Field of Classification Search
CPC ........... A61M 16/0833; A61M 11/001; A61M 11/002; A61M 11/005; A61M 11/02; A61M 15/0085; A61M 2039/1077
See application file for complete search history.

(56) References Cited

U.S. PATENT DOCUMENTS

| | | | |
|---|---|---|---|
| 8,196,573 | B2 | 6/2012 | Fink et al. |
| 8,701,658 | B2 | 4/2014 | Mazela et al. |
| 8,985,100 | B2 | 3/2015 | Minocchieri et al. |
| 9,308,333 | B2 | 4/2016 | Minocchieri et al. |
| 2002/0020412 | A1* | 2/2002 | Gilbert .............. A61M 16/0833 128/203.12 |
| 2004/0244804 | A1* | 12/2004 | Olsen ................ A61M 16/0683 128/207.18 |
| 2005/0217666 | A1* | 10/2005 | Fink ........................ A61P 31/10 128/200.14 |
| 2005/0229926 | A1 | 10/2005 | Fink et al. |
| 2012/0125334 | A1 | 5/2012 | Korneff et al. |
| 2013/0146053 | A1* | 6/2013 | Mazela .............. A61M 16/0858 137/15.01 |
| 2013/0291859 | A1* | 11/2013 | Casey .................. A61M 11/005 128/200.14 |
| 2015/0165146 | A1 | 6/2015 | Bowman et al. |
| 2016/0130715 | A1* | 5/2016 | Xu .......................... C25D 3/48 205/122 |
| 2016/0136368 | A1* | 5/2016 | Spandorfer ....... A61M 16/0883 128/203.14 |
| 2018/0169691 | A1 | 6/2018 | Macloughlin et al. |
| 2018/0221296 | A1* | 8/2018 | Holekamp ............. A61K 9/0014 |
| 2018/0272081 | A1* | 9/2018 | Porter ............... A61M 16/0816 |

FOREIGN PATENT DOCUMENTS

| | | | | |
|---|---|---|---|---|
| JP | 2007-533411 | A | | 11/2007 |
| JP | 2011-515153 | A | | 5/2011 |
| JP | 2011-519642 | A | | 7/2011 |
| WO | WO-2006026237 | A1 | * | 3/2006 .......... A61M 11/003 |
| WO | 2011-038901 | A1 | | 4/2011 |
| WO | WO-2016159784 | A1 | * | 10/2016 ............ A61M 11/04 |
| WO | 2016/198667 | | | 12/2016 |
| WO | WO-2018034574 | A1 | * | 2/2018 ........ A61M 16/0672 |
| WO | 2018/172561 | A1 | | 9/2018 |
| WO | 2018/172562 | A1 | | 9/2018 |

OTHER PUBLICATIONS

International Preliminary Report on Patentability for PCT/US2020/034576 issued Nov. 16, 2021, all pages.
Examination Report for EP 18 714 745.9 dated May 21, 2021, all pages.
Office Action received Oct. 30, 2023 for JP Appln No. 2021-569474, 7 pages.
Office Action received Jan. 4, 2024 for CN Appln No. 202080038393.9, 10 pages.

* cited by examiner

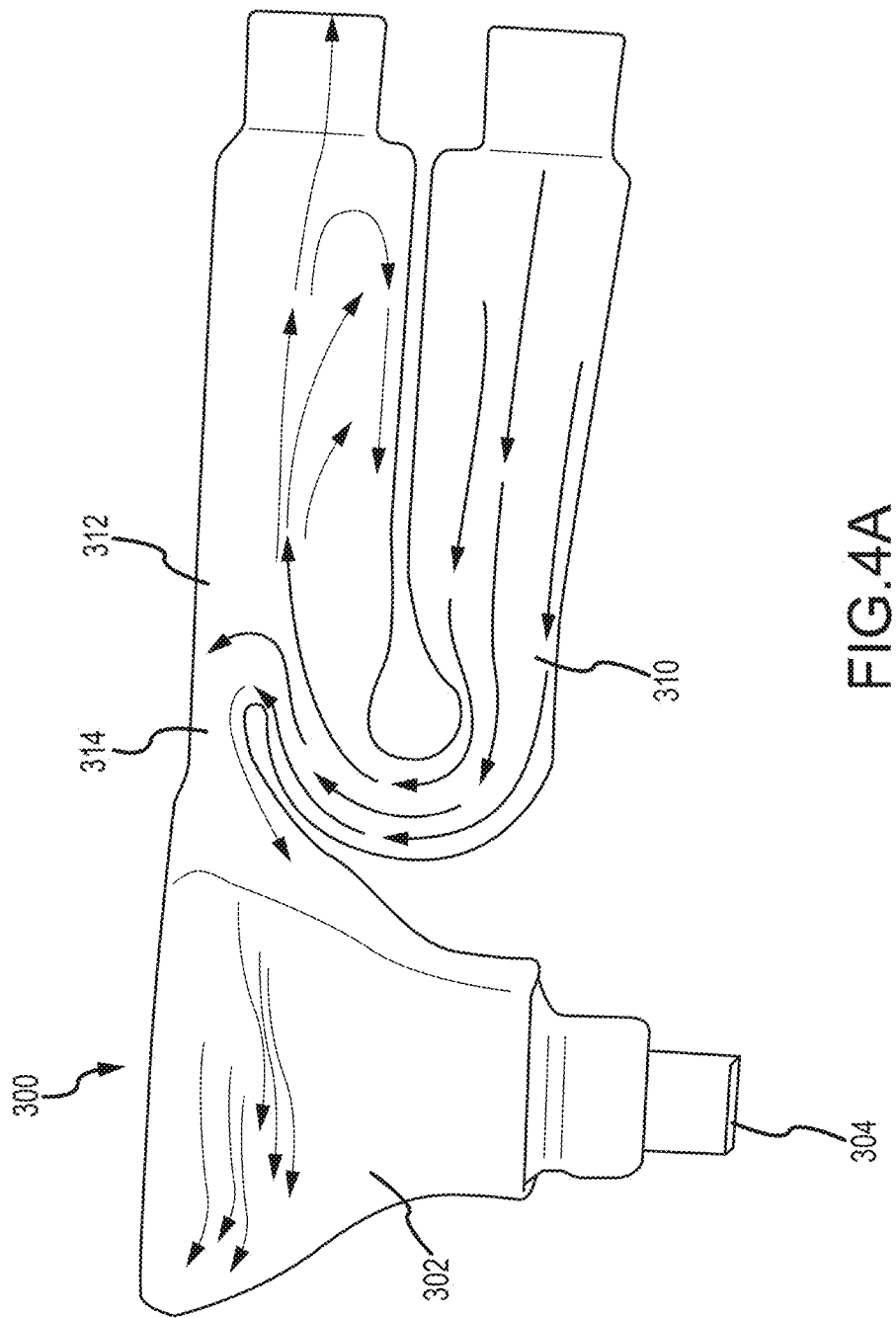

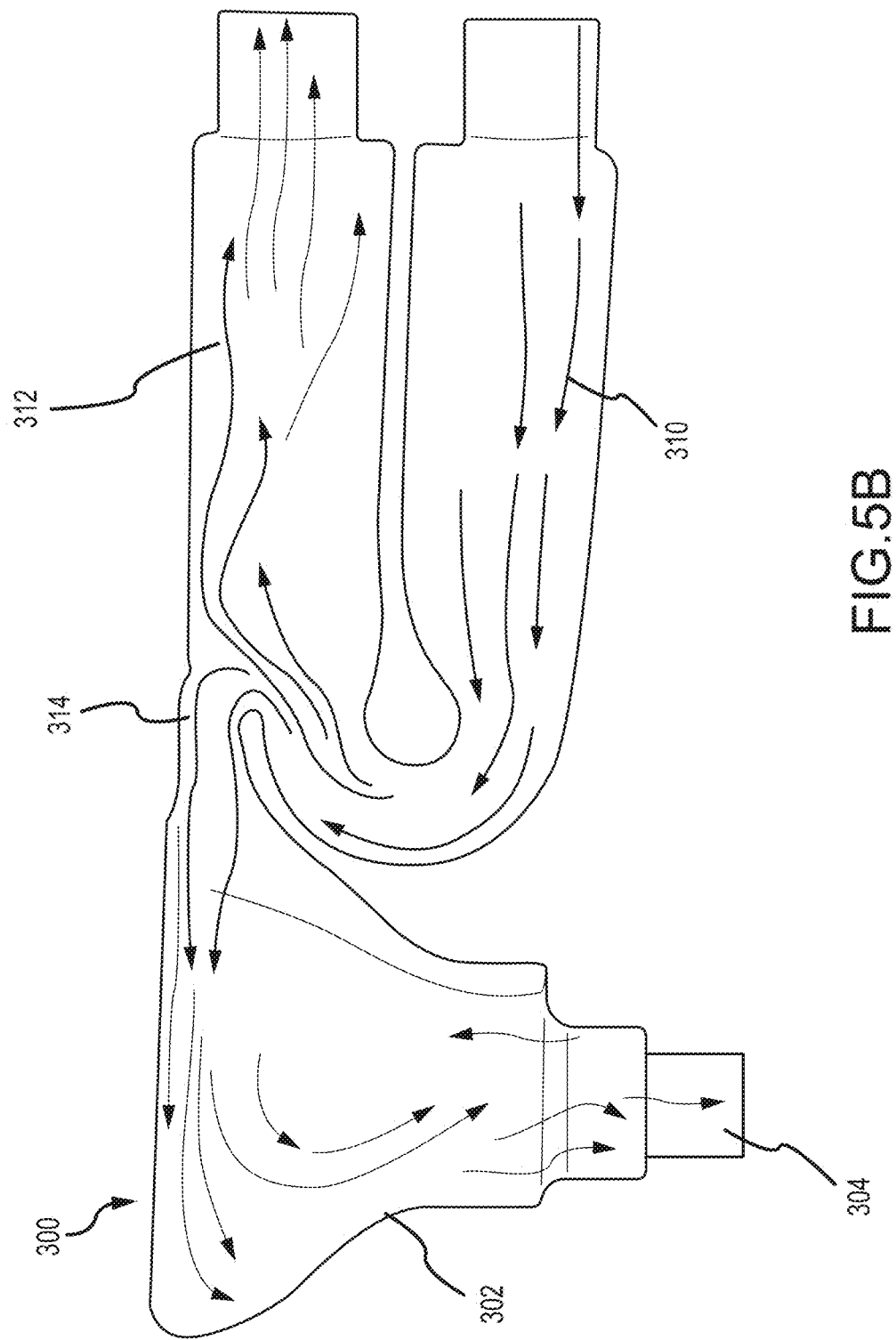

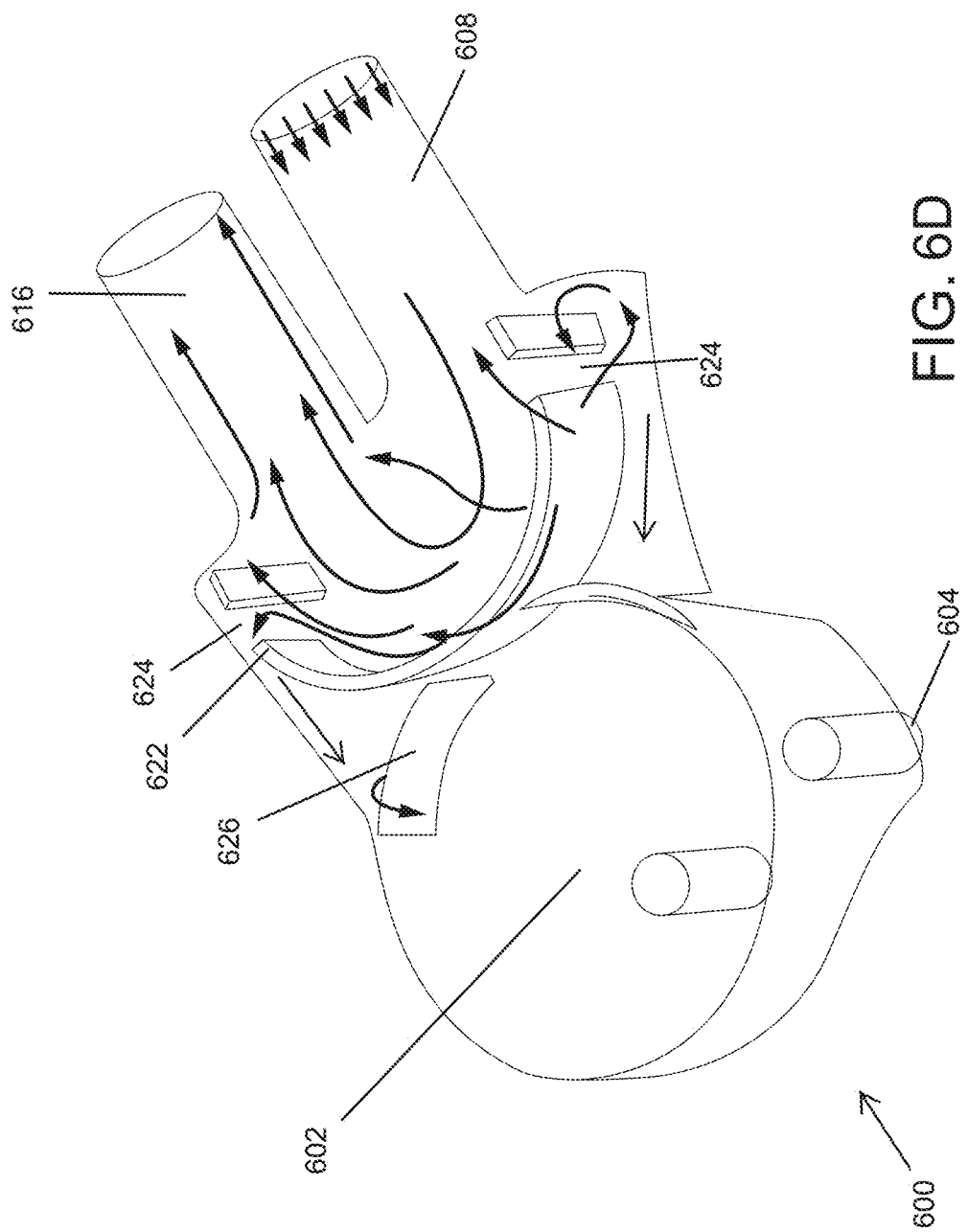

FIG.14B

2) PATIENT INFORMATION
Follow onscreen instructions to enter the following information:
A) Patient ID (use 123-456-98)

B) Patient weight (e.g. 580g)

C) Select Dose 'A' or 'B'

D) Confirm Details

Confirm Dosing Details
Patient ID: 123-456-98
Weight (g): 580
Selected Dose(mg/kg): 108.0(A)
Total Dose (ml): 1.4
Total Dose (mg): 62.6
No of vials: 1

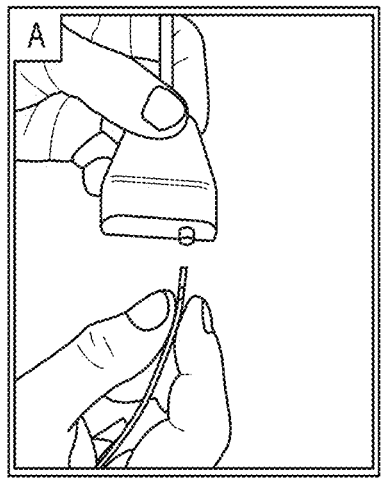
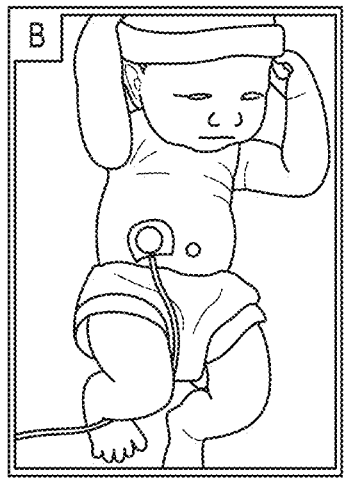
FIG. 14D

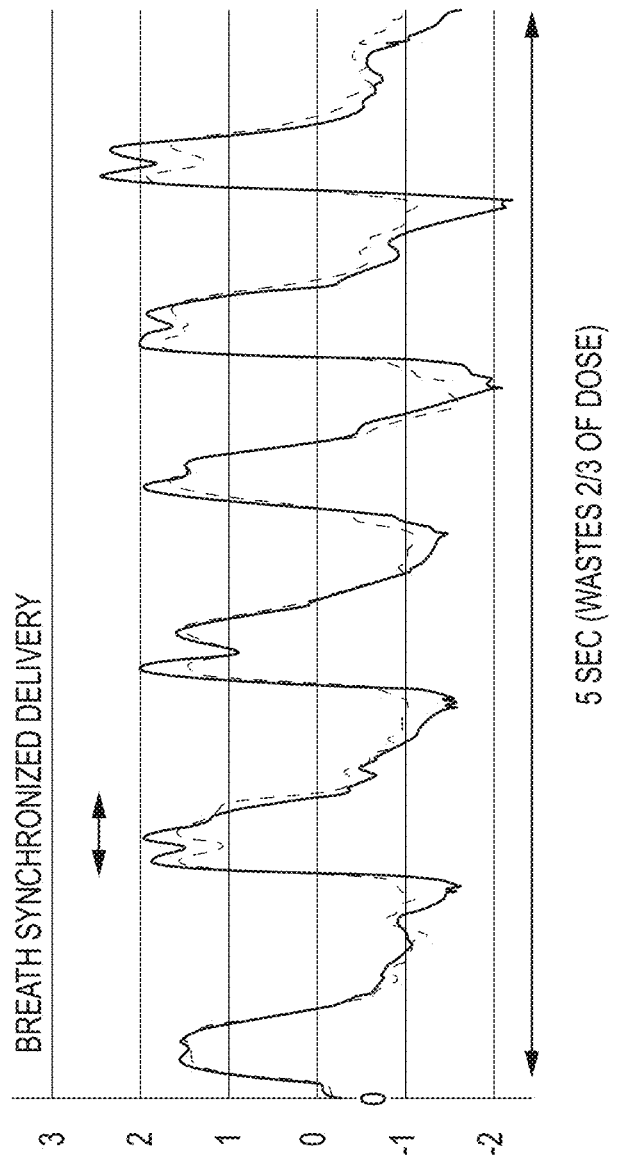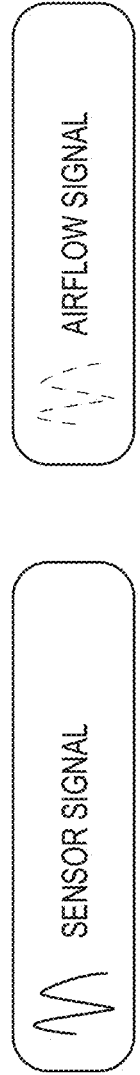
FIG. 24

AEROSOL SYSTEM AND INTERFACE TO DELIVER CLINICALLY AND ECONOMICALLY FEASIBLE INHALED DOSE WITH NEONATAL CPAP DEVICE

CROSS REFERENCE TO RELATED APPLICATIONS

This application claims priority to U.S. Provisional Application No. 62/852,862, filed on May 24, 2019, entitled Design Of Aerosol System And Interface To Deliver Clinically And Economically Feasible Inhaled Dose With Neonatal CPAP Device and U.S. Provisional Application No. 62/852,867, filed on May 24, 2019, entitled Design Of Aerosol Chamber And Interface To Optimize Inhaled Dose With Neonatal CPAP Device, the entire contents of which are hereby incorporated by reference.

This application is related to U.S. application Ser. No. 15/933,205, filed on Mar. 22, 2018, entitled Aerosol Delivery Device, U.S. application Ser. No. 15/933,217, filed on Mar. 22, 2018, entitled Retrofit Aerosol Delivery System and Method, U.S. application Ser. No. 15/933,219, filed on Mar. 22, 2018, entitled Aerosol Delivery System and Method, U.S. Application No. 62/475,618, filed Mar. 23, 2017, entitled Retrofit Aerosol Delivery System and Method, U.S. Application No. 62/475,635, filed Mar. 23, 2017, entitled Aerosol Delivery Device, and U.S. Application No. 62/475,603, filed Mar. 23, 2017, entitled Aerosol Delivery System and Method, the entire contents of which are incorporated by reference herein.

BACKGROUND

Surfactant delivery to infants, especially preterm infants, can be invasive and is often associated with acute side effects. As a result, it is desirable to provide non-invasive delivery of surfactants. However, it is difficult to effectively and efficiently deliver surfactant using conventional non-invasive techniques. For example, conventional techniques often rely on constant delivery of aerosolized medicament, which is very inefficient as medicament is aerosolized even between breaths of a patient. Additionally, conventional techniques typically involve aerosolized particles that are larger (typically about 4-7 µm mass median aerodynamic diameter (MMAD)) than desirable for pulmonary delivery, as it is difficult to produce small aerosolized particles of surfactant at a sufficiently high output rate to make pulmonary delivery feasible. Embodiments of the present invention solve these and other problems.

SUMMARY

Embodiments of the invention provide aerosolization systems and methods for delivering medicament to infants, and in particular, preterm infants. Embodiments provide techniques to effectively and efficiently deliver medicament to an infant's nares. Embodiments also provide sufficiently fine aerosol droplets of medicament to penetrate into the lungs. Embodiments provide significantly higher medicament delivery efficiencies than conventional non-invasive techniques.

In one embodiment, a method of delivering aerosolized medicament to an infant is provided. The method may include interfacing an aerosolization device with an airway of an infant and aerosolizing, using the aerosolization device, a volume of medicament into particles having a mass mean aerodynamic diameter (MMAD) of less than about 3 µm at a rate of at least 0.1 ml/min. The medicament may be aerosolized within about 2 to 8 cm from a patient interface. The method may also include delivering the aerosolized medicament to the infant's airway.

In another embodiment, an aerosolization system is provided. The aerosolization system may include an aerosolization device having an aerosol generator positioned at a first end of an aerosol chamber. The aerosol generator may include a reservoir that is configured to receive a volume of liquid surfactant for aerosolization by the aerosol generator. The aerosol generator may be configured to aerosolize the volume of medicament into particles having a mass mean aerodynamic diameter (MMAD) of less than about 3 µm at a rate of at least 0.1 ml/min. The aerosolization device may include a patient interface that is positioned within about 2 cm and 8 cm from the aerosol generator and a respiratory adaptor that is configured to couple the aerosolization system with a respiratory system that may have an inspiratory limb and an expiratory limb. The respiratory adaptor may include at least one baffle that may define at least one airway that is in fluid communication with the aerosol chamber. The at least one baffle may be configured to divert a first portion of airflow from the inspiratory limb to the expiratory limb and to divert a second portion of airflow into the aerosol chamber via the at least one airway. The second portion of airflow may be respiratory flow and may be smaller than the first portion. The aerosol chamber may be configured to mix the respiratory flow with aerosolized medicament from the aerosolization device. In some embodiments, the aerosolization system may also include at least one breath sensor that is configured to detect an inhalation of the infant and a controller that is configured to synchronize the aerosolization of the volume of surfactant with the detected inhalation.

In one embodiment, an aerosolization system is provided. The system may include a respiration system comprising an inspiratory limb and an expiratory limb. The system may also include an aerosolization device that includes an aerosol chamber having a first end and a second end and an aerosol generator positioned at the first end of the aerosol chamber. The aerosol generator may include a reservoir that is configured to receive a volume of liquid medicament for aerosolization by the aerosol generator. The aerosol generator may be configured to aerosolize the volume of medicament into particles having a mass mean aerodynamic diameter (MMAD) of less than about 3 µm at a rate of at least 0.1 ml/min. The aerosolization device may include a patient interface that is positioned proximate the second end of the aerosol chamber and a respiratory adaptor that is configured to couple the aerosolization system with the respiration system. The system may also include at least one breath sensor that is configured to detect an inhalation of a patient and a controller that is configured to actuate the aerosol generator to aerosolize the volume of medicament in synchronization with the detected inhalation.

In some embodiments, the patient interface may be positioned between about 1 cm and 8 cm from the aerosol generator. In some embodiments, the respiratory adaptor may include a diversion mechanism that is configured to divert a portion of airflow from the respiration system into the aerosol chamber via at least one airway. The aerosol chamber may be configured to mix the portion of the airflow with aerosolized medicament from the aerosol generator. In some embodiments, the portion of airflow may be respiratory flow and is less than an amount of air that continues to an expiratory limb of the respiration system. In some embodiments, the diversion mechanism may include at least one baffle that defines the at least one airway. The at least one baffle may be configured to divert the portion of airflow into the aerosol chamber via the at least one airway and to divert an additional portion of airflow from the inspiratory limb to the expiratory limb. In some embodiments, the at least one baffle comprises a first baffle that defines a first airway and a second baffle that defines a second airway. In some embodiments, the first airway may be provided at a lateral end of the first baffle, the second airway is provided beyond a distal edge of the second baffle, and the lateral end and the distal edge may extend in different directions such that the respiratory flow moves in multiple directions to pass the first baffle and the second baffle.

In some embodiments, the system may further include a conduit that is configured to deliver the volume of liquid medicament from the reservoir to the aerosol generator. In some embodiments, a distalmost tip of the conduit has a diameter and the distalmost tip of the conduit is positioned at a distance from the mesh that is less than or equal to the diameter. In some embodiments, synchronization of the aerosolization of the volume of medicament may include aerosolizing a portion of the volume of medicament within at least a portion of a first 50%-80% of each of a successive number of inhalations such that chase air is provided within at least a portion of a final 20% of each of the successive number of inhalations. In some embodiments, the at least breath sensor may include a respiration sensor capsule interfaced with the patient's abdomen. In some embodiments, the controller is removable from the aerosolization device. In some embodiments, the aerosolization device may be configured to aerosolize and deliver aerosolized particles of the medicament while the patient interface is oriented in each of a downward position, a side-facing position, and an upward position. In some embodiments, the system further includes a feed line that is configured to supply the volume of the medicament from a source to the reservoir. In some embodiments, the patient interface comprises nasal prongs or a nasal mask. In some embodiments, the medicament comprises a surfactant.

In another embodiment, a method of delivering aerosolized medicament to an infant is provided. The method may include detecting an inhalation of an infant using one or more breath sensors and aerosolizing, using an aerosolization device, a volume of medicament into particles having a mass mean aerodynamic diameter (MMAD) of less than about 3 μm at a rate of at least 0.1 ml/min based on the detected inhalation. The medicament may be aerosolized within about 1 to 8 cm from a patient interface.

In some embodiments, aerosolizing the volume of the medicament may include delivering the volume of the medicament from a reservoir to a mesh of the aerosolization device and vibrating the mesh to aerosolize the volume of the medicament. In some embodiments, the volume of the medicament may be delivered from the reservoir to the mesh via a conduit having a distalmost tip with a diameter. The distalmost tip of the conduit may be positioned at a distance from the mesh is less than or equal to the diameter. In some embodiments, aerosolizing the volume of the medicament may include aerosolizing a portion of the volume of medicaments within at least a portion of a first 80% of each of a successive number of inhalations such that chase air is provided within at least a portion of a final 20% of each of the successive number of inhalations. In some embodiments, the one or more breath sensors may include a respiration sensor capsule interfaced with the patient's abdomen. In some embodiments, the method further includes delivering the aerosolized medicament to the infant's airway via a patient interface. In some embodiments, the patient interface includes nasal prongs or a nasal mask.

In some embodiments, the method may also include coupling the aerosolization device with a respiration system and diverting a portion of airflow from the respiration system into a chamber of the aerosolization device via at least one airway. The chamber may be configured to mix the portion of the airflow with aerosolized medicament. In some embodiments, the portion of airflow may be respiratory flow and is less than an amount of air that continues to an expiratory limb of the respiration system. In some embodiments, the portion of airflow may be diverted using at least one baffle that defines the at least one airway. The at least one baffle may be configured to divert the portion of airflow into the aerosol chamber via the at least one airway and to divert an additional portion of airflow from an inspiratory limb to an expiratory limb. In some embodiments, the at least one baffle may include a first baffle that defines a first airway and a second baffle that defines a second airway. In some embodiments, the first airway is provided at a lateral end of the first baffle, the second airway is provided beyond a distal edge of the second baffle, and the lateral end and the distal edge extend in different directions such that the airflow moves in multiple directions to pass the first baffle and the second baffle.

In another embodiment, a method of initializing an aerosolization system is provided. The method may include connecting an aerosolization device with a controller, a respiration sensor, a medication source, and a respiration system, inputting a user's access credentials into the controller, and inputting information associated with a patient and dose information into the controller. The method may also include coupling the respiration sensor with a patient, priming the aerosolization device, and interfacing a patient interface with the patient's airways.

In some embodiments, the method may further include performing a start-up sequence that cycles through a plurality of audio alarms, visual alarms, or both audio and video alarms. In some embodiments, the access credentials include one or more of a user identifier, a password, a possession-based credential, and a biometric credential. In some embodiments, the respiration sensor may be adhered to the patient's abdomen. In some embodiments, the method also includes confirming a detection of breath after coupling the respiration sensor with the patient. In some embodiments, the medication source includes a vented vial access device (VVAD) that is coupled with a fluid supply line. In some embodiments, connecting the aerosolization device with the controller, the respiration sensor, the medication source, and the respiration system includes coupling a fluid supply line between the medication source and the aerosolization device. In some embodiments, priming the aerosolization device may include aerosolizing a portion of medicament prior to interfacing the patient interface with the patient's airways. In some embodiments, the method may further include coupling the patient interface to the aerosolization device. In some embodiments, the patient interface is secured to patient via one or both of at least one strap and a foam pad that is configured to rest against the patient's head. In some embodiments, the method may include delivering a dose of aerosolized medicament to the patient via the patient interface. In some embodiments, the method may also include confirming that a timing of the delivered dose is in sync with a detected inhalation.

BRIEF DESCRIPTION OF THE DRAWINGS

FIG. 4A illustrates flow patterns through the aerosolization device of FIG. 3.

FIG. 5B illustrates flow patterns from a low flow respiration system through the aerosolization device of FIG. 3.

FIG. 6D illustrates flow patterns through the aerosolization device of FIG. 6.

FIGS. 14A-14I illustrate a process for using the aerosolization system of FIGS. 9-13.

FIG. 24 is a graph illustrating the effectiveness of inhalation detection using flow sensors and respiration sensor capsules.

DETAILED DESCRIPTION

Figure 1:
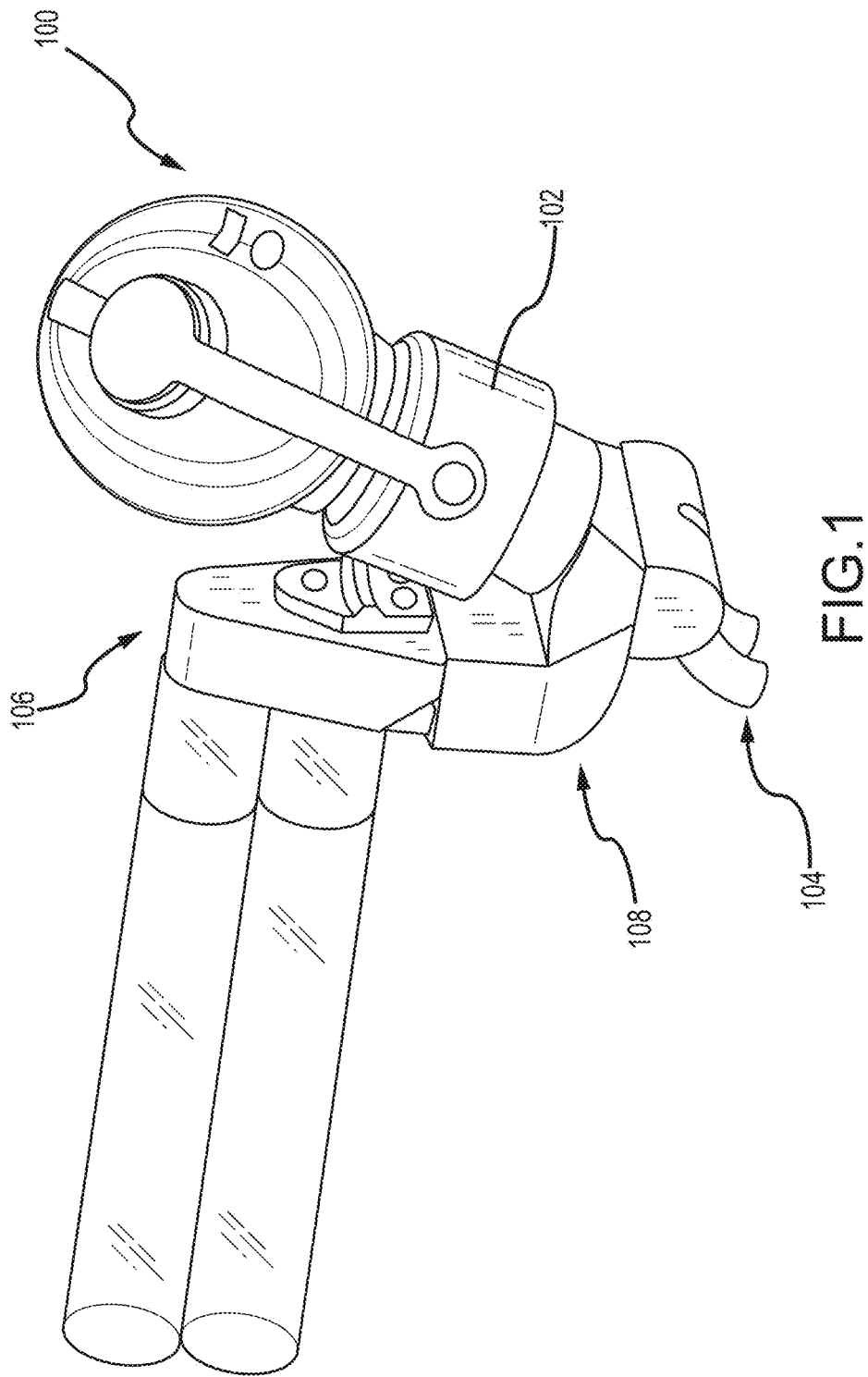
FIG. 1 is an isometric view of an aerosolization device according to embodiments.

The ensuing description provides embodiment(s) only, and is not intended to limit the scope, applicability or configuration of the disclosure. Rather, the ensuing description of the embodiment(s) will provide those skilled in the art with an enabling description for implementing an embodiment. It is understood that various changes may be made in the function and arrangement of elements without departing from the spirit and scope of this disclosure.

Embodiments of the invention provide aerosolization systems and methods in which aerosolized medicament and respiratory gases are mixed within an aerosolization chamber that is isolated from a direct flow of respiration system such that a small portion of the respiratory gases enter the aerosolization chamber while most of the respiratory flow bypasses the chamber and passes through an expiratory limb of a respiration system. Such design considerations ensure that drug delivery rates are consistent, regardless of flow rates from a respiration system. Additionally, embodiments of the invention provide retrofit aerosolization solutions that can be coupled with existing respiration systems to adapt the existing system to be able to deliver a reliable dose of aerosolized medicament to a patient's airways. Additionally, the aerosolization systems provided herein may include one or more breath sensors, such as one or more flow sensors, (e.g., electrical flow sensors), radar sensors (e.g., ultra-wideband (UWB) radar sensors for measuring chest displacement), $CO_2$ sensors, high-speed temperature sensors, acoustic sensors, impedance plethysmography sensors, respiratory inductance plethysmography sensors, pressure sensors, and the like that enable a controller to predict a patient's inhalations, allowing for the aerosolization of medicament during, or immediately prior to, the patient's inhalations.

Embodiments of the invention provide aerosolization systems that isolate aerosolized medicament from a primary respiratory gas flow to avoid disruption and dilution of aerosol produced during inspiratory phase. Such isolation may be achieved using baffles and/or other barriers that are designed to redirect primary flow from inlet to outlet without flushing gas through the patient interface.

Embodiments of the invention also generate and deliver surfactant aerosol only during the inspiratory cycle (inhalation). Commonly used devices administer aerosol continuously. However, the infant can only inhale aerosol during inspiration, so during exhalation (up to two thirds of the breathing cycle) aerosol bypasses the airway and is lost and wasted. By limiting aerosol generation to occur only during inhalation and delivering the aerosol proximal to the nares, it can be assured that the highest percentage of surfactant is available for deposition in the lungs.

Embodiments of the invention also produce the aerosol proximate to a patient interface to help increase the amount of aerosol that is delivered to the patient. Conventional nebulizers are placed somewhere in the inspiratory tubing of the ventilator or nCPAP circuit, where aerosol is generated within a continuous flow of gas. This greatly dilutes the aerosol being delivered and much is lost in the continuous gas flow, which generally exceeds subjects inspiratory flow. In contrast, aerosolization devices of the present invention generate aerosol directly at the patient interface (such as nasal prongs) and diverts substantive gas flow from the nCPAP circuit away from the aerosol plume to markedly reduce aerosol loss in the continuous gas flow of the circuit. Embodiments also use an aerosol generator that emits aerosol surfactant at rates of 0.3 mL/min or greater with undiluted surfactant, which is faster than previously reported with other mesh nebulizers and reduces the time of administration. While discussed primarily in relation to the delivery of surfactant, it will be appreciated that other forms of medicament may be utilized with the aerosolization systems of the present invention to deliver aerosolized medicament to the lungs of a patient.

In some embodiments, the aerosolization systems described herein may include a reusable device controller and disposable single-patient single-use aerosolization device that includes a drug delivery circuit and/or breath sensor. Such aerosolization devices serve as stand-alone drug delivery devices that integrate with a variety of ventilation devices (such as CPAP devices), and in some embodiments is not designed to be connected to the hospital network or the Internet. For example, the controller may be a multi-patient, reusable component with flat panel touchscreen display, electronics, and software. The controller may have three core functions: to detect inspiration via a breath sensor (which may be designed for single patient use) that may be attached to a patient's abdomen, to advance suspension to the aerosolization device via an integrated feed mechanism, and to generate aerosol during inspiration at the nCPAP interface. These functions may occur in synchrony with the infant's inspiratory cycle. The flat panel touchscreen utilizes a graphical user interface (GUI) to allow the user to set and monitor delivery parameters, alarms, and system diagnostics. Visual and audible alarms may be integrated into the controller. A pod may be used to communicate the signal from the breath sensor to the controller, and communicate a signal to synchronize aerosol generation with the detected breaths. A reservoir from which the drug product is dispensed may be a drug vial in which medicament is provided.

In some embodiments, the disposable single-patient single-use aerosolization device includes a Vented Vial Access Device (VVAD) that facilitates access to the drug reservoir and is provided to the user in an individual package and a drug feed tubing that includes a luer connector (to VVAD) and tubing conveying drug suspension from the luer to the aerosol generator of the aerosolization device. The aerosolization device may also include an aerosol generator that may use a custom photo defined aperture plate (PDAP) vibrating mesh, which is unique in its ability to provide small droplet sizes and higher output rates. This is due to the PDAP mesh's innovative architecture, which provides up to 20-fold more apertures with smaller diameters than found in conventional meshes. The aerosol generator is designed to dispense aerosol proximal to the infant's airway and connect to conventional nCPAP systems.

The reusable controller is equipped with a built-in touch screen with processors that monitors delivery parameters, alarms (visual and audible) and system diagnostics. The controller and Pod work in concert to detect inspiration via a breath sensor attached on one end to the infant's abdomen and on the other end plugged into the pod. The controller activates the drug feed mechanism, which drives drug delivery to the nebulizer to breath-synchronize the aerosol generation to the infant's inspiratory cycle.

Lyophilized surfactant is reconstituted in its original glass vial to produce a saline/surfactant suspension. The vial is connected to the drug delivery circuit that includes drug feed tubing through a vented vial access device that punctures the vial septum allowing air to vent into the vial allowing suspension to empty in a consistent manner. The integral volumetric drug feed mechanism advances the surfactant suspension through the drug feed tubing and delivers it to the nebulizer (proprietary vibrating mesh) which is integrated into the drug delivery circuit interface. The interface uses nasal prongs. The interface is attached to the infant's clinical nCPAP circuit, and placed on the infant, replacing prior interface. Aerosol is then delivered in synchrony with the infant's inspiration triggered by the breath sensor.

While discussed largely in the context of surfactant, it will be appreciated that the methods and devices of the present disclosure may be used with any liquid medicament. For example, medicaments such as, but not limited to, bronchodilators, anti-infectives, anti-virals, anti-inflammatories mucokinetics, siRNAs, PFOB, and the like may be utilized in accordance with the present disclosure.

Turning to FIG. 1, one embodiment of an aerosolization system is provided. Here, an aerosolization device 100 is positioned on a first side of an aerosol chamber 102 with a patient interface 104 being positioned on an opposite, second side of the aerosolization chamber 102. The aerosolization device 100 may be a nebulizer or any other device that is configured to aerosolize a dose of liquid medicament. Such devices are described in U.S. Pat. Nos. 5,758,637, 6,235,177, U.S. Patent Publication No. 2015/0336115, and U.S. Patent Publication No. 2016/0130715, the entire contents of which are incorporated by reference herein. The aerosolization device 100 may include a reservoir that is configured to receive and/or house a quantity of liquid medicament to be aerosolized. In some embodiments, the reservoir may be a "virtual reservoir" in the form of a conduit that couples and extends between a fluid feed line and a mesh of the aerosolization device 100. For example, the conduit may be sized to only house between about 10-15 mcl that may collect within the conduit between aerosolizations. A primary reservoir may be in the form of a vial containing the medicament, which, via a feed mechanism and feedline, may provide the medicament to the mesh on a breath to breath basis via the conduit or virtual reservoir. In some embodiments, the patient interface may include nasal prongs, endotracheal tubes, nasal cannula/masks, tracheostomy tubes, and the like.

The system includes a respiratory adaptor 106 that is configured to interface with an artificial respiration system, such as a ventilator, humidifier, continuous positive airway pressure (CPAP) machine, nCPAP system, and/or combinations thereof. For example, the respiratory adaptor 106 may include an inlet 108, such as an inlet baffle, that is configured to couple with an inspiratory limb of a respiration system. For example, the inlet 108 may be an inlet baffle that is configured to couple with a Flexitrunk™ Midline Interface produced by Fisher & Paykel Healthcare and to direct respiratory flow into the aerosolization chamber 102. The inlet 108 may be coupled with the aerosol chamber 102, such as via a fluid pathway 110. In some embodiments, the inlet 108 is designed to redirect gas from the respiration system to the aerosolization chamber, without increasing resistance or work of breathing for the patient. This may be done by providing a fluid pathway 110 having a cross-sectional area that is about 80% or greater relative to an internal cross-sectional diameter of the patient interface 104.

Figure 1A:
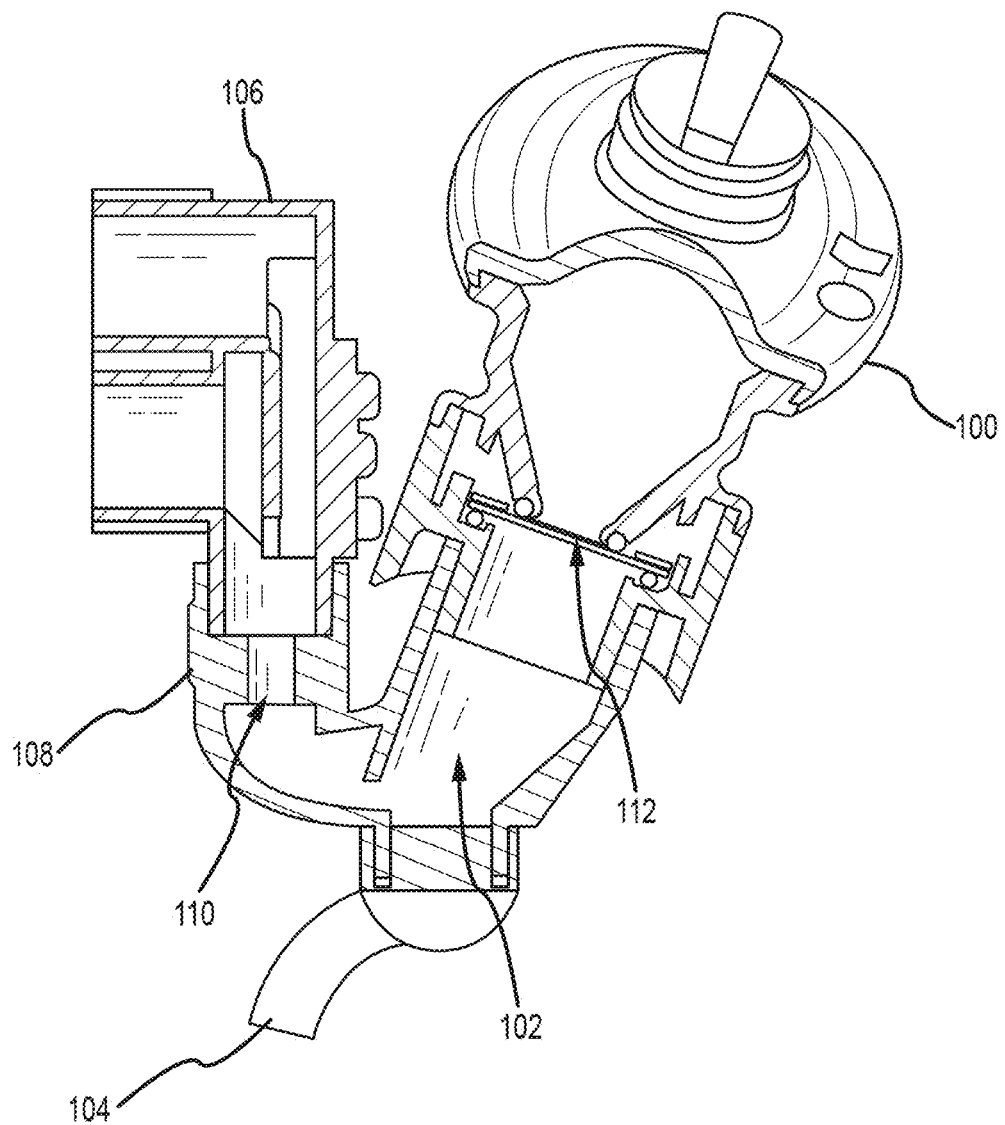
FIG. 1A is a cross-sectional view of the aerosolization device of FIG. 1.

FIG. 1A shows a cross-sectional view of the aerosolization system of FIG. 1. Here, an aerosol generator 112 of the aerosolization device 100 is shown positioned at the first end of the aerosol chamber 102 such that any medicament that is aerosolized by the an aerosol generator 112 is introduced into the aerosolization chamber 102. The aerosol generator 112 may include a mesh that is configured to generate aerosol particles. Conventional aerosol devices typically produce aerosol with mean droplet diameters in the 4 to 5 micron range. However, the aerosol droplet size requirement to deliver drug through the small airways of a premature infant's respiratory tract starting at the nares is generally less 3 microns in diameter. Aerosol droplets larger than this size are susceptible to either deposition in the nares and delivery tubing. If the droplets are much smaller than 1 micron the droplets may not deposit in the lungs and could be exhaled. This reduces the dose delivery efficiency to the lungs. Embodiments of the present invention utilize a mesh hole size that is designed to produce droplets with median diameters of between 2 and 3 microns. For example, in some embodiments, the aerosol generator 112 may include a Photo-defined aperture plate (PDAP) mesh that is configured to generate small aerosol particle sizes, such as below 3 μm. Such meshes are disclosed in U.S. Patent Publication No. 2016/0130715 which was previously incorporated by reference. Placement of the aerosol generator 112 proximal to the patient interface 104 allows aerosolized medicament emitted during inspiratory cycle to preferentially be inhaled with minimal disruption of continuous or bias flow passing through the respiration system circuit. Here, aerosol chamber 102 is shown with the first end being smaller than the second end. The inlet 108 is formed of a baffle that is designed to draw a portion of the respiratory flow from an inspiratory limb of a respiration system into the aerosol chamber 102 at a position near the first end via fluid pathway 110. The fluid pathway 110 is fluidly coupled with the inspiratory limb such that the fluid pathway 110 has an angle of no more than 90 degrees relative to the respiratory flow through the limb and/or an upstream side of the inspiratory limb at the junction between the limb and the inlet 108. Such positioning helps to isolate the aerosolization chamber from direct respiratory flow. For example, respiratory flow is introduced into the aerosol chamber 102 intermittently, occurring only during inhalations of the patient.

Figure 2:
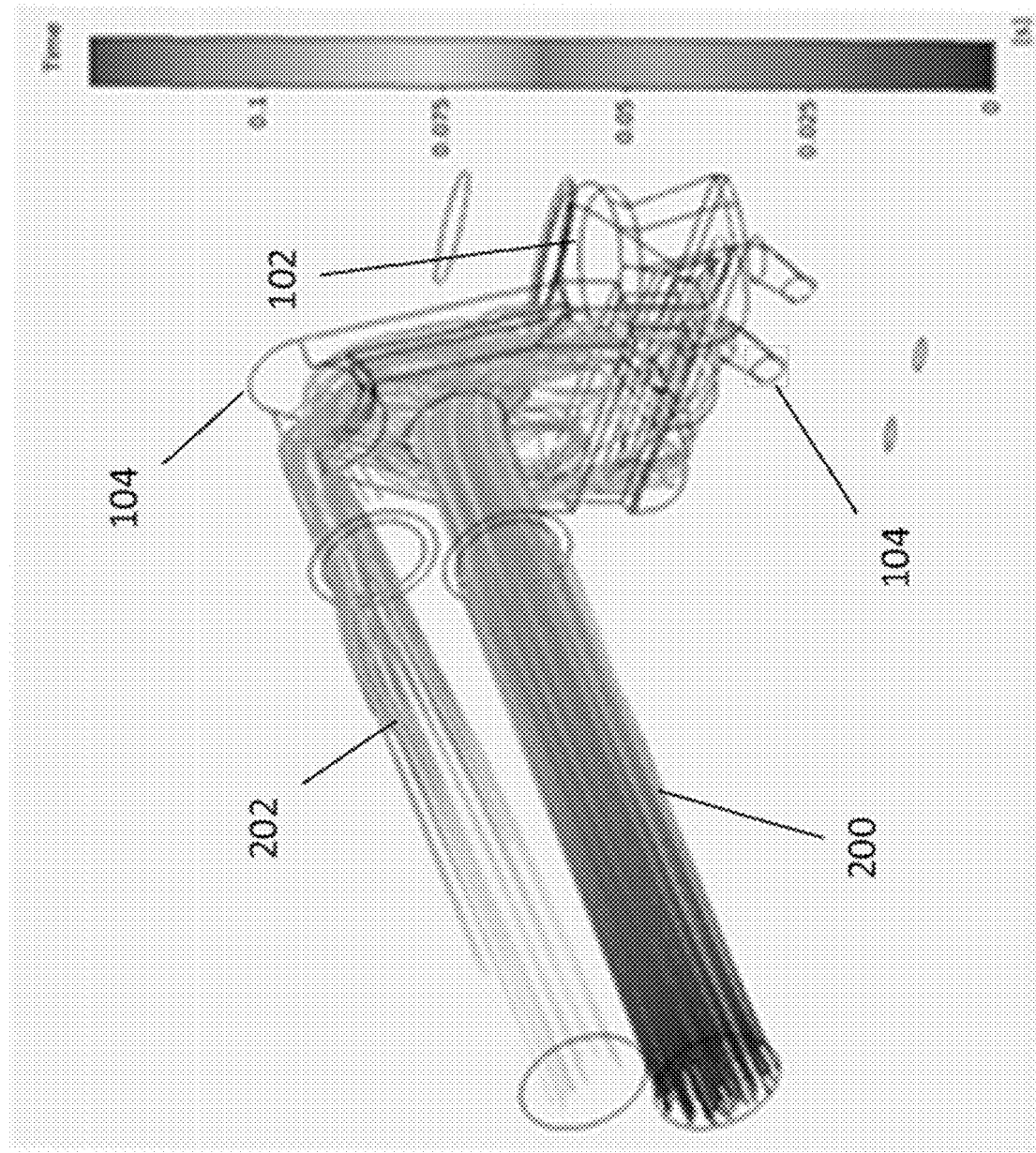
FIG. 2 illustrates flow patterns through the aerosolization device of FIG. 1.

Flow patterns through the aerosolization system are illustrated in FIG. 2, which shows an inspiratory limb 200 of a respiration system supplying respiratory airflow. A portion of this respiratory airflow may be drawn into the inlet 108 and introduced into the aerosol chamber 102 and patient interface 104 via the fluid pathway 110. For example, as the patient inhales, the inhalation creates a vacuum within the aerosolization chamber which draws in a volume of respiratory airflow through the fluid pathway 110. Excess respiratory airflow and/or exhaled gases may be expelled through an expiratory limb 202 of the respiration system.

The aerosolization system of FIGS. 1, 1A, and 2 provides higher and more consistent inhaled dose across a range of gas flows used with various nCPAP systems than conventional aerosolization systems. For example, the aerosolization systems described herein increase the inhaled dose with higher flow nCPAP systems (>6 L/min) from about 6% (as exhibited in conventional systems) to between about 40-50%, and reduced variability from low flow systems (0.5 L/min) which also deliver inhaled doses of between about 40-50%.

Figure 3:
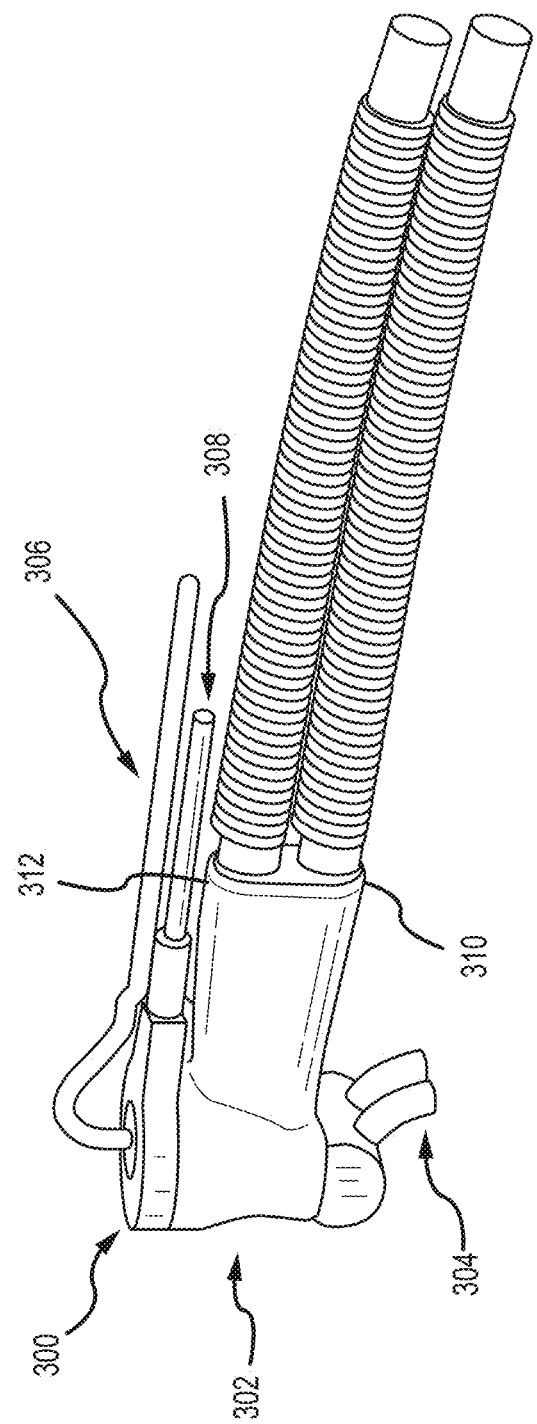
FIG. 3 is an isometric view of an aerosolization device according to embodiments.

FIG. 3 depicts another embodiment of an aerosolization device for providing consistent doses of aerosolized medicament to patients. The aerosolization device may include an aerosol generator 300 positioned at a first end of an aerosol chamber 302, with a patient interface 304 positioned at an opposite, second end of the aerosol chamber 302. The aerosol generator 300 may be a nebulizer having a vibratable mesh that is selectively vibratable using a piezoelectric actuator. In some embodiments, the aerosol generator 300 may include a reservoir that is configured to receive and/or house a volume of liquid medicament to be aerosolized. The aerosol generator 300 may be coupled to a medicament feed line 306 that is configured to deliver a volume of liquid medicament to the reservoir, such as via a pump (not shown). The aerosolization device may also include a cable 308 that is connected to a power source, although in some embodiments the aerosolization device may be battery powered.

In some embodiments, the aerosolization device may include an inlet 310 and an outlet 312 that may be respectively coupled to an inspiratory limb and an expiratory limb of an artificial respiration system. Potential artificial respiration systems include, but are not limited to, ventilators, humidifiers, CPAP machines, and/or combinations thereof. In some embodiments, the inlet 310 and outlet 312 may be a single unit forming a flow path for respiratory gases, while in other embodiments the inlet 310 and outlet 312 may be separate components that are coupled together. The inlet 310 and/or outlet 312 may be configured to receive ends of gas conduits of the respiration system. For example, inlet and/or outlet airflow baffles may support the one-way circuit of standard nCPAP circuits. This enables the baffles to minimize disruption of airflow from inlet to outlet resulting in less disturbance of the aerosol chamber 302.

Figure 3A:
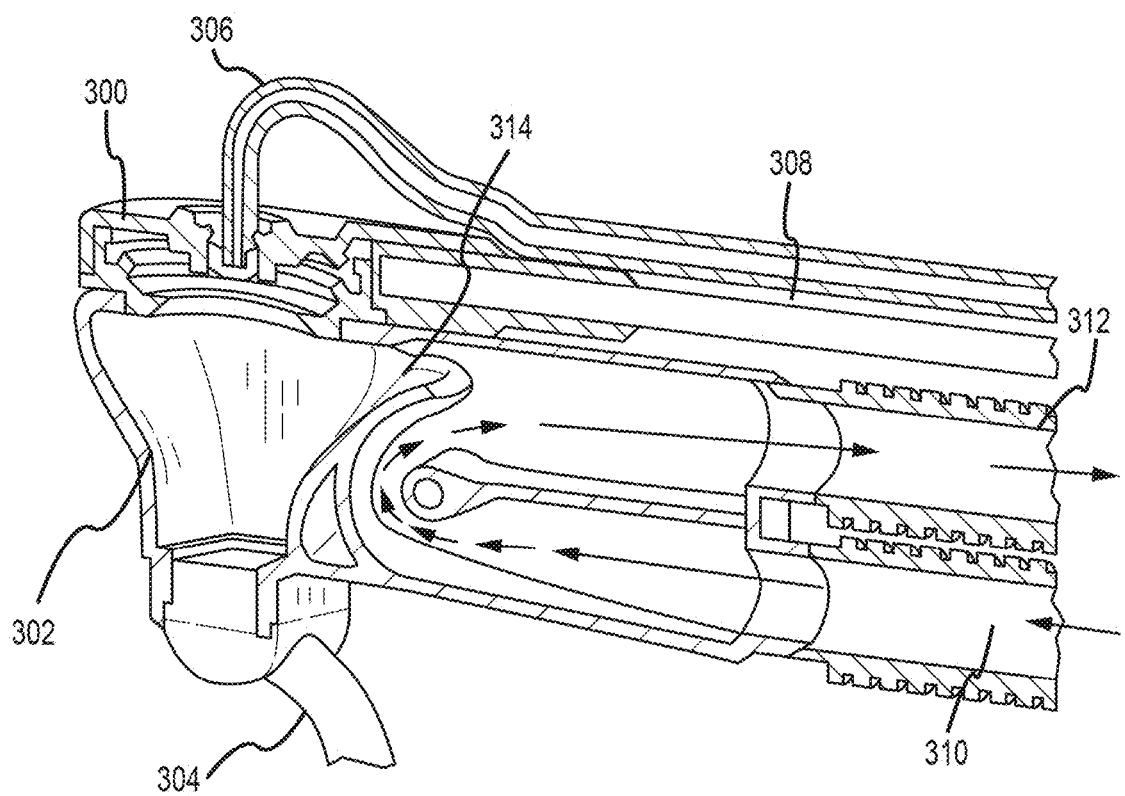
FIG. 3A is a cross-sectional view of the aerosolization device of FIG. 3.

As seen in FIG. 3A, the aerosolization device also includes a fluid flow path 314 that connects the aerosol chamber 302 with the inlet 310 and/or the outlet 312. As shown here, fluid flow path 314 may deliver respiratory gases to a top portion of the aerosol chamber 302 proximate the aerosol generator 300, although in some embodiments other locations, such as medial portions of the aerosol chamber 302 and/or portions proximate the patient interface 304 may be contemplated. Fluid flow path 314 may intersect with the inlet 310 and/or outlet 312 in such a manner that the fluid flow path 314 forms no greater than a 90 degree angle with an upstream side of the inlet 310 and/or outlet 312 and/or a flow path formed within the inlet 310 and/or outlet 312, such that the gas flow path 314 is orthogonal to the inlet 310 and/or outlet 312 or extends in a direction that at least partially opposing the flow of air though the inlet 31 and/or outlet 312. Such positioning of the fluid flow path 314 helps to isolate the aerosol chamber 302 from the continuous flow of the respiratory gases flowing from the inlet 310 (inspiratory limb) to the outlet 312 (expiratory limb). This provides several benefits. First, the isolation of the aerosol chamber 302 from the continuous flow prevents aerosolized medicament from being "whipped away" or diluted by the gas flow. Secondly, the isolation allows for the pre-loading of the aerosol chamber 302 with aerosolized medicament immediately prior to a breath event, while also enabling any medicament left over from a previous breath to be preserved.

In some embodiments, a portion of the respiratory gases may be drawn through the fluid flow path 314 and into the aerosol chamber 302 for mixing with aerosolized medicament. The portion of the respiratory gases that are drawn into the aerosol chamber 302 may be drawn in via the vacuum created by the patient inhaling at the patient interface 304.

Aerosol chamber 302 has an inner geometry that is optimized to direct plume towards the patient interface 304 with minimal impact action. Specifically, the aerosol chamber 302 is designed such the aerosol generator 300 is positioned opposite the patient interface 304. Additionally, the aerosol chamber 302 is designed with a generally funnel-shaped profile, which helps to reduce impaction when aerosol exits the aerosol generator 300 by providing a wider portion that tapers (linearly or nonlinearly) to a narrow portion proximate the patient interface 304. Such a design also helps to minimize the size of the aerosol chamber 302.

Figure 4B:
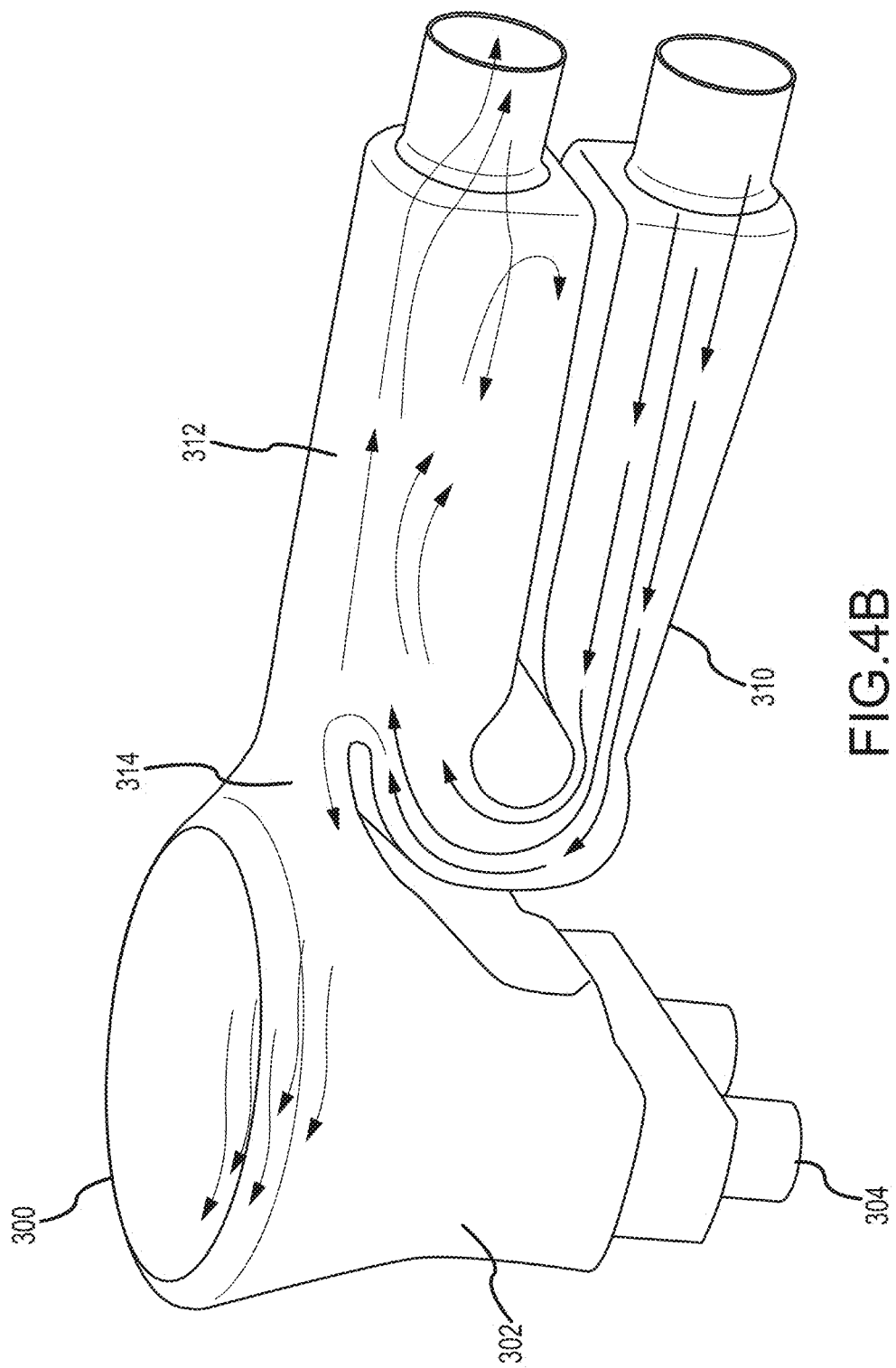
FIG. 4B illustrates flow patterns through the aerosolization device of FIG. 3.

FIGS. 4A and 4B depict flow paths of respiratory flow from a high flow respiration system through the aerosolization device of FIGS. 3 and 3A. Inspiratory flow is flowing through the inlet 310 at a rate of 8 L/min while the patient inhales at a rate of 1 L/min. Pressure at the expiratory limb coupled with the outlet 312 is 5 cm $H_2O$. A portion of the respiratory gases are drawn through fluid flow path 314 and into the aerosol chamber 302 as the patient inhales through the patient interface 304.

Figure 5A:
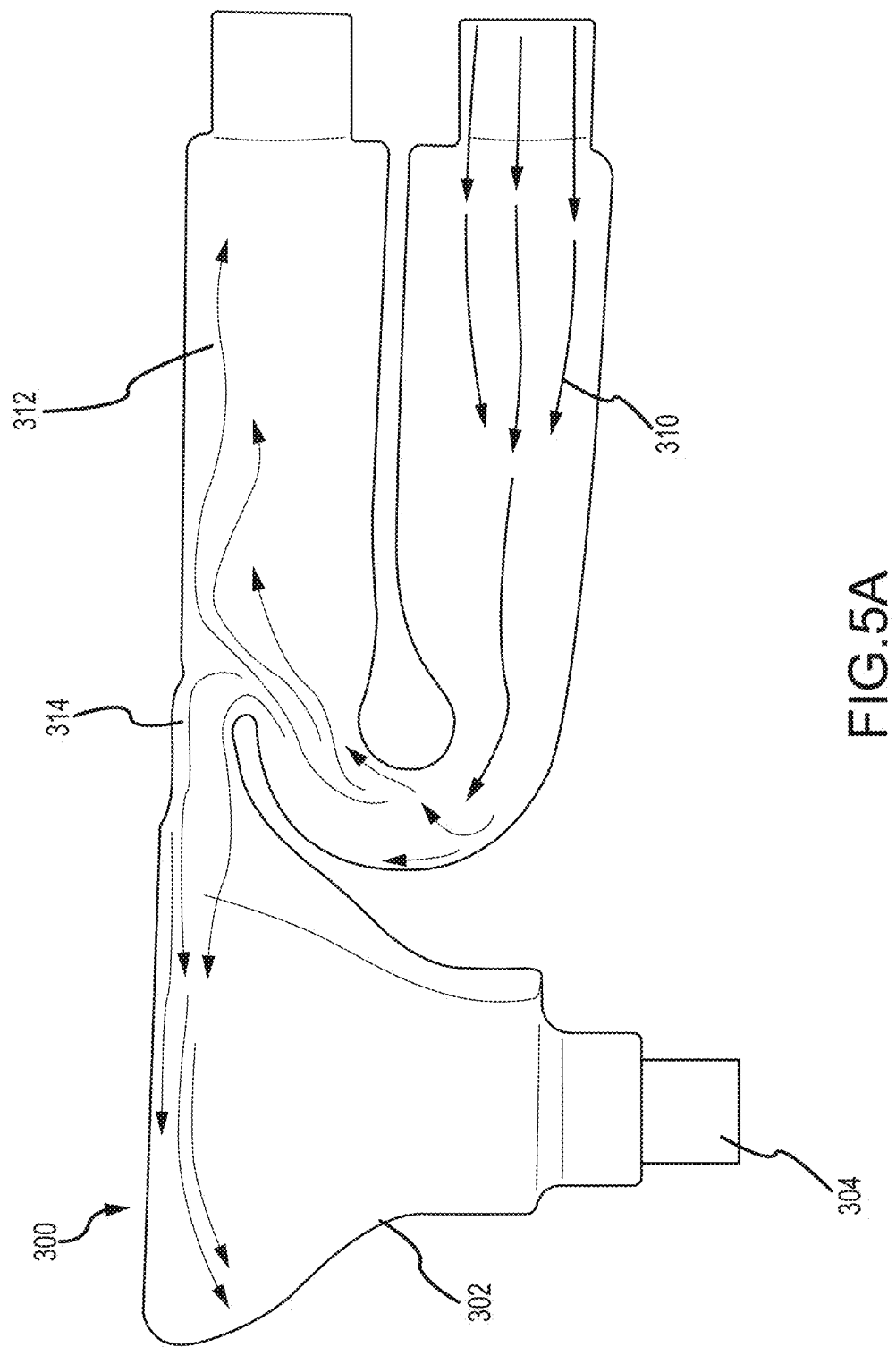
FIG. 5A illustrates flow patterns from a low flow respiration system through the aerosolization device of FIG. 3.

FIGS. 5A and 5B depict flow paths of respiratory flow from a low flow respiration system through the aerosolization device of FIGS. 3 and 3A. Inspiratory flow is flowing through the inlet 310 at a rate of 2 L/min while the patient inhales at a rate of 1 L/min. Pressure at the expiratory limb coupled with the outlet 312 is 5 cm $H_2O$. Similar to the high flow embodiment, a portion of the respiratory gases are drawn through fluid flow path 314 and into the aerosol chamber 302 as the patient inhales through the patient interface 304. As seen in FIG. 5B, the portion of respiratory flow that is drawn into the aerosol chamber 302 is introduced to the patient's airway via patient interface 304.

Figure 6:
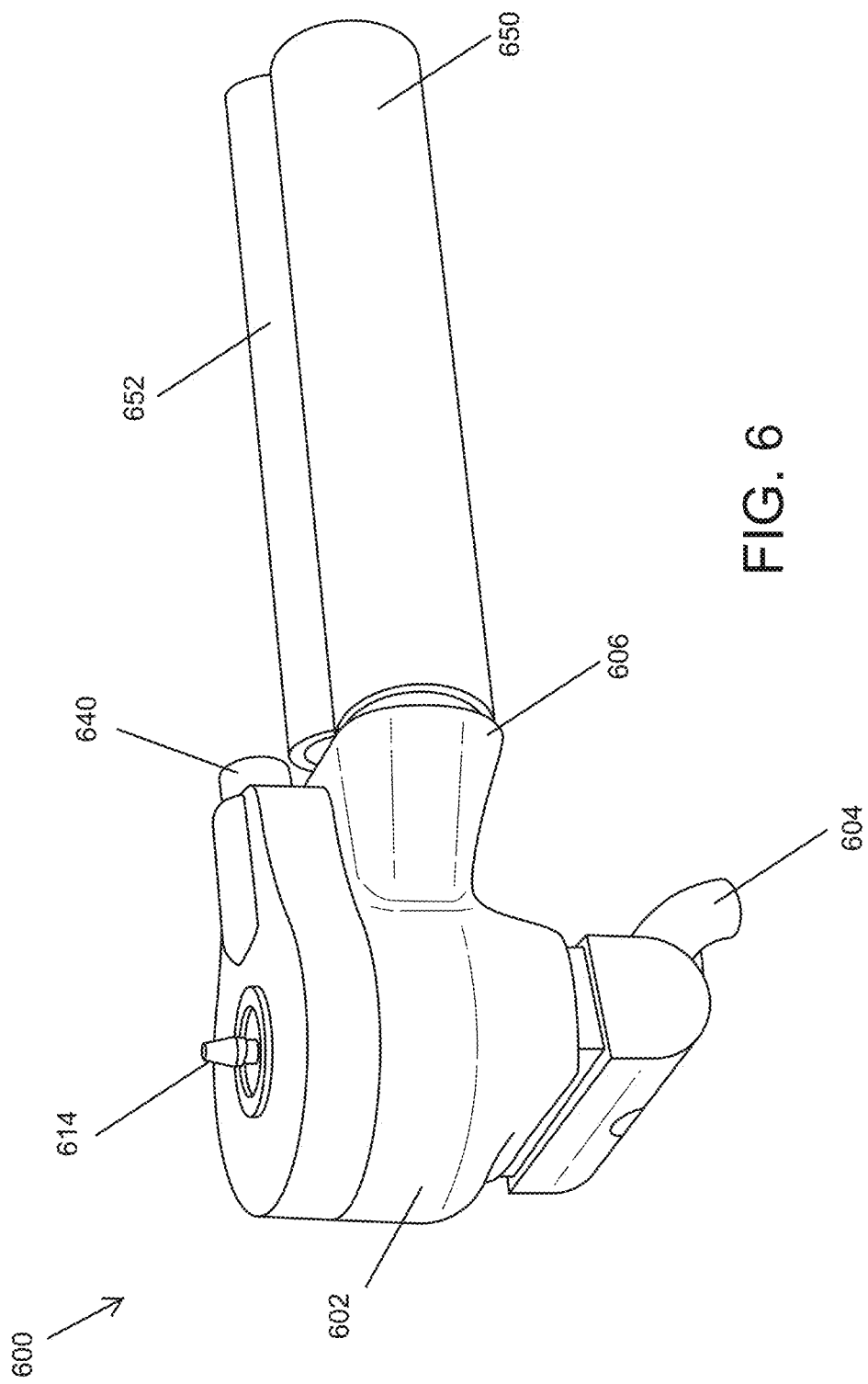
FIG. 6 illustrates an isometric view of an aerosolization device according to embodiments.

FIGS. 6-6D illustrate another embodiment of an aerosolization device 600. Here, an aerosol generator 612 (shown in FIGS. 6A-6D), similar to those described above, is positioned on a first side of an aerosol chamber 602 with a patient interface 604 being positioned on an opposite, second side of the aerosol chamber 602. The aerosol generator 612 may include a reservoir that is configured to receive and/or house a quantity of liquid medicament to be aerosolized. For example, in some embodiments, the aerosolization device 600 may include at least one medication supply port 614 that is configured to be coupled with a medication supply line (not shown) that is used to deliver liquid medicament to the aerosol generator 612 (such as to the reservoir, if present). In some embodiments, the reservoir may be in the form of an elongate conduit that extends between the medication supply port 614 and the aerosol generator 612. In some embodiments, the patient interface 604 may include nasal prongs, endotracheal tubes, nasal cannula/masks, tracheostomy tubes, and the like. The aerosolization device 600 may also include at least one power connection 640. As illustrated, power connection 640 is a port that allows a power cable to be connected to the aerosolization device 600 to supply power and/or control commands to the aerosol generator 612.

The device includes a respiratory adaptor 606 that is configured to interface with an artificial respiration system, such as a ventilator, humidifier, continuous positive airway pressure (CPAP) machine, nCPAP system, and/or combinations thereof. For example, the respiratory adaptor 606 may include an inlet 608, such as an inlet baffle, that is configured to couple with an inspiratory limb 650 of a respiration system. The respiratory adaptor 606 may also include an outlet 616, such as an outlet baffle, that is configured to interface with an expiratory limb 652 of a respiration system. For example, as illustrated the inlet 608 and/or outlet 616 may be configured to be inserted and retained (such as using a friction fit and/or other securement mechanism) within a conduit of the inspiratory limb 650 and expiratory limb 652, respectively. In other embodiments, the inlet 608 and/or outlet 616 may be configured to be larger than the conduits of the respirations system such that conduits of the inspiratory limb 650 and/or expiratory limb 652 may be inserted and retained (such as using a friction fit and/or other securement mechanism) within the inlet 608 and outlet 616, respectively. It will be appreciated that other techniques for interfacing the inlet 608 and/or outlet 616 with a respiration system may be utilized and that the inlet 608 and outlet 616 need not be interfaced using the same techniques.

Figure 6A:
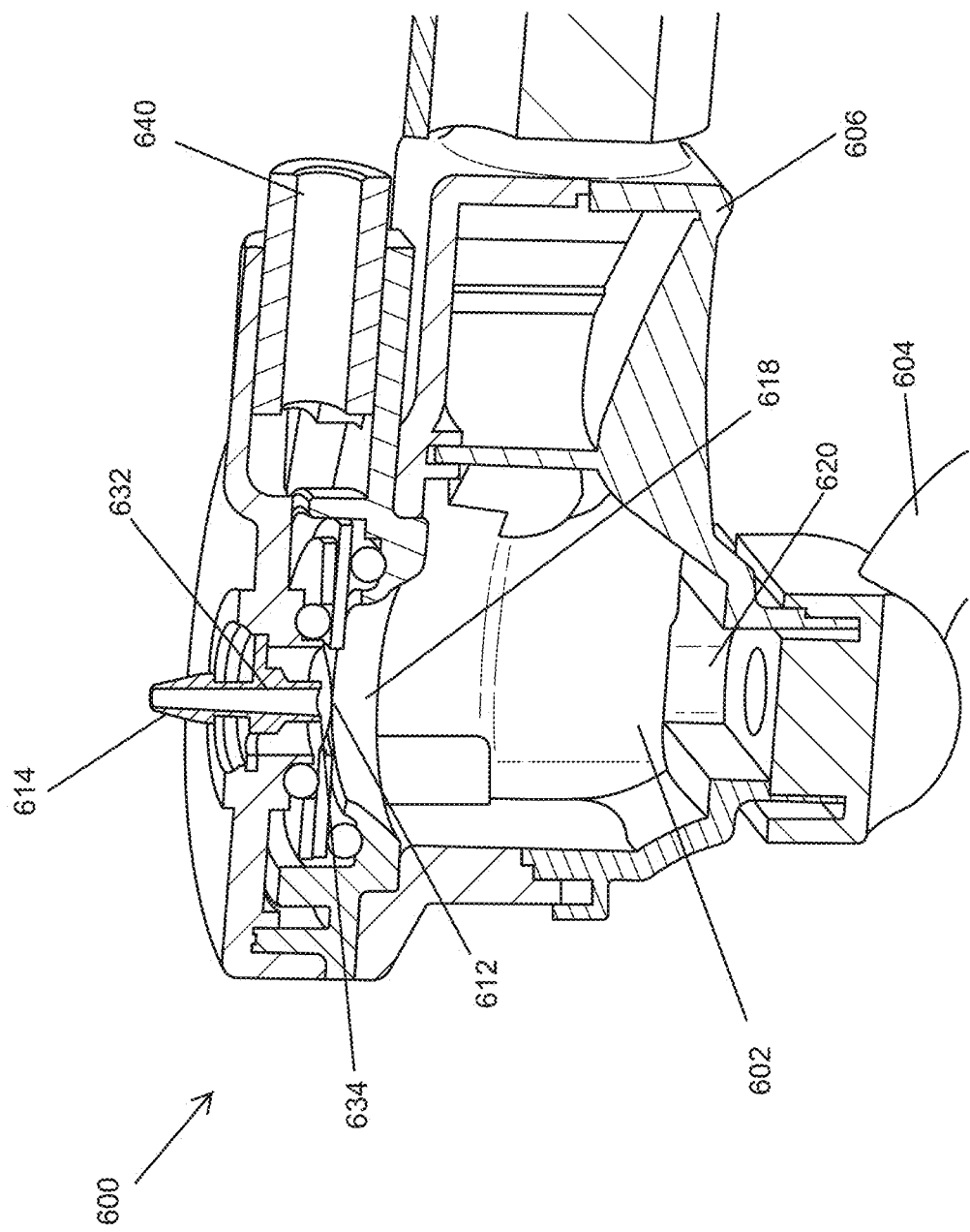
FIG. 6A is a cross-sectional view of the aerosolization device of FIG. 6.

FIG. 6A shows a cross-sectional view of the aerosolization system of FIG. 6. Here, the aerosol generator 612 of the aerosolization device 600 is shown positioned at a first end 618 of the aerosolization chamber 602 such that any medicament that is aerosolized by the aerosol generator 612 is introduced into the aerosol chamber 602. For example, the medicament may be delivered to the aerosol generator 612 via the medication supply port 614, which is in communication with a reservoir. In some embodiments, the reservoir may be a "virtual reservoir" in the form of a conduit 632 that delivers the medicament to a surface of the aerosol generator 612. The virtual reservoir, conduit 632, may be coupled with a medicament source, such as a vial, via a fluid line that is coupled with the medication supply port 614. A distalmost tip 634 of the conduit 632 may have a diameter that is less than or equal to the distance between the tip 634 and a proximal surface of a mesh of the aerosol generator 612. Such dimensioning ensures that drops of liquid medicament ejected from the tip 634 are sufficiently large to contact and transfer to the mesh of the aerosol generator 612. Surface tension ensures that the liquid stays on and spreads out along a surface of the mesh such that all or substantially all of the liquid is aerosolized. This allows the aerosolization device 600 to be operated in any orientation, allowing the patient (such as an infant) to be treated while on their side, back, or stomach. For example, in some embodiments, a tip of the medication supply port 614 may be positioned between about 5-40 microns from a surface of the aerosol generator 612, while the tip 364 has a diameter that is less than or equal to this distance. As illustrated, the aerosol generator 612 is placed proximate to the patient interface 604, as the only component separating the aerosol generator 612 from the patient interface 604 is the aerosol chamber 602. Such placement of the aerosol generator 612 proximate to the patient interface 604 allows aerosolized medicament emitted during inspiratory cycle to preferentially be inhaled with minimal disruption of continuous or bias flow passing through the respiration system circuit. Here, aerosol chamber 602 is shown with the first end 618 being smaller than a second end 620, which helps to reduce impaction when aerosol exits the aerosolization device 600.

The inlet 608 may be formed of a baffle that is designed to draw a portion of the respiratory flow from the inspiratory limb 650 of the respiration system into the aerosol chamber 602 at a position near the first end via a fluid pathway that will be described in greater detail in relation to FIGS. 6B and 6C. In some embodiments, the inlet 608 may be designed to redirect gas from the respiration system to the aerosol chamber 602, without substantially increasing resistance or work (e.g. inspiratory pressure) of breathing for the patient, or at least to any significant degree. This may be done by providing a fluid pathway in the respiratory adaptor 606 that includes a number of baffles that direct a portion air from the inspiratory limb (only enough for inspiration) into the aerosol chamber 602 in a manner that significantly reduces turbulence in the airflow that is drawn into the aerosolization device 600, thereby creating a more laminar flow within the aerosol chamber 602.

Figure 6B:
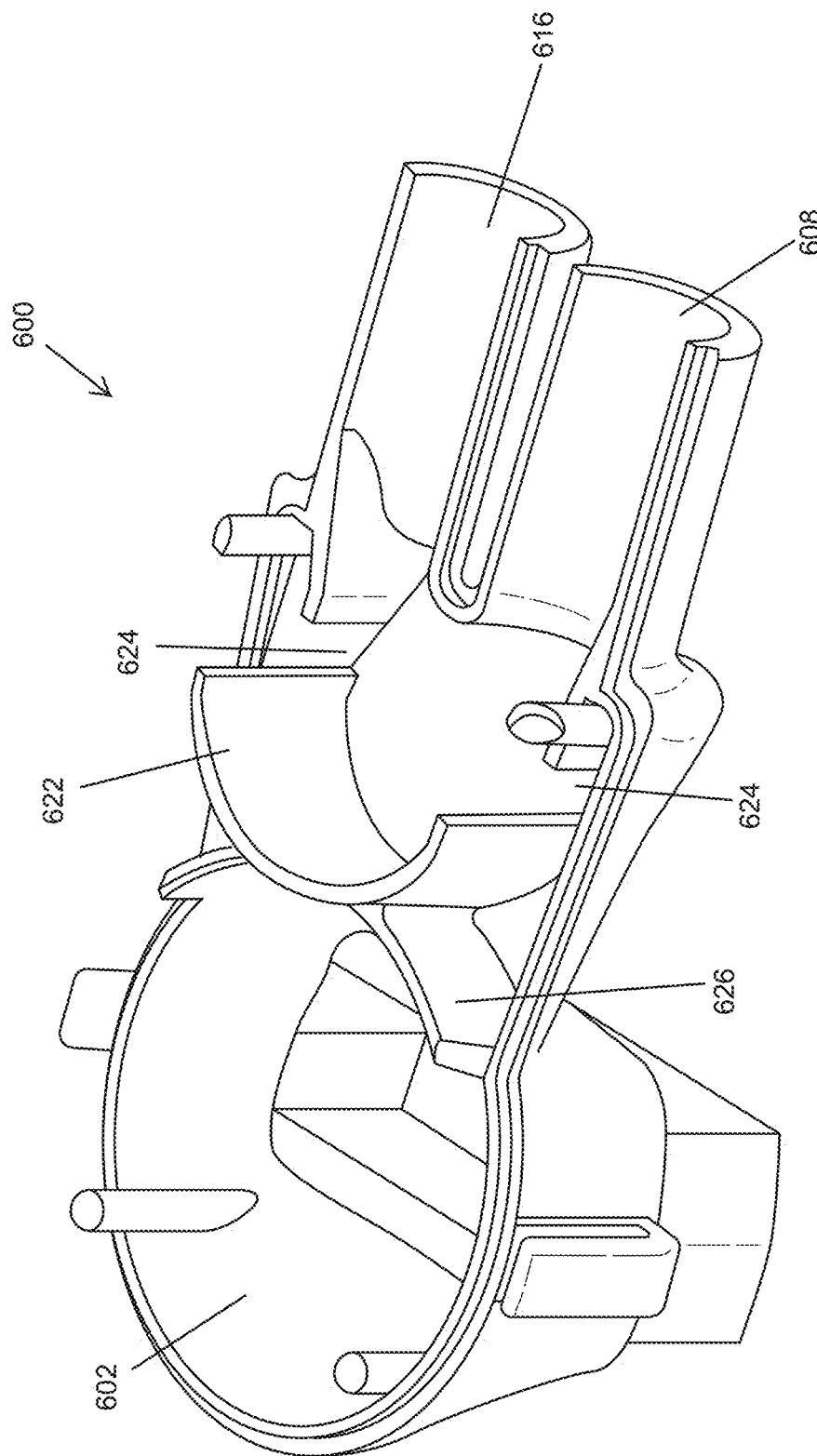
FIG. 6B is a cross-sectional view of the aerosolization device of FIG. 6.
Figure 6C:
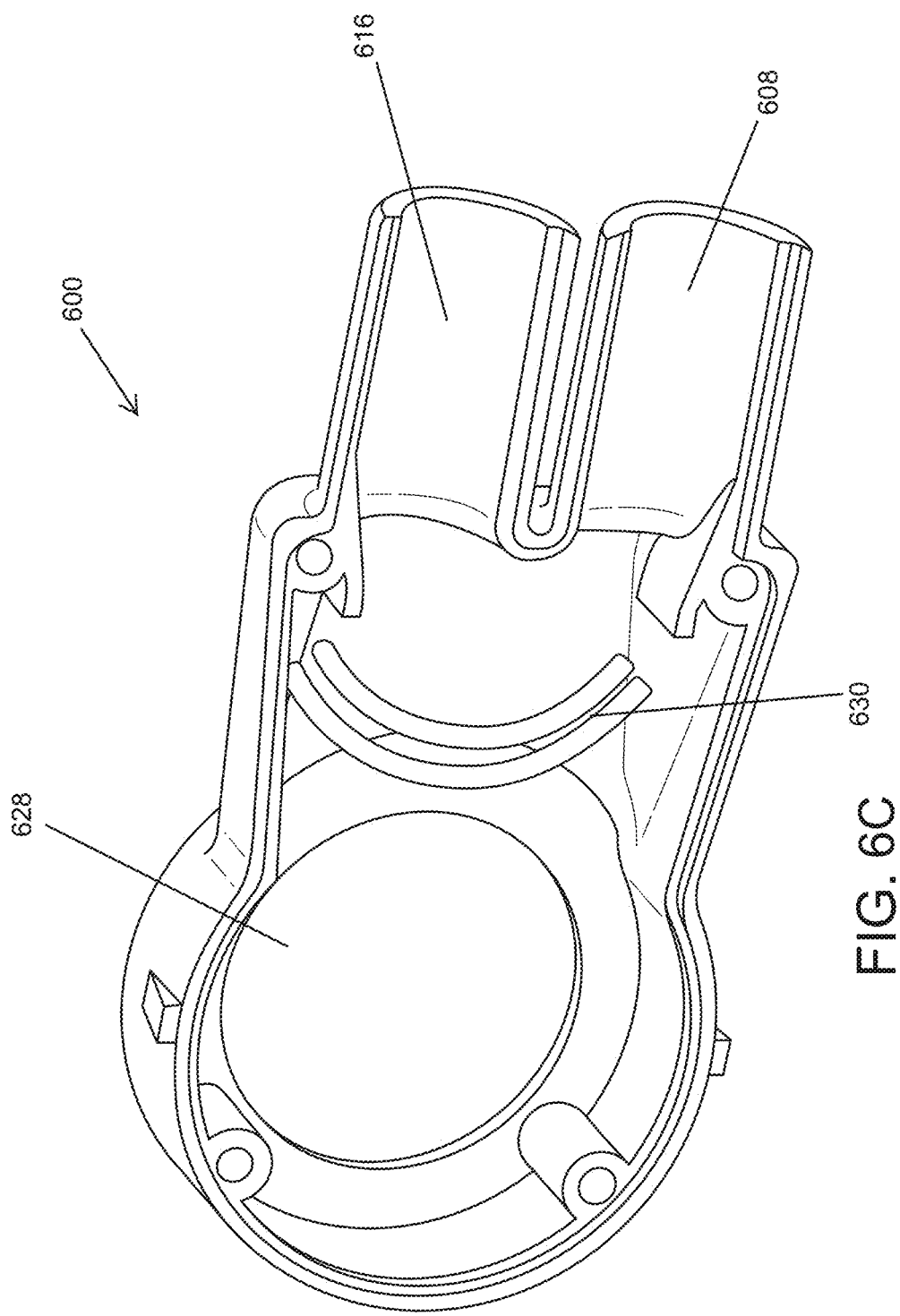
FIG. 6C is a cross-sectional view of the aerosolization device of FIG. 6.

FIGS. 6B and 6C illustrate two halves of aerosolization device 600. While illustrated as being two separable components, it will be appreciated that aerosolization device 600 may include any number of components that may be coupled together (such as using connecting/mating features) and/or may be formed from a single component, which may be formed from known molding, 3D printing, and/or other manufacturing techniques, both known and unknown. As shown in FIG. 6B, a portion of the aerosolization device 600 that includes the fluid flow path including a number of baffles. In the illustrated embodiment, aerosolization device 600 includes a first baffle 622 that directs a significant amount of the flow from the inspiratory limb 650 to the expiratory limb 652, while allowing a portion of the flow from the inspiratory limb 650 to enter the aerosol chamber 602. For example, the baffle 622 may be generally U-shaped, with one or both ends being open to form airways 624 between the baffle 622 and the sidewalls of a housing of the aerosolization device 600 that allow a small amount of air to flow past the ends of the baffle 622, while a body of the baffle 622 prevents the remaining air from getting past the baffle 622 and instead directs the air into the expiratory limb 652. It will be appreciated that while a U-shaped baffle 622 is used in the present embodiment, other shapes may be used to meet the needs of a particular application.

The aerosolization device 602 may include a second baffle 626 that is positioned proximate the baffle 622. As illustrated, the second baffle 626 is in the form of a generally U-shaped barrier that is oriented in an opposite direction as baffle 622 (although other shapes and orientations of second baffle 626 are possible, such as a second baffle 626 that extends across a width of the interior of the aerosolization device 600 in a generally linear fashion and/or a second baffle that curves or is otherwise oriented in a same direction as baffle 622). In some embodiments, the first baffle 622 and the second baffle 626 may be a single component, such as by sharing a medial portion, while other embodiments utilize baffles that are separate components. As shown, second baffle 626, extends all the way to the sidewalls of the housing, but leaves a gap between a distal edge of the second baffle 626 and a top portion of the housing of the aerosolization device 602 that provides a pathway for air to enter the aerosolization chamber 602. Thus, as illustrated, as a patient inhales at the patient interface 604, a portion of the gases supplied by the inspiratory limb 650 are drawn through the airways 624 on one or more ends of the baffle 622, where the air is forced upward over the second baffle 624 and forms a generally laminar flow within the aerosol chamber 602. It will be appreciated, however, that in some embodiments rather than directing the airflow toward a top of the housing, the second baffle 626 may direct air to a bottom of the housing and/or to a central opening formed between a top and bottom baffle. Any number of designs of baffles and/or other diversion mechanisms (including valves) may be used to help isolate the aerosol chamber 602 from the direct flow of respiratory gases of the respiration system, while providing some flow of respiratory gases during inhalation of the patient.

FIG. 6C illustrates another portion of the aerosolization device 600 that interfaces with the first portion. This portion of the aerosolization device 600 defines a seat 628 for receiving the aerosol generator 612, medicament supply port 614, and/or other related components. A mating feature 630 may also be provided that receives and secures the baffle 622 in place. For example, the mating feature 630 may define a groove or channel that is sized and shaped to receive a top edge of the baffle 622. This connection ensures that the baffle 622 may extend all the way from a bottom surface of the housing of the aerosolization device 600 to a top surface of the housing, which ensures that only airflow through airways 624 on either end of the baffle 622 is permitted to pass beyond the baffle 622 while directed a substantial portion of the airflow to the outlet 616.

FIG. 6D illustrates a flow pattern for airflow that is drawn into the aerosolization device 600 via inlet 608 from the inspiratory limb 650. For example, air from the inspiratory limb 650 (which may pass through a humidifier), may pass through the respiratory adaptor 606, where the baffle 622 redirects a significant portion of the air into the expiratory limb 652 via the outlet 616. As described above, the baffle 622 provides one or more airways 624 that allow a portion of the airflow from the inspiratory limb 650 to be drawn inward on each inhalation of the patient. This portion of the air is drawn in through the airways where it encounters the second baffle 626. The second baffle 626 forces air that is drawn past the ends of the baffle 622 upward, where the air flows over the second baffle 626 and into the aerosolization chamber 602. As illustrated here, the air is introduced into the aerosol chamber 602 at a position near the first end 618 proximate the aerosol generator 612. In other embodiments, the airflow may be introduced into the aerosol chamber 602 at other locations. As just one example, the air may be introduced near sidewalls of the aerosol chamber 602 using a baffle similar to baffle 622. As illustrated here, the air is introduced into the aerosolization chamber 602 as a position near the first end 618 proximate the aerosol generator 612. In other embodiments, the airflow may be introduced into the aerosolization chamber 602 at other locations. As just one example, the air may be introduced near sidewalls of the aerosolization chamber 602 using a baffle similar to baffle 622. It will be appreciated that other designs and/or locations of baffles may be utilized to introduce air to the aerosolization chamber 602 while isolating the aerosolization chamber 602 from direct flow within the respiration system. Additionally, some embodiments may utilize other mechanisms to divert some air from the respiration system into the aerosolization chamber 602 during each inspiration of the patient. For example, some embodiments may incorporate one or more one-way valves that are disposed between the aerosolization chamber 602 and the inspiratory limb 650 and/or expiratory limb 652. The one or more valves seal off and/or otherwise isolate the aerosolization chamber 602 from the respiration system until the patient breathes in, at which time the one or more valves open and allow a small volume of respiratory flow into the aerosolization chamber 602.

By using a series of baffles that direct small amounts of air from the inspiratory limb 650 into the aerosol chamber 602, embodiments of the present invention ensure the air drawn into the aerosol chamber 602 may be less turbulent and more laminar, which provides better deposition of medicament within the lungs. The baffles may be designed so that the gas/air that is drawn past the baffles is at or near the inspiratory flow of infants (which is much lower than gas passing through the inspiratory limb 650. It will be appreciated that while two baffles are used in the illustrated embodiments, other numbers and arrangements of baffles may be utilized to reduce the turbulence within the airflow from the inspiratory limb 650 prior to introducing the airflow into the aerosol chamber 602 without providing a significant increase to the amount of inhalation force needed to draw air into the patient's airways. Additionally, while shown with U-shaped baffles it will be appreciated that other baffle designs may be used that both limit the amount of airflow that is drawn into the aerosol chamber 602 during each inhalation and reduce the amount of turbulence within such airflow. This also helps reduce the dilution of the aerosolized medicament in the air supplied by the inspiratory limb 650.

Figure 7:
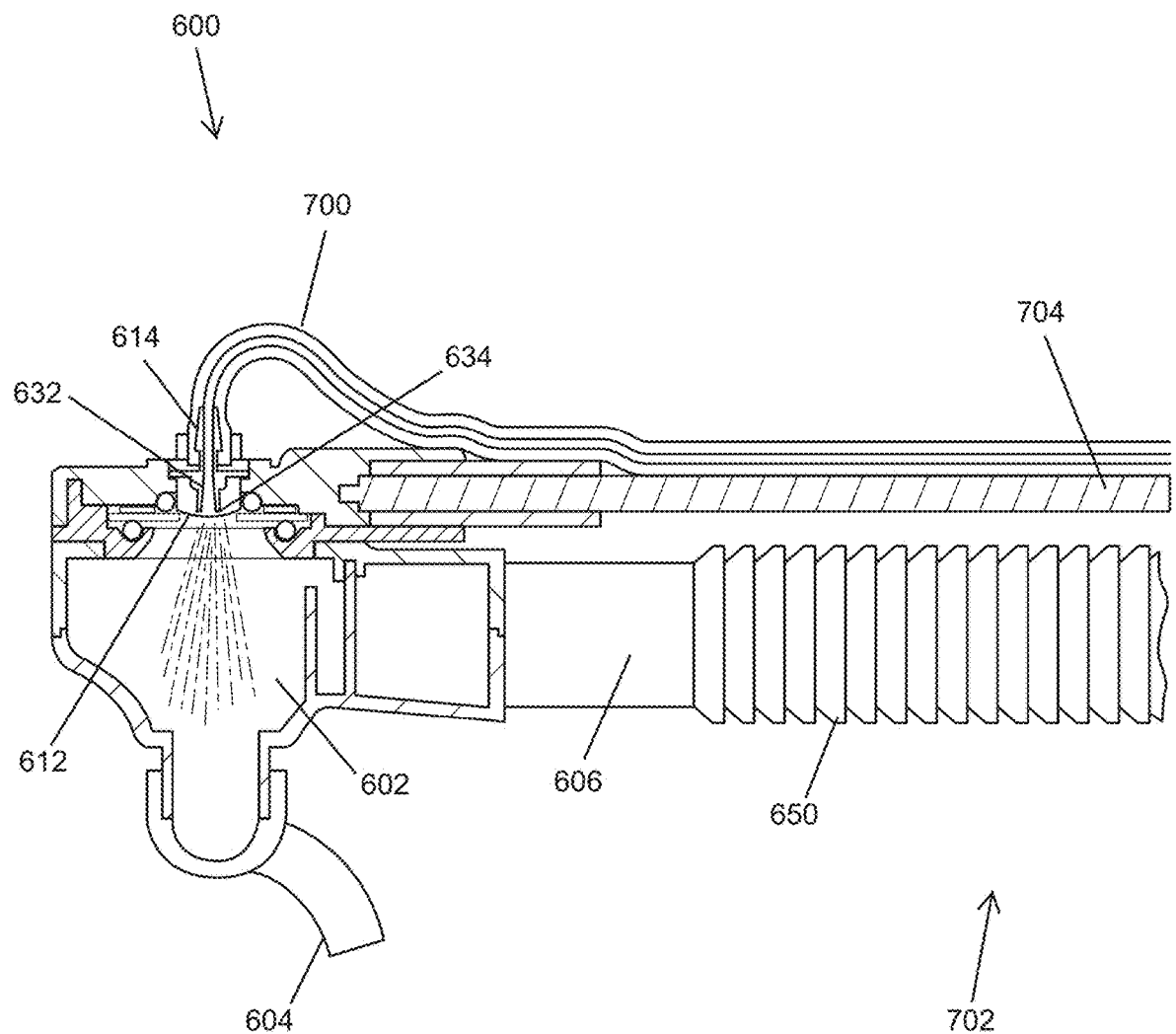
FIG. 7 illustrates the aerosolization device of FIG. 6 connected with a fluid supply line and a respiration system.

FIG. 7 illustrates the aerosolization device 600 of FIGS. 6-6D in a connected state with both a fluid supply line 700 and a respiration system 702. As illustrated, a first end of the fluid supply line 700 is coupled with the medication supply port 614. For example, in some embodiments, the medication supply port 614 includes a tip that protrudes outward from a body of the aerosolization device 600. An opening of the fluid supply line 700 may be fitted over the tip, thereby allowing fluids from the fluid supply line 700 to pass through the medication supply port 614 and into the reservoir and/or conduit 634 for subsequent delivery to the aerosol generator 602. A second end (not shown) of the fluid supply line 700 may be coupled with a fluid source, such as a vial (or other type of container) of liquid medicament.

The respiratory adaptor 606 may be coupled with the respiration system 702. As illustrated here, the inlet 608 is coupled with an inspiratory limb 650 of the respiration system 702, while the outlet 616 and expiratory limb 652 are obscured. Air and/or other respiratory gases may pass from the inspiratory limb 650 into the respiratory adaptor 606, where one or more diversion mechanisms, such as valves, baffles, and the like, may divert a portion of the airflow into the aerosol chamber 602 via a fluid path, while a remaining larger portion of the airflow of the respiration system 702 is directed through the expiratory limb 652 by the respiratory adaptor 606.

A nebulizer cable 704 is connected with power connection 640. Nebulizer cable 704 is configured to deliver power to the aerosol generator 602, as well as provide operation commands (such as commands that control when and how long the aerosol generator 602 is actuated. For example, a controller (not shown) may be coupled with the aerosolization device 600 via the nebulizer cable. The controller may monitor a respiratory cycle of the patient using one or more breath sensors. Based on this information, the controller may send signals using the nebulizer cable 704 (or other communications link) that activate a pump to deliver liquid to the aerosol generator 612 and that activate the aerosol generator 612 to aerosolize the medicament.

Figure 8:
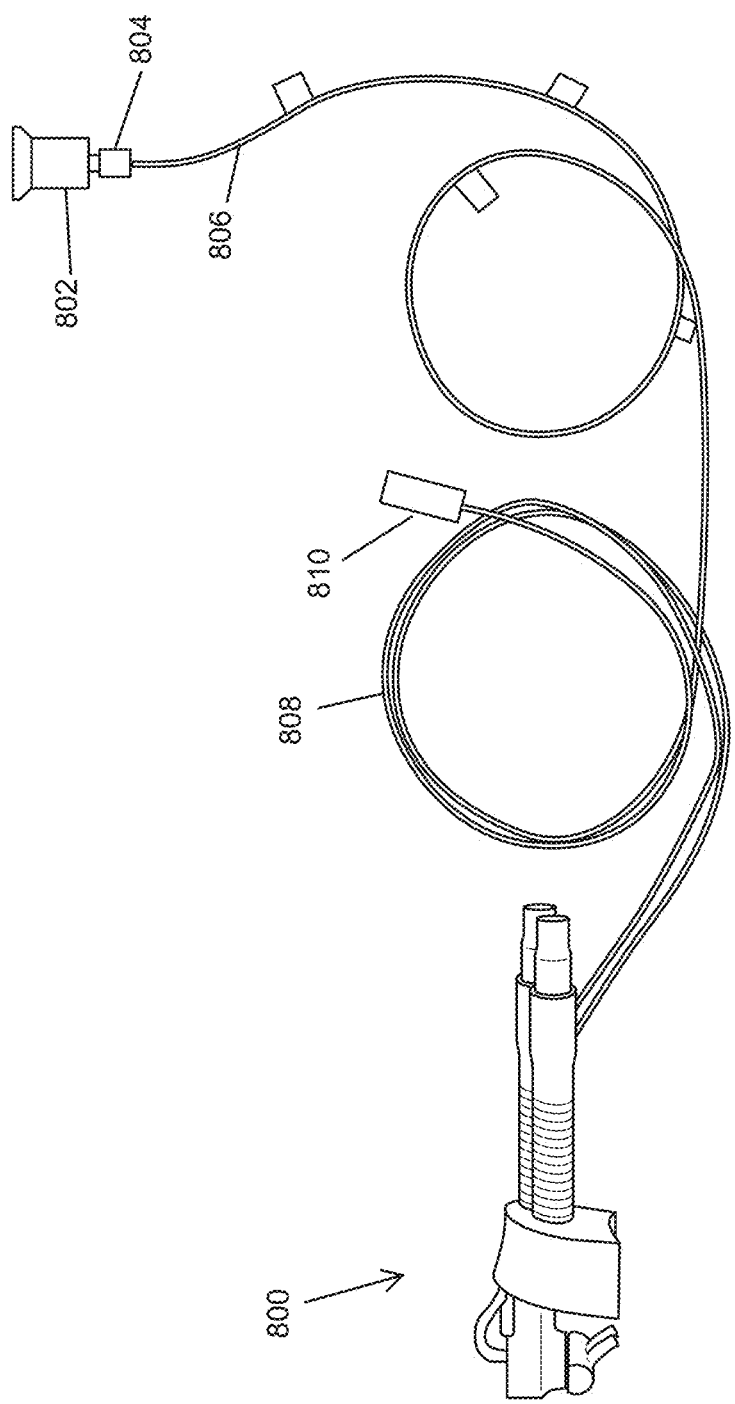
FIG. 8 illustrates an aerosolization device connected with a medication source.

FIG. 8 illustrates another embodiment of an aerosolization device 800. Aerosolization device 800 may be similar to aerosolization device 600 described above. As illustrated, aerosolization device 800 is coupled with a medication source 802. Medication source 802 may be any container that holds a volume of medicament. As illustrated, medication source 802 is a vial that is coupled to a medication port of the aerosolization device via a Luer connection 804 and length of a fluid supply line 806. Also coupled with the aerosolization device 800 is a nebulizer cable 808 that is connectable with a controller (not shown). The nebulizer cable 808 terminates in a pod 810 that is usable to couple the aerosolization device 800 and/or a respiration sensor with the controller.

Figure 9:
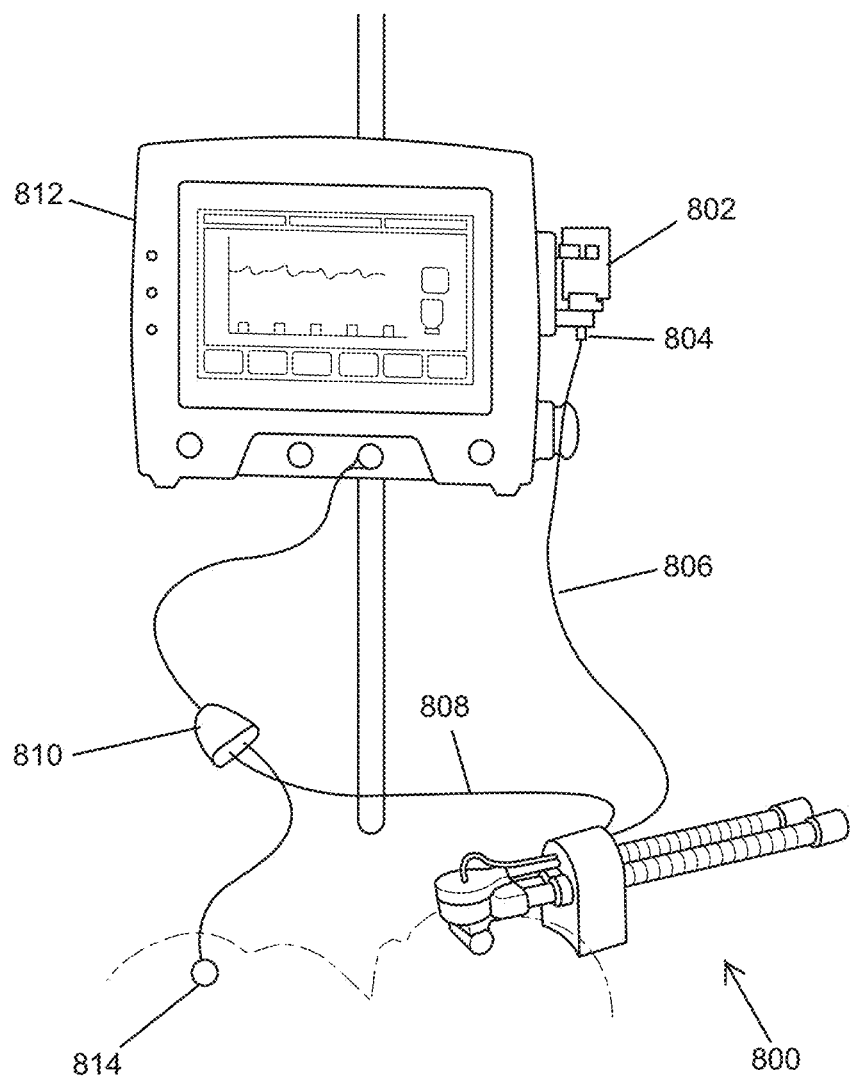
FIG. 9 illustrates the aerosolization device of FIG. 8 connected with the medication source and a controller.

FIG. 9 illustrates the aerosolization device 800 connected to medication source 802 and a controller 812. The controller may be configured to cause the liquid medicament to be delivered to the aerosolization device 800 via the fluid supply line 806 and to actuate the aerosolization device 800. In some embodiments, the controller 812 may actuate the aerosolization device 800 based on a detected inhalation of a patient. For example, the controller 812 may be coupled with a respiration sensor 814, which may detect the start, duration, and/or end of an inhalation of the patient. In some embodiments, the respiration sensor 814 may be a sensor similar to a Graseby sensor, which may be positioned against a torso (abdomen and/or chest) of the patient to detect a respiratory cycle of the patient. As such one example, the controller 812 may receive a signal from the respiration sensor 814 that indicates that the patient is starting to inhale. The controller 812 may then send commands that cause a volume of liquid medicament to be supplied to the aerosol generator of the aerosolization device 800 and that cause the aerosol generator to activate to aerosolize the liquid medicament during the inhalation.

Figure 10:
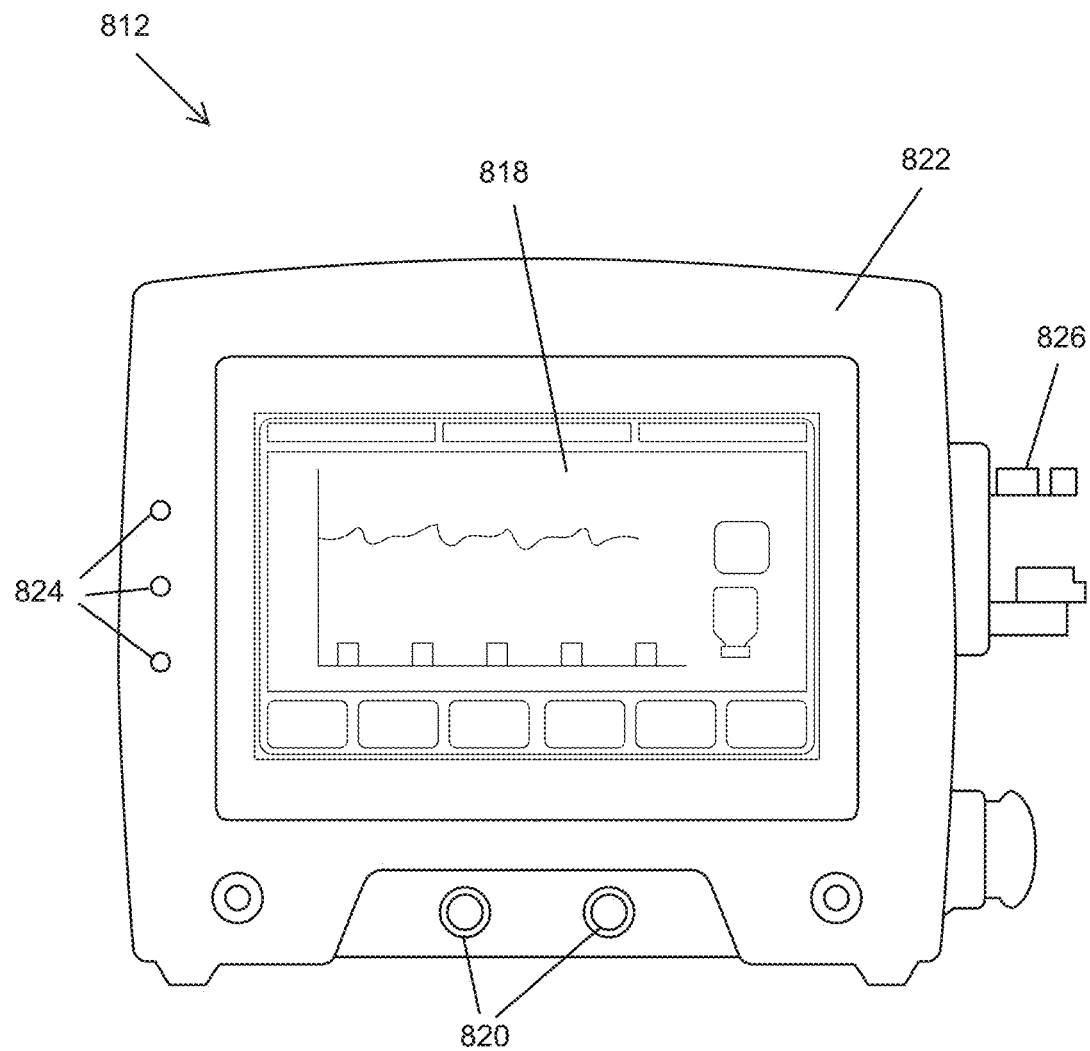
FIG. 10 illustrates the controller of FIG. 9.
Figure 11:
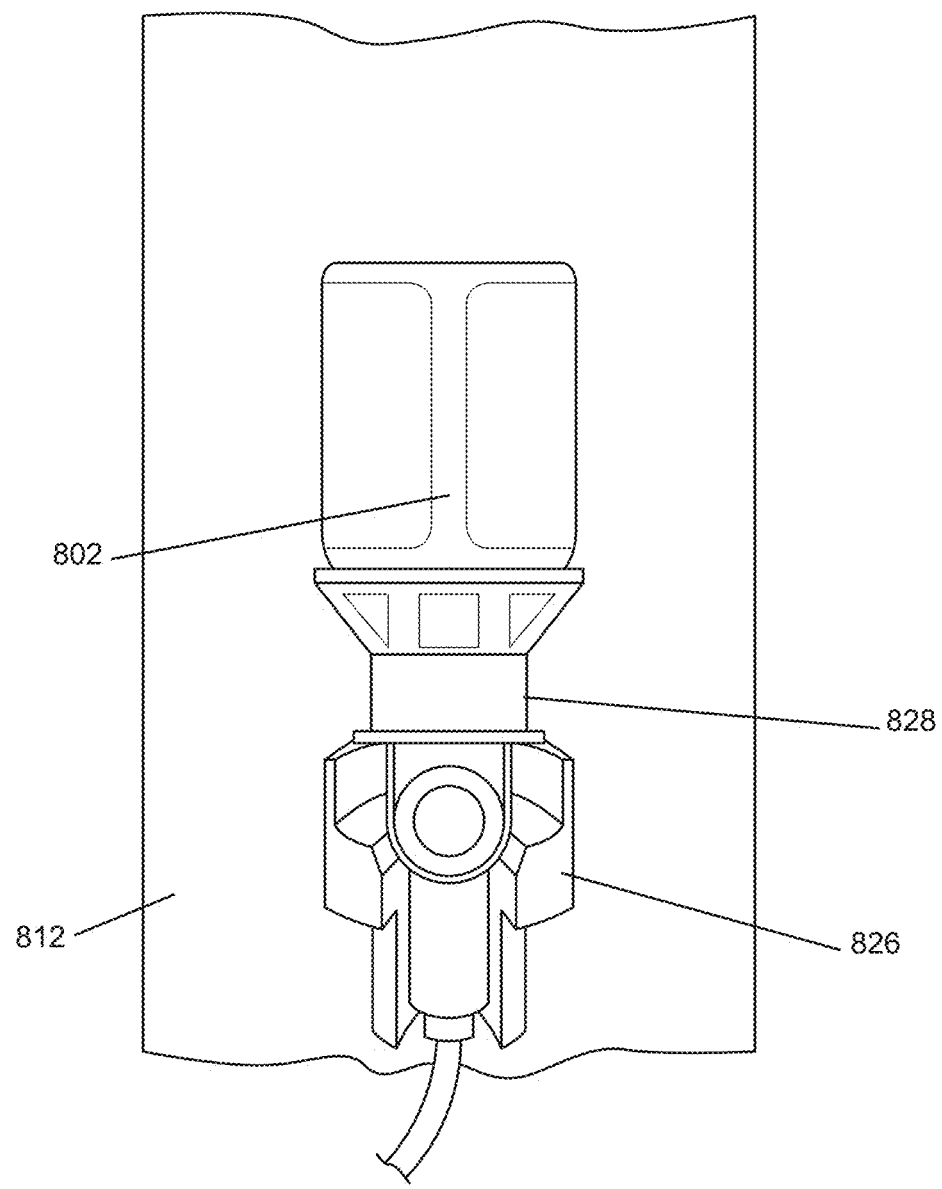
FIG. 11 illustrates a vial holder of the controller of FIG. 9.

In some embodiments, the respiration sensor 814 and/or aerosolization device 800 may be coupled directly to the controller 812. In other embodiments, a pod 810 and/or other adaptor may be used to connect the respiration sensor 814 and/or aerosolization device 800 with the controller 812. For example, in some embodiments connecting the respiration sensor to the pod includes inserting a connection, such as a slip Luer, into a port of the pod 810. In the present embodiment, the respiration sensor 814 may be adhered and/or otherwise affixed to the patient's abdomen to begin sensing inspiration cycles FIG. 10 illustrates the controller 812. Controller 812 includes a user interface 818, such as a display screen. In some embodiments, the user interface 818 may be a touchscreen. The controller 812 may include one or more input devices, such as buttons, dials, keypads, touchscreens, and the like that allow a user to interact with the controller 812 to adjust settings, such as dose level, etc. The controller 812 may also include a number of ports 820 that may be used to connect the controller 812 to peripheral units, such as the aerosolization device 800 and/or respiration sensor 814. In some embodiments, the controller 812 may include one or more indicators 824, such as LEDs, that are configured to alert users of the status of various features. For example, the indicators 824 may inform users about whether the aerosolization device 800 and/or respiration sensor 814 are properly connected, whether a power source 832 of the controller 812 is active (i.e. plugged in and/or whether a battery (if present) is charging or charged), whether any faults in the system have been detected, etc. In some embodiments, the indicators 824 may be integrated into the user interface 818. A housing 822 of the controller 812 may include a holder 826 that is configured to securely receive the medication source 802, as best illustrated in FIG. 11. In this embodiment, the medication source 802 is a vial that is secured in an upside down orientation within the holder 826, allowing the entire contents of the medication source 802 to be drained, pumped, and/or otherwise delivered from the medication source 802 to the aerosolization device 802.

Figure 12:
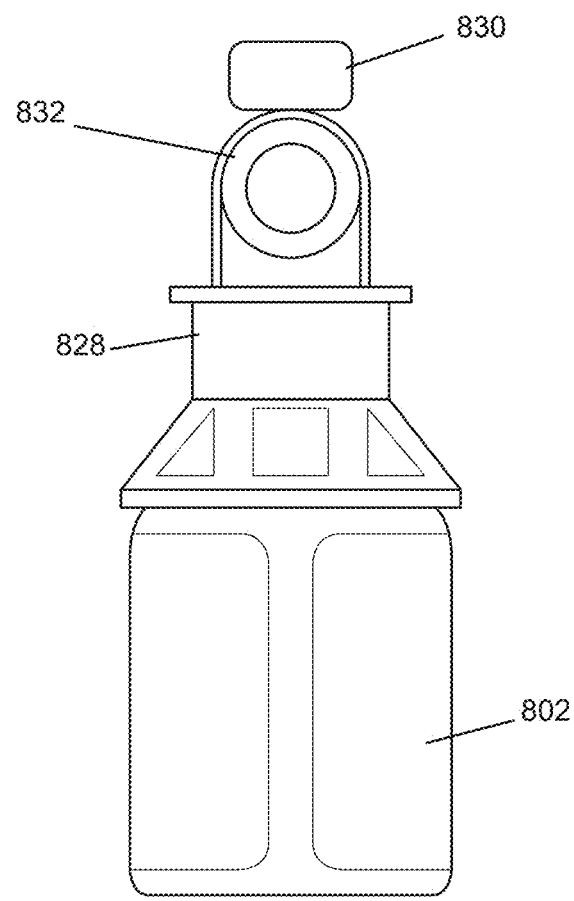
FIG. 12 illustrates the medication source of FIG. 9.

FIG. 12 illustrates medication source 802. Here, medication source 802 is in the form of a vial that is affixed with a vented vial access device (VVAD) 828. The VVAD 828 may include a removable cap 830 that seals an opening of the VVAD 828 when affixed to the VVAD 828. The VVAD 828 may also include a filter 832 that helps minimize aerosols within the vial and fluid supply line 806, minimize surface contamination, and neutralize vial pressure. In use, the cap 830 may be removed and a port (not shown) may be affixed to a Luer connector to couple the medication source 802 to the fluid supply line 806.

In some embodiments, the aerosolization devices described herein include an aerosol generator capable of coupling to a variety of artificial respiration systems. The aerosol generator may receive liquid medicament from a fluid source through a fluid delivery conduit. In operation, fluid from the fluid source is pumped with a pump through the fluid delivery conduit to the aerosol generator where the fluid is aerosolized before and/or while the patient inhales. In some embodiments, the fluid delivery conduit may be primed with fluid before treatment to ensure rapid delivery (e.g., preloading fluid in aerosol generator). The pump may controlled with a controller, which times delivery and dosage of the fluid.

The controller includes one or more processors that execute instructions stored on one or more memory to drive operation of the pump and the aerosol generator. For example, the memory may include instructions that indicate the amount of fluid to be pumped to the aerosol generator in each dose for each actuation of the aerosol generator, how much fluid is to be pumped over a specific period of time or times, etc. The stored instructions may be based on a size of the patient, age of the patient, sex of the patient, type of medicament, fluid additives, desired amount of aerosol, etc. The memory also includes instructions for activating the aerosol generator. As illustrated, the controller connects to the aerosol generator with a cable (i.e., electric cable), although in some embodiments the controller may be wirelessly connected to the aerosol generator. The cable carries a signal that activates a piezoelectric (or other) actuator inside the aerosol generator. As the piezoelectric actuator operates, it vibrates a vibratable member that then aerosolizes the fluid for delivery to the patient (i.e., through inhalation). The memory may therefore include instructions for controlling when the piezoelectric actuator starts, stops, vibration frequency or frequencies, etc.

The aerosolization systems described herein may increase treatment effectiveness by timing the creation of the aerosol. For example, the aerosol delivery system may begin aerosolizing the medicament before the patient inhales. In this way, the aerosol delivery system takes advantage of the increased airflow at the start of inhalation. This increases the medicament delivery to the patient as the inhaled air carries the medicament farther into the patient's lungs. The aerosol delivery system may also aerosolize medicament as soon as inhalation is detected (e.g., for spontaneous breathing).

The aerosol delivery system coordinates delivery of the medicament using one or more breath sensors to determine when a patient inhales and for how long. These breath sensors may communicate with the controller through wired connections and/or wireless connections. In some embodiments, the aerosol delivery system may use a combination of breath sensors to provide redundancy and/or more accurate monitoring of the patient's breathing cycle. As just one example, the aerosol delivery system may use a flow sensor in combination with a radar sensor to monitor both airflow and chest movement. As another example, the aerosol delivery system may use a flow sensor, a radar sensor, and plethysmography sensor to monitor the breathing cycle. It will be appreciated that any number and/or any combination of breath sensors may be utilized in a given application to monitor the patient's breathing cycle.

In some embodiments, the flow sensor couples to a gas delivery conduit to sense changes in airflow during inhalation (e.g., mandatory, assisted, or spontaneous breathing). In some embodiments, the flow sensor may also couple to a gas return conduit to detect the start and end of exhalation. And in still other embodiments, the aerosol delivery system may include flow sensors that couple to the gas delivery conduit and the gas return conduit. As the controller receives data from the flow sensor(s), the controller may monitor breathing patterns to predict when the patient is going to breath. The ability to predict when inhalation begins enables the aerosol delivery system to prepare aerosolized medicament for immediate inhalation. More specifically, the aerosol delivery system is able to preload fluid on a vibratable member in the aerosol generator so that the fluid can be aerosolized before inhalation. Because flow detection is not a lagging indicator, the flow sensor can rapidly detect unusual or spontaneous inhalation for aerosol delivery (e.g., less than 10 milliseconds from the start of inhalation).

Predicting the patient's inhalation may begin by using one or more breath and/or flow sensors to tracking the patient's breathing pattern and/or a ventilation cycle (if a patient is mandatorily ventilated). The controller then uses the tracked data to predict when subsequent inhalations will begin. This allows the controller to direct the pump to deliver fluid from the fluid source to the aerosol generator 16 prior to an inhalation. The controller may also signal the aerosol generator to begin aerosolizing the fluid at a proper time, such as within a predetermined time period (e.g., +/−0.5 seconds) before and/or during the predicted inhalation. In this way, aerosol is ready for the patient at the start of inhalation. While the aerosol delivery system is able to predict the breath cycle to produce aerosol for the patient, the aerosol delivery system is also able to recognize spontaneous/irregular breathing not part of the normal pattern using the breath sensors. Once a spontaneous breath is recognized, the aerosol delivery system may immediately pump fluid to the aerosol generator for delivery to the patient.

Figure 13:
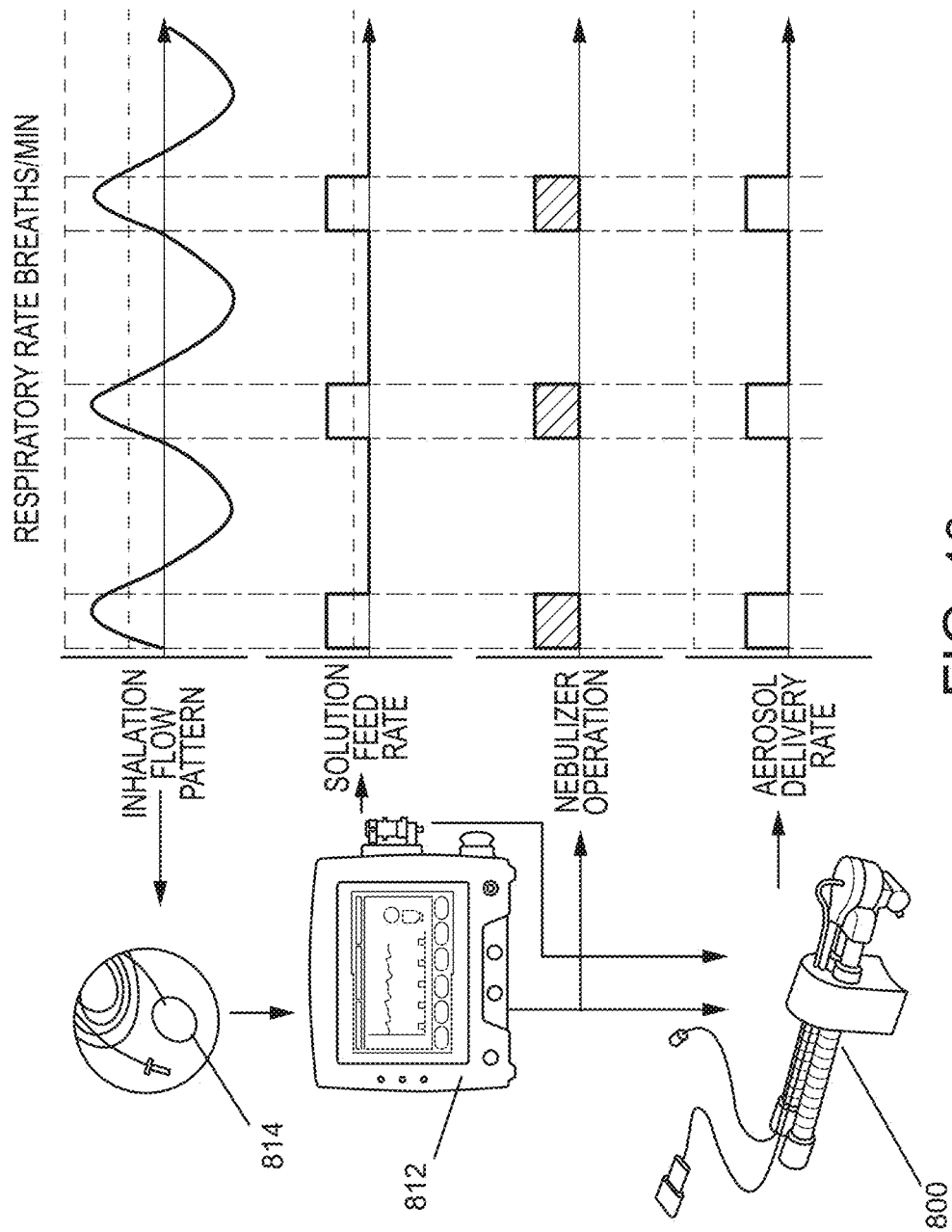
FIG. 13 illustrates functionality of the controller of FIG. 9.

FIG. 13 illustrates one example of the functionality of the controller 812. As shown in plot A, the controller 812 receives a signal from the respiration sensor 814 that indicates that the patient has begun an inhalation. The controller 812 then sends commands that initiate the delivery of a volume of medicament to the aerosol generator, which activates to aerosolize the liquid medicament as illustrated in plots B-D. In some embodiments, the controller 812 may be programmed to cause the aerosolization of medicament only for a first portion of an inhalation, allowing for a final portion of the inhalation to drawn in chase air to help deliver the aerosolized medicament into the deep lungs. For example, as shown in the various plots, the controller 812 causes the aerosolization of medicament only within the first 80% of each inhalation, allowing the final 20% of each inhalation to draw chase air into the patient's airways. It will be appreciated that other aerosolization patterns may be used. For example, the aerosolization of medicament may be done within the first 50%-90% (more commonly between 60%-80% and even more commonly between 70% and 80%) of each inhalation. Times greater than 80% are associated with more aerosol in the upper airway that is exhaled prior to reaching the lower airways. This allows the final 10%-50% (more commonly between about 20%-40% and even more commonly between 20% and 30%) of the inhalation to be used to draw chase air into the patient's airways.

Figure 14A:
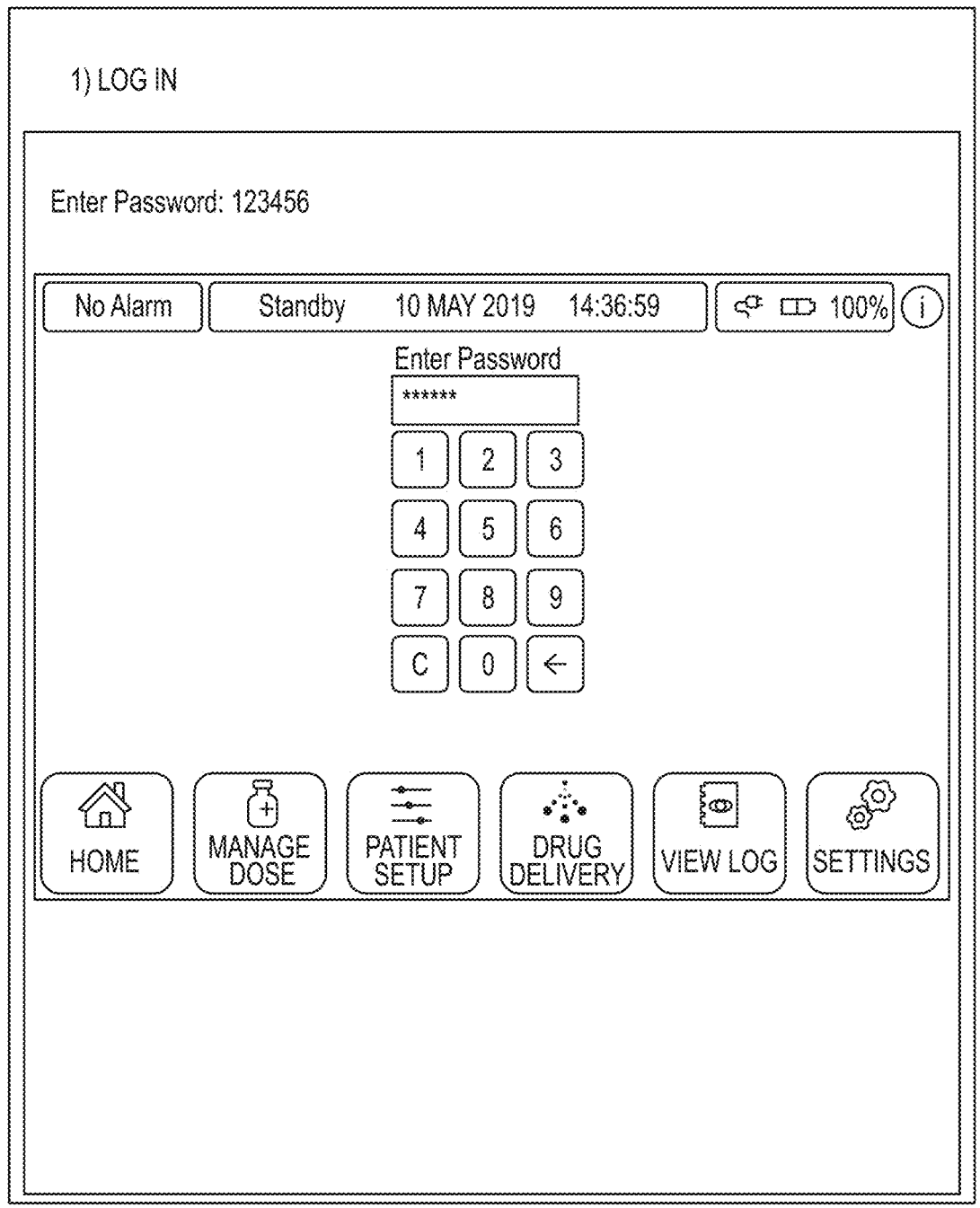

A set up process for using the aerosolization system of FIGS. 8-13 is illustrated in FIGS. 14A-14K. To start, the controller 812 may be powered on (such as by turning on a switch), allowing the controller 812 to begin a start-up sequence. In some embodiments, the start-up sequence may include a power-on self-test of the range of any audible alarms and/or the alarm display at the top of the controller cycling through the range of visual alarms. A backup alarm for the system may also be sounded as a test. As shown in FIG. 14A, a user (such as medical personnel) may need to log into the controller 812 using user interface 818. For example, the user may need to enter credentials, such as a user name, password, possession-based credential (such as a magnetic stripe card and/or a digital key or credential provided using a radio frequency communications protocol), biometric credential (fingerprint scan, facial scan, retinal scan, voice scan, and the like), etc. to begin using the aerosolization system. Once logged in, the user may need to provide patient information, which may be pertinent to the timing, volume, and/or other factors associated with treatment of the patient. For example, as illustrated in FIG. 14B, a user must enter a patient identifier (such as a name, identification number, etc.), a weight of the patient, a dosage type (high/low, etc.) and/or amount, and/or other details associated with the patient. After entering all necessary patient information, the user may be presented with a confirmation screen that allows the user to review and confirm the accuracy of the patient and dosing information prior to proceeding. If the patient and dosing information are correct, the user may confirm and continue with the set up process. If any of the patient or dosing information is incorrect, the user may re-input the incorrect information prior to proceeding.

Figure 14C:
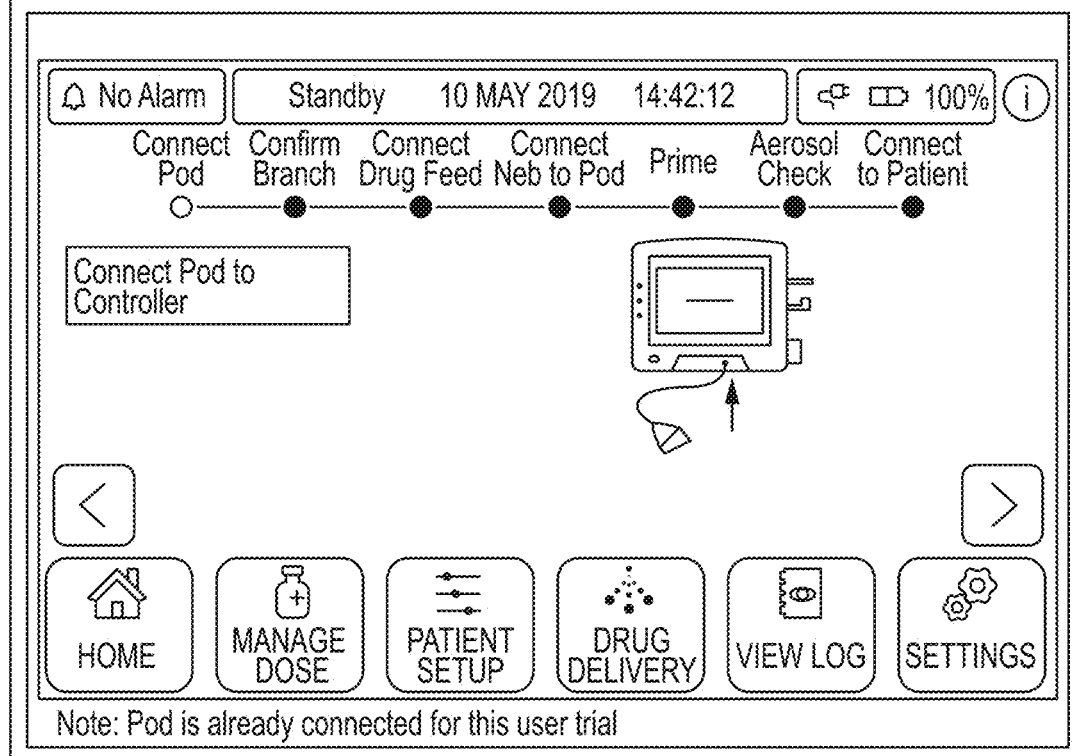

The user may then be presented with instructions on using the aerosolization system as shown in FIG. 14C. Here, the user interface 818 instructs the user to connect pod 810 to the controller 812 of the aerosolization system. For example, the user may insert a connector of the pod 810 into one of the ports 820 of the controller 812. In some embodiments, the user interface 818 may display a notification when the pod 810 is properly connected to the controller 812. In some embodiments, the controller 812 and/or a stand (not shown) on which the controller 812 may be affixed and/or otherwise supported may include a basket and/or other support structure that may be used to hold any excess cable from the pod 810. Other instructions may be presented that help a user set up the aerosolization system for use. As another example, in FIG. 14D the user interface 818 may instruct the user to connect respiration sensor 814 (such as a respiration sensor capsule) to both the pod 810 and to the patient and then confirm an inhalation of the patient. As illustrated, in some embodiments connecting the breath sensor to the pod includes inserting a connection, such as a slip luer, into a port of the pod 810. In the present embodiment, the respiration sensor 814 may be adhered and/or otherwise affixed to the patient's abdomen to begin sensing inspiration cycles. For example, the skin of the patient may be prepared using an adhesive barrier wipe and allowed to dry. The respiration sensor 814 may then be placed on the lateral and/or lower abdomen and taped in place, with tubing of the respiration sensor 814 being free of tape. The user interface 818 may prompt the user to confirm that a breath signal was received by the controller 812 and properly displayed on the user interface 818.

Figure 14E:
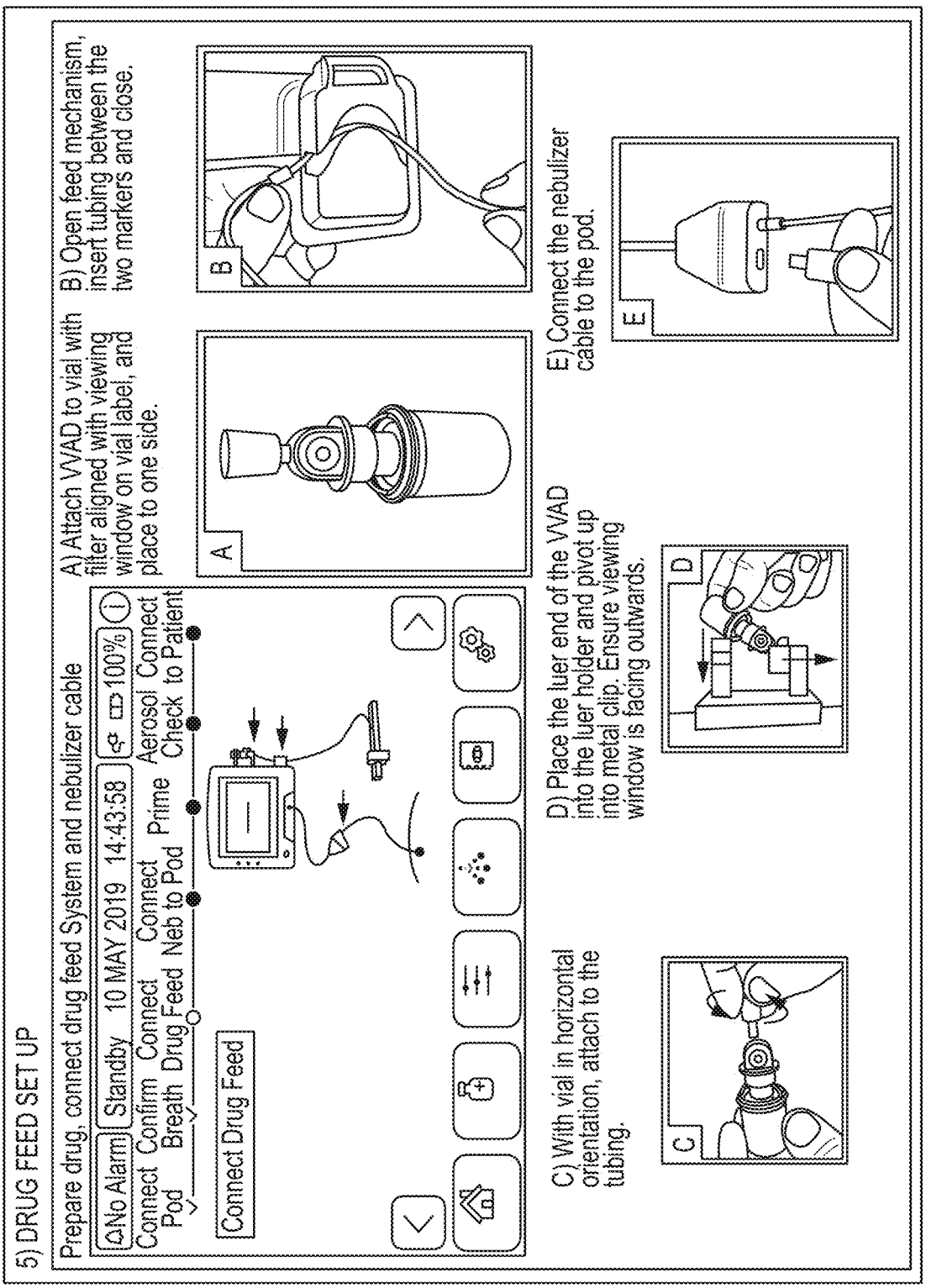

As shown in FIG. 14E, the user may be presented with instructions on how to set up the aerosolization system's drug feed line 806 and nebulizer cable 808. For example, the user may attach VVAD 828 to a vial of medicament (medication source 802), with filter 832 aligned with a viewing window on a label of the vial. This may be done by holding the vial upright and placing a piercer (not shown) of the VVAD 828 through a septum (not shown) of the vial until the VVAD 828 clicks and locks into place. A feed mechanism (such as a pump, not shown) may be opened, such as on a side of the housing of the controller 812, and fluid supply line 806 is inserted into the feed mechanism, which is then closed. The vial may be placed into a horizontal orientation and coupled with the fluid supply line 806. A luer end of the VVAD 828 may be placed into a luer holder portion of the holder 826 and pivoted up into a metal clip with a viewing window facing outwards. Nebulizer cable 808 may then be coupled with pod 810. The aerosolization device 800 may also be coupled with a respiration system, such as a ventilator. Once the various components are connected, the aerosolization device 800 may be primed.

Figure 14F:
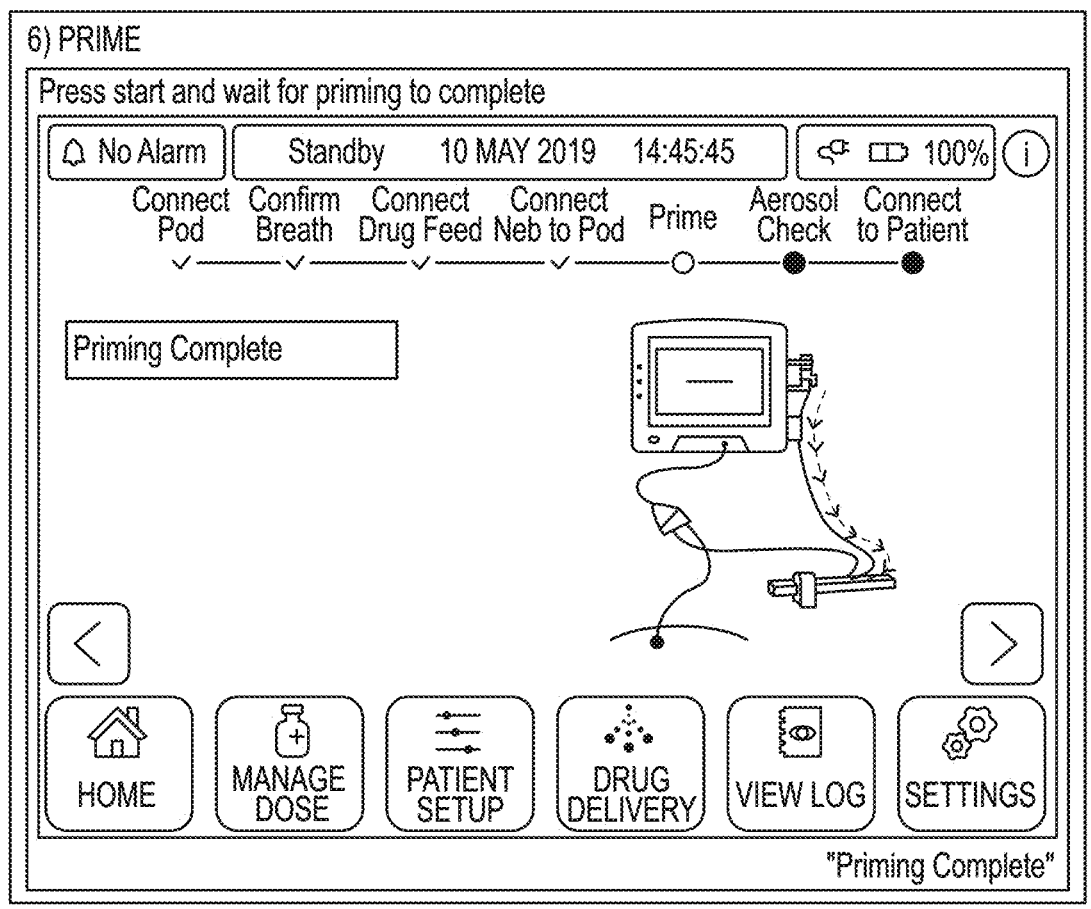
Figure 14G:
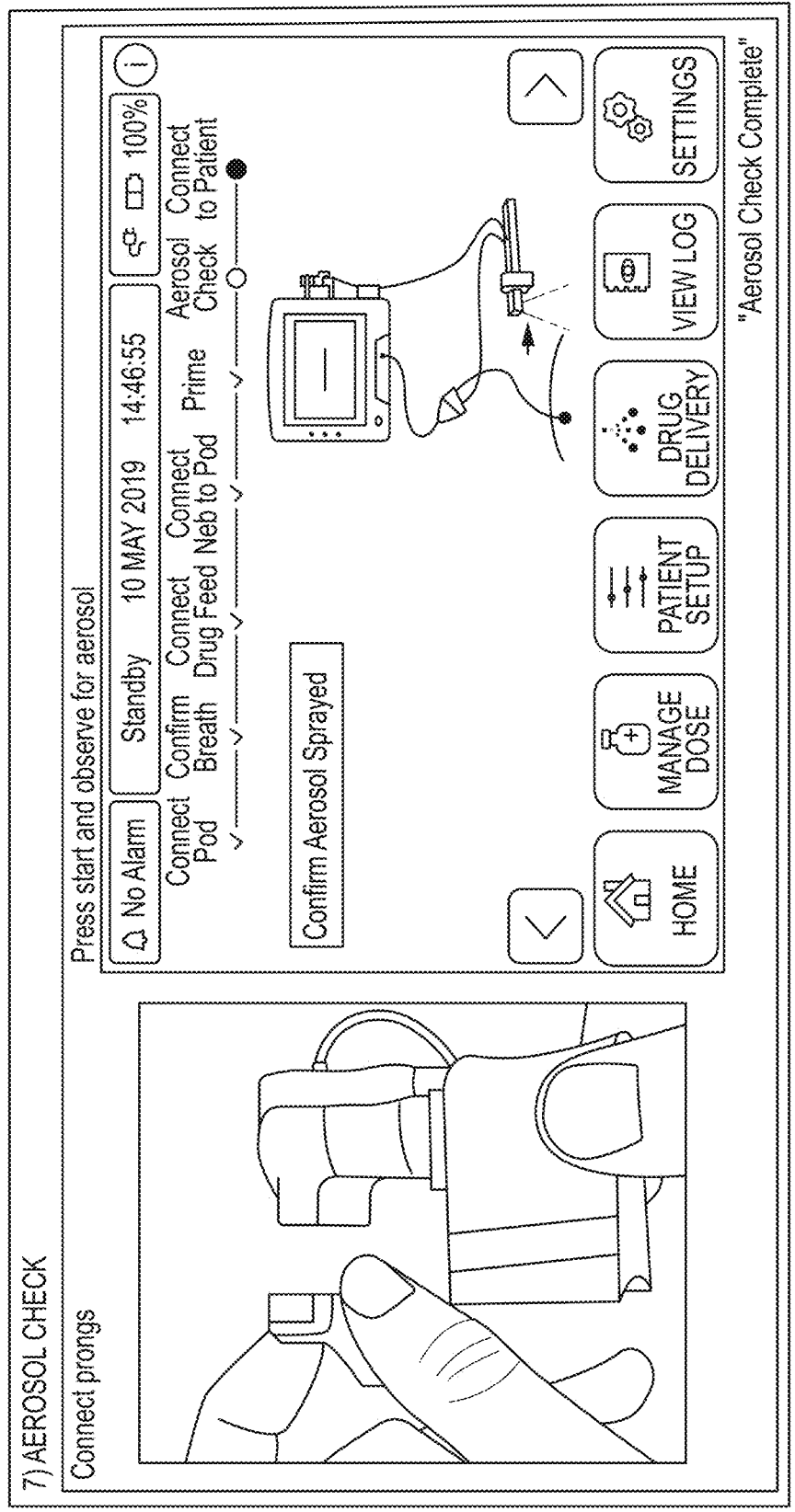
Figure 14H:
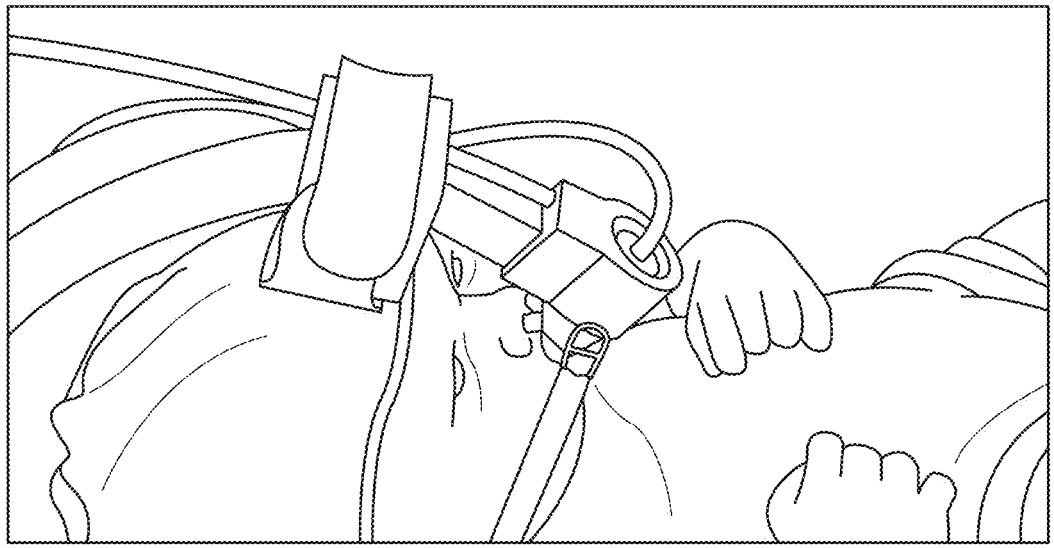
Figure 14I:
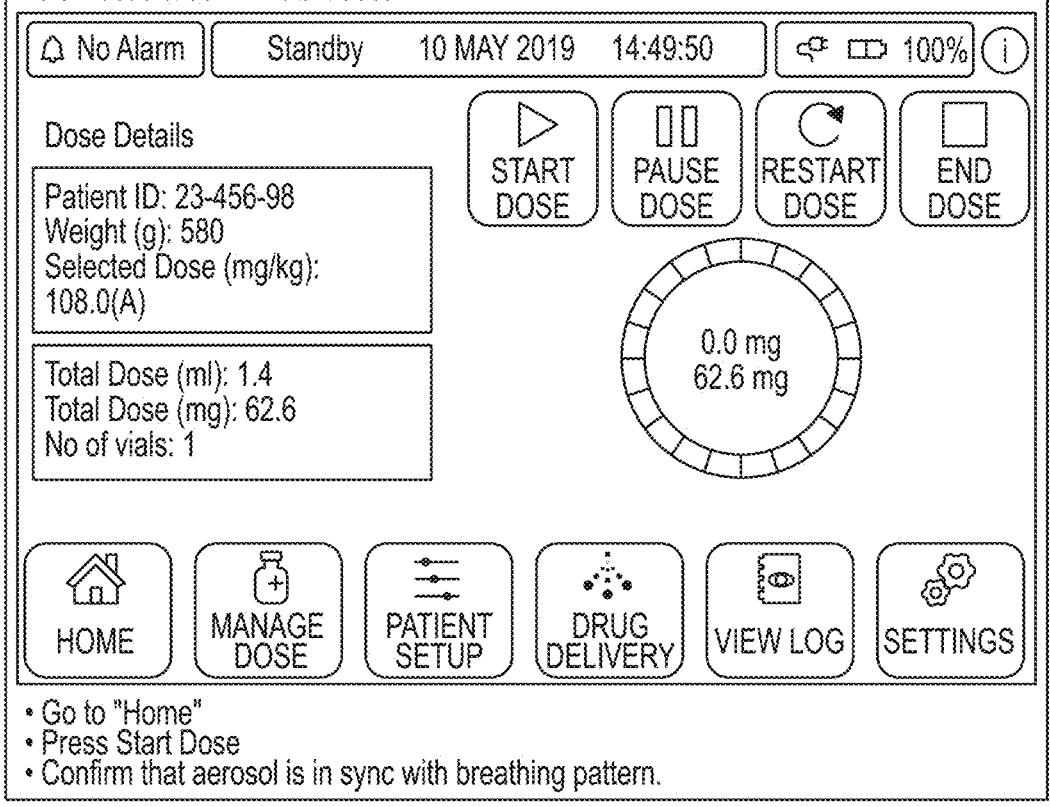

FIG. 14F demonstrates priming the pump. This may be done by selecting a prime function using the user interface 818 of the controller 812. Once primed, an aerosol check may be performed, as shown in FIG. 14G. The user may then interact with the user interface 818 to start the aerosol generation. The user may then observe for aerosol being produced and emitted from the patient interface (if affixed) or from an opening in the aerosolization device 800 to ensure that the aerosolization system is functioning properly. If aerosol is observed, the user may proceed with the set up. If aerosol is not observed, the user may repeat the priming and aerosol check steps. Before or after the aerosol check is completed, the user interface 818 may prompt the user to couple a patient interface (such as nasal prongs) with the aerosolization device 800. The user may select the proper size of patient interface and press the patient interface onto the aerosolization device 800. In some embodiments, the connection between the patient interface and the aerosolization device 800 may be trapezoidal. This shape may help the user properly align the patient interface in a correct orientation, although other shapes may be used. As shown in FIG. 14H, the aerosolization device 800 may be connected to an infant. For example, the nasal prongs (or other patient interface) may be interfaced with the infant's airways. In some embodiments, one or more straps and/or other restraints may be used to secure the aerosolization device 800 to the infant's airways and head to ensure that the aerosolization device stays in place if the infant moves. In some embodiments, the aerosolization device 800 may be secured to the infant's head using one or more straps that may be secured to a bonnet worn by the infant. Additionally, a foam pad may be affixed to the aerosolization device 800 that may extend between the aerosolization device 800 (spaced laterally apart from a portion of the aerosolization device 800 having the aerosol generator) and the infant's head. The foam pad may include multiple layers of peel able foam, allowing the layers to be peeled off and/or otherwise removed to adjust a distance between the aerosolization device 800 and the infant's head. Oftentimes, the foam pad may include a curved surface that is designed to match or substantially match a contour of the infant's head. Once in position, the foam pad (along with any straps) helps maintain the aerosolization device 800 at a proper position and orientation with the infant, regardless of the movement or orientation (back, side, stomach) of the infant. Once the aerosolization system is connected to the infant, the user may interact with the user interface 818 to begin dosing of the infant as shown in FIG. 14I. For example, the user may confirm the patient data and total dose, as well as verify that a number of vials of medication matches a Pharmacy Calculation and Dispensing Form from a pharmacist. Once the data is confirmed, the user may interact with the controller 812 to begin a dosing procedure. Once the dosing procedure is initiated, data such as breath cycles, dose indications, nebulization rate, remaining medication volume in the medication source 802, etc. The user interface 818 may also prompt the user to confirm that the aerosol is in sync with the infant's breathing pattern.

In some embodiments, when the vial is empty, the controller 812 halts the dosing. Oftentimes, when a threshold volume of medicament (such as less than 5%, 10%, 15%, 20%, etc.) remains in the vial, a low priority alarm may activate. After a set period of time, if the low priority alarm is not acknowledged by the user, a medium priority alarm will activate and "Vial Alert" may be displayed on user interface 818 and/or produced at one of the indicators 820. In some embodiments, when the vial is empty, the controller 812 auto pauses, and a medium alarm is activated. If after a predetermined time, the user has not acknowledged the alarm, a high priority alarm is activated. The user may be prompted to "Replace vial, restart dose from drug delivery screen". A new vial of medicament may be swapped in for the empty vial and dosing may continue. Once the dosing is complete, the user may confirm the end of dosing and interact with the controller 812 to return to a normal CPAP or other respiration circuit.

In some embodiments, low priority alarms are visual only and annunciate only with text on user interface 818. In some embodiments, medium priority alarms have visual and audio components, incorporating an associated colored alarm display (such as yellow) with associated audio and text. In some embodiments, high priority alarms have visual and audio components, incorporating an associated colored display box (such as red) on the user interface 818 with text on the user interface 818. In some embodiments, alarms may be provided for one or more of the following non-limiting events: if respiration is not detected, if a valid breath sequence has not been detected (which may occur if a valid breath sequence has not been detected where a valid breath sequence consists of three consecutive valid breaths in which a valid breath is determined as an Inhalation period≥100 mSec duration, an invalid breath sequence consists of at least one invalid breath, and an invalid breath is determined as an Inhalation period <100 mSec duration), if the nebulizer cable is disconnected from the Pod during dosing, if no wet/dry events are detected (such as due to a kink in tubing that prevents the drug from getting to the aerosol generator, not nebulizing and all of the drug is coming out a vent hole, nebulizing with no drug coming out of the vent hole, nebulizing and also drug coming out of the vent hole), if a remaining volume in the vial is at or less than a threshold amount (including empty), if the pod cable is disconnected from the Pod during dosing, if the pod cable is disconnected from the pod when not dosing, if communication failure is detected with the pod, if a pod internal failure is detected, if a system error is detected, if the drug feed mechanism fails, if the mains is disconnected and is being operated in battery mode, if a battery is at or below a threshold level of charge (including empty), and/or if the power on a self-test fails.

Figure 15:
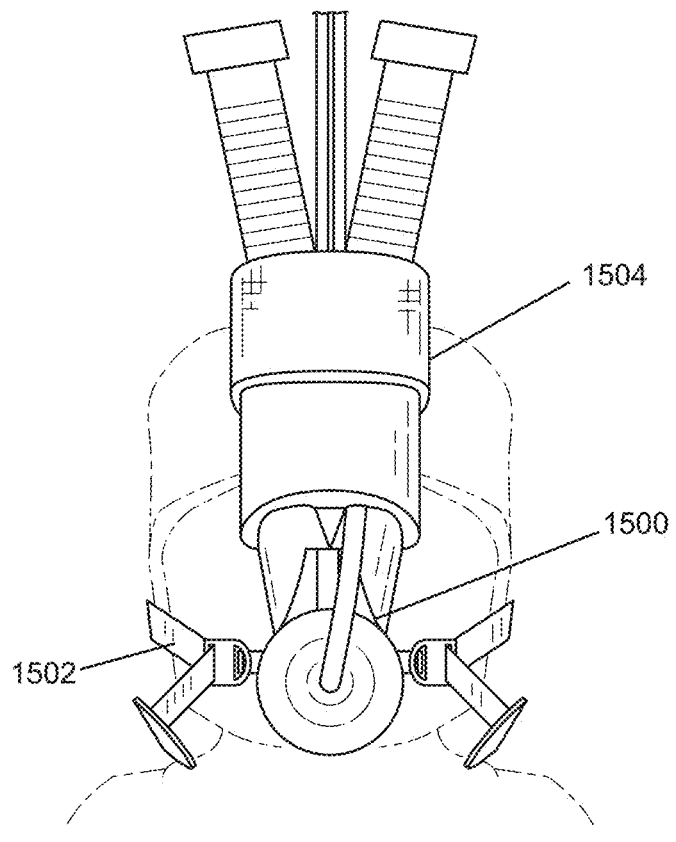
FIG. 15 illustrates an aerosolization device interfaced with an infant according to embodiments.

FIG. 15 illustrates an aerosolization device 1500 interfaced with an infant. Here, the aerosolization device 1500 may be similar to those described herein and places an aerosol generator proximal to the infant's airway and includes baffling that minimizes flow through the immediate patient aerosol generator/interface area during periods of aerosol generation. The aerosolization device 1500 may also include a PDAP mesh or similar mesh that enables aerosolization of particles having an MMAD of less than about 3 μm (more preferably less than about 2 μm) to be generated at high flow rates (between about 0.1 ml/min and 1.5 ml/min). The aerosolization device 1500 may also include a power/control port that allows one or more controllers (similar to controller 812) to be connected to supply power and/or operational commands to the aerosol generator.

The aerosolization device 1500 may also include one or more straps or other restraints 1502 that enable the aerosolization device 1500 to be secured with the infant's head and airways. Additionally, the aerosolization device 1500 may include a foam pad 1504 that is designed to help maintain the aerosolization device 1500 at a proper position and orientation with the infant, regardless of the movement or orientation (back, side, stomach) of the infant The foam pad 1504 may include multiple layers of peel able foam, allowing the layers to be peeled off and/or otherwise removed to adjust a distance between the aerosolization device 1500 and the infant's head. Oftentimes, the foam pad 1504 may include a curved surface that is designed to match or substantially match a contour of the infant's head. The aerosolization device 1500 may be constructed of sufficiently light materials (such as medical-grade plastic foam) that allow the infant to move around without causing the aerosolization device 1500 to shift out of proper position.

Figure 16:
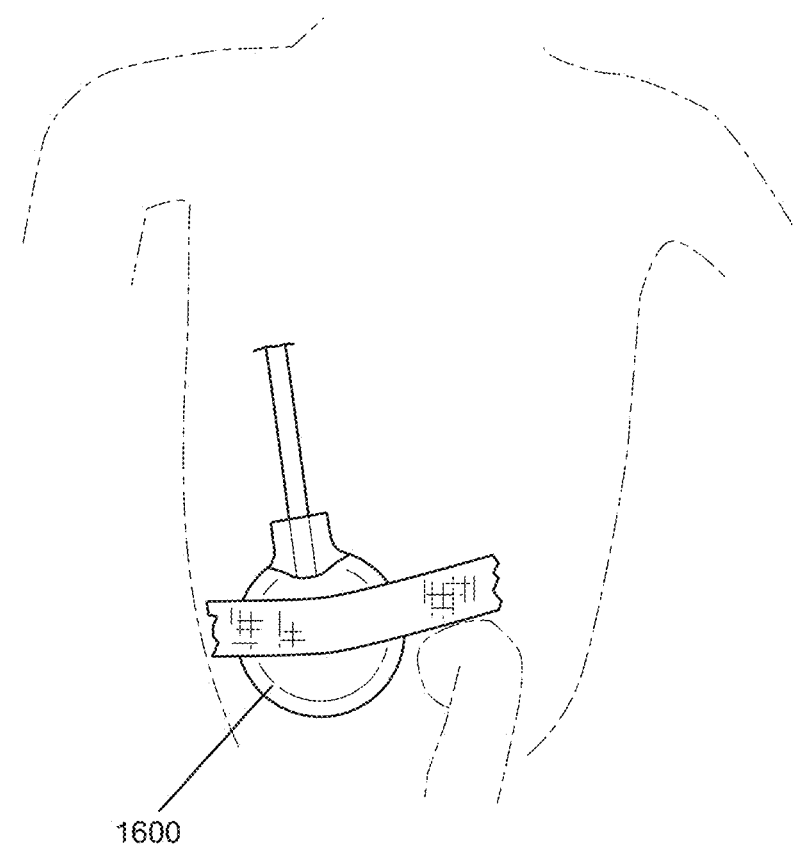
FIG. 16 illustrates a respiration sensor capsule interfaced with an infant's abdomen.

FIG. 16 illustrates a respiration sensor capsule 1600 (similar to respiration sensor 814) interfaced with an infant's abdomen. As shown, the respiration sensor capsule 1600 is taped and/or otherwise adhered to the infant's abdomen and is then used to detect the beginning and/or end of the infant's inspiration cycles. This is done using changes in the volume of the sensor capsule 1600 in response to movement of the abdomen that is associated with breathing. Using data from one or more inspiration cycles, a controller (not shown) may monitor flows entering and leaving the capsule associated with volume changes in the abdominal sensor and synchronize delivery of aerosolized surfactant with the infant's inhalation to help maximize delivery efficiency of the surfactant.

Figure 17:
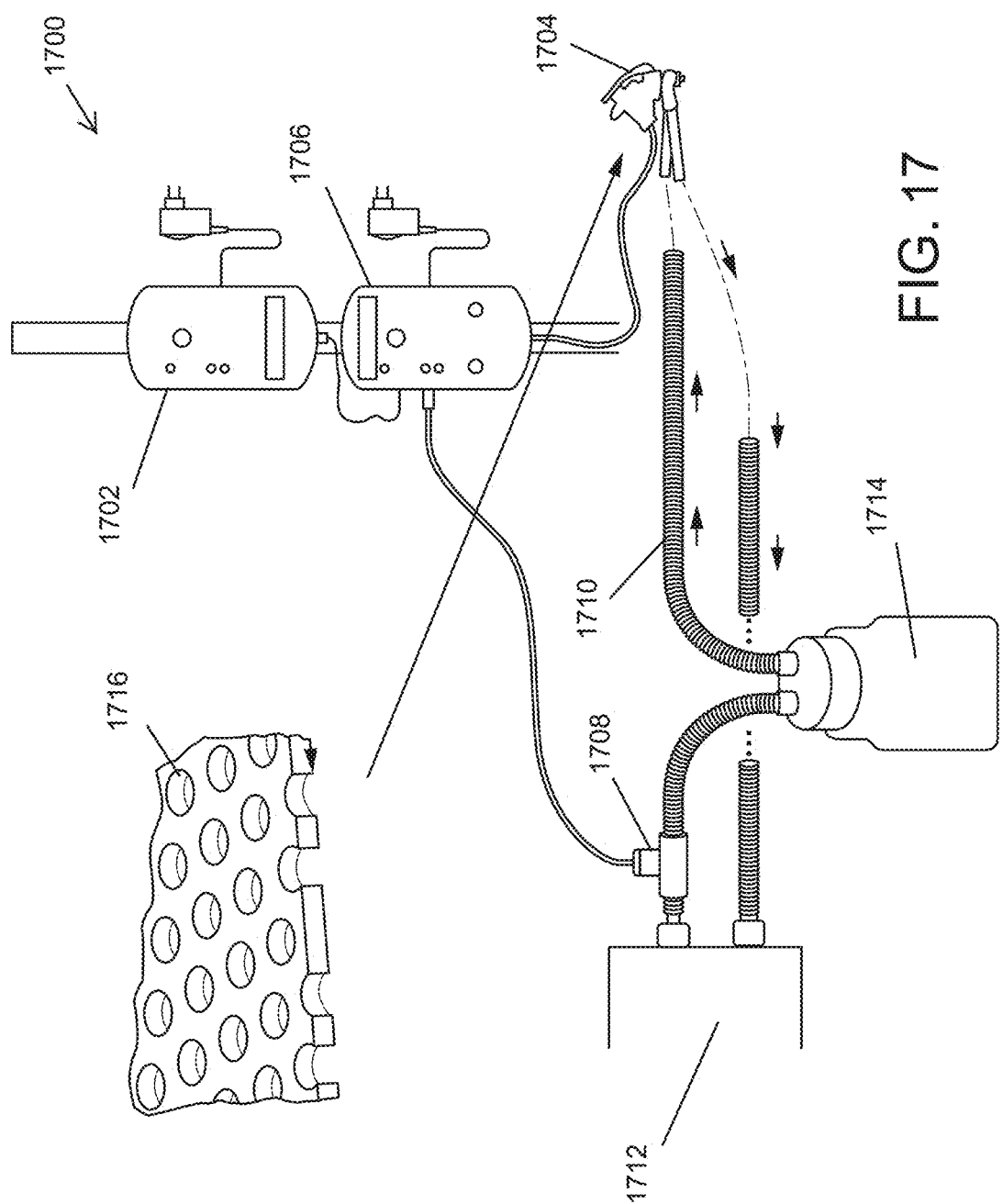
FIG. 17 an aerosolization system for delivering surfactants to an infant according to embodiments.

FIG. 17 illustrates another embodiment of an aerosolization system 1700 for delivering surfactants to an infant in an effective and efficient manner. As illustrated, a controller 1702 (which may be similar to controller 812) is used to provide power and control to an aerosolization device 1704. The controller 1702 may also be configured to control a delivery mode of the aerosolization device 1704. For example, the controller 1702 may be configured to alternate between a timed mode in which a treatment is given over a set period of time, or a continuous mode in mode the delivery of aerosolized surfactant is done indefinitely based on the infant's inhalation patterns. System 1700 may also include an additional controller 1706 that allows medical personal to set aerosol delivery criteria. For example, the additional controller 1706 may enable a flow rate that triggers delivery of aerosol, an inspiratory time for delivery of aerosol, and/or other criteria that control the timing, dosage, and/or duration of the aerosolized dosage. While described with controller 1702 and additional controller 1206 being different components, it will be appreciated that in some embodiments a single controller (or more controllers) may be used to control the operation of system 1700.

System 1700 may also include one or more flow sensors and/or other breath sensors 1708. As illustrated, flow sensor 1708 may be coupled with an inspiratory limb 1710 of a respiration system 1712, such as before and/or after an optional humidifier 1714. The breath sensor 1708 may be sued to detect an inhalation of the infant. In other embodiments, the breath sensor 1708 may be a respiration sensor capsule that is interfaced with the infant's abdomen. The breath sensor 1708 may be electronically coupled with one or both of the controllers 1702 or 1706 such that the inhalation data may be used to trigger activation of the aerosolization device 1704 (which may be similar to any of the aerosolization devices described herein). The controllers 1702 and 1706 may be electronically coupled with the aerosolization device 1704 to provide both power and operating commands to the aerosolization device 1704. In some embodiments, the aerosolization device 1704 may include a PDAP mesh 1716 that produces aerosolized surfactant having a MMAD of less than about 3 µm (preferably less than about 2 µm) at a rate of at least 0.1 ml/min. Such aerosolization devices 1704, when used in conjunction with controllers 1702, 1706 and breath sensors 1708, allow for 1) the generation and delivery sufficiently small aerosol particles, 2) breath synchronized aerosol delivery, and 3) placement of the aerosol generator proximal to the infant's airway with baffling of continuous gas flow to minimize flow through the immediate patient aerosol generator/interface area during periods of aerosol generation (as best illustrated in FIGS. 6-6D), thereby enabling vastly improved delivery efficiency rates to the lungs of between about 25%-60%, and more commonly between about 40%-60%.

Figure 18:
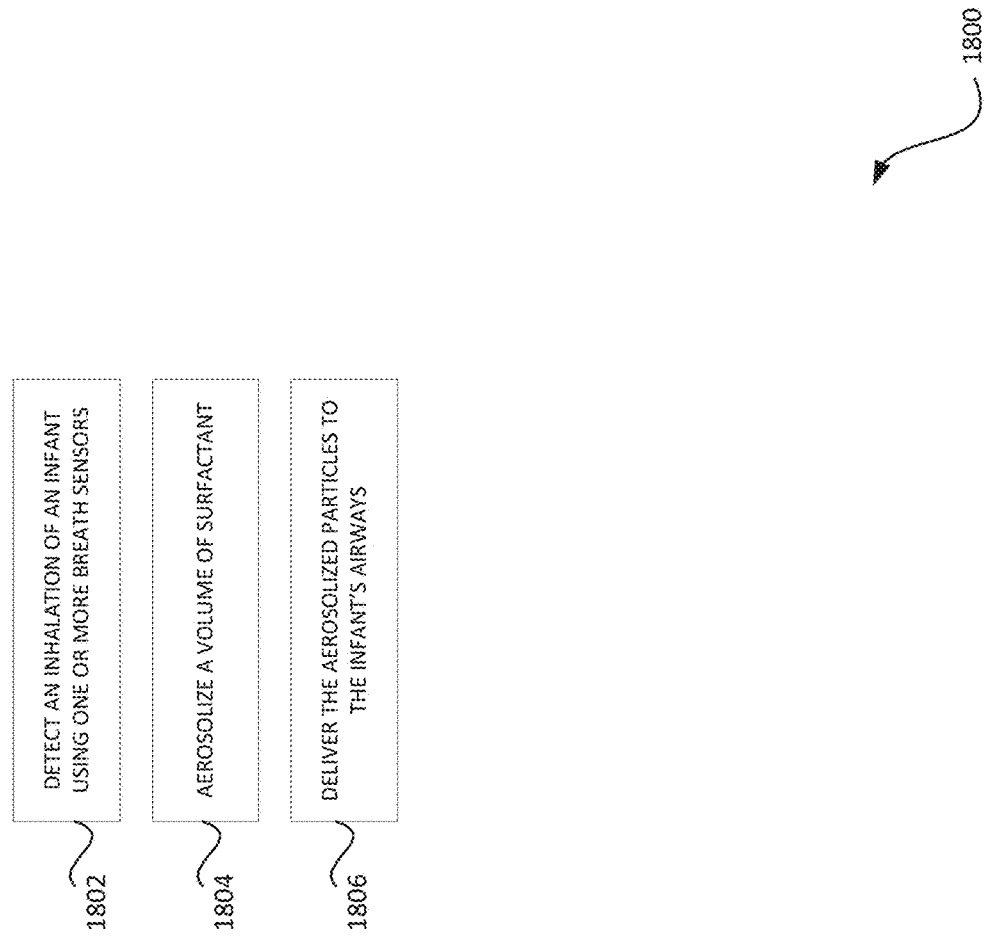
FIG. 18 is a flowchart of a process of delivering aerosolized medicament to a patient.

FIG. 18 is a flowchart of a process 1800 for delivering aerosolized surfactant to an infant. Process 1800 may be performed using any of the aerosolization devices, processors, and/or respiration sensors described herein. Process 1800 may begin at block 1802 by detecting an inhalation of an infant using one or more breath sensors. For example, a breath sensor may be affixed to the abdomen of the infant. The breath sensor may detect the expansion of the infant's abdomen that is associated with an inhalation. Based on this detected inhalation, a controller may cause an aerosolization device to aerosolize a volume of surfactant into particles having a mass mean aerodynamic diameter (MMAD) of less than about 3 µm at a rate of at least 0.1 ml/min at block 1804. The surfactant may be aerosolized within about 1 to 8 cm from a patient interface. In some embodiments, aerosolizing the volume of the surfactant may include delivering the volume of the surfactant from a reservoir to a mesh of the aerosol device and vibrating the mesh to aerosolize the volume of the surfactant. In some embodiments, the volume of the surfactant is delivered from the reservoir to the mesh via a conduit having a distalmost tip with a diameter. The distalmost tip of the conduit may be positioned at a distance from a mesh of the aerosol generator that is less than or equal to the diameter. This ensures that any medicament ejected from the tip contacts and wicks along a surface of the mesh, enabling the aerosolization device to effectively operate at any orientation. In some embodiments, aerosolizing the volume of the surfactant involves aerosolizing a portion of the volume of surfactant within at least a portion of a first 80% of each of a successive number of inhalations such that chase air is provided within at least a portion of a final 20% of each of the successive number of inhalations. At block 1806, the aerosolized surfactant may be delivered to the infant's airway via a patient interface, such as nasal prongs.

In some embodiments, the process 1800 may also include coupling the aerosolization device with a respiration system and diverting a portion of airflow from the respiration system into a chamber of the aerosolization device via at least one airway. The chamber is configured to mix the portion of the airflow with aerosolized surfactant. In some embodiments, the portion of airflow is respiratory flow and is less than an amount of air that continues to an expiratory limb of the respiration system. In some embodiments, the portion of airflow is diverted using at least one baffle that defines the at least one airway. The at least one baffle may be configured to divert the portion of airflow into the aerosol chamber via the at least one airway and to divert an additional portion of airflow from the inspiratory limb to the expiratory limb. In some embodiments, two baffles are used. A first baffle may define a first airway and a second baffle may defines a second airway. The first airway is provided at a lateral end of the first baffle and the second airway is provided beyond a distal edge of the second baffle, with the lateral end and the distal edge extending in different directions such that the respiratory flow moves in multiple directions to pass the first baffle and the second baffle.

Figure 19:
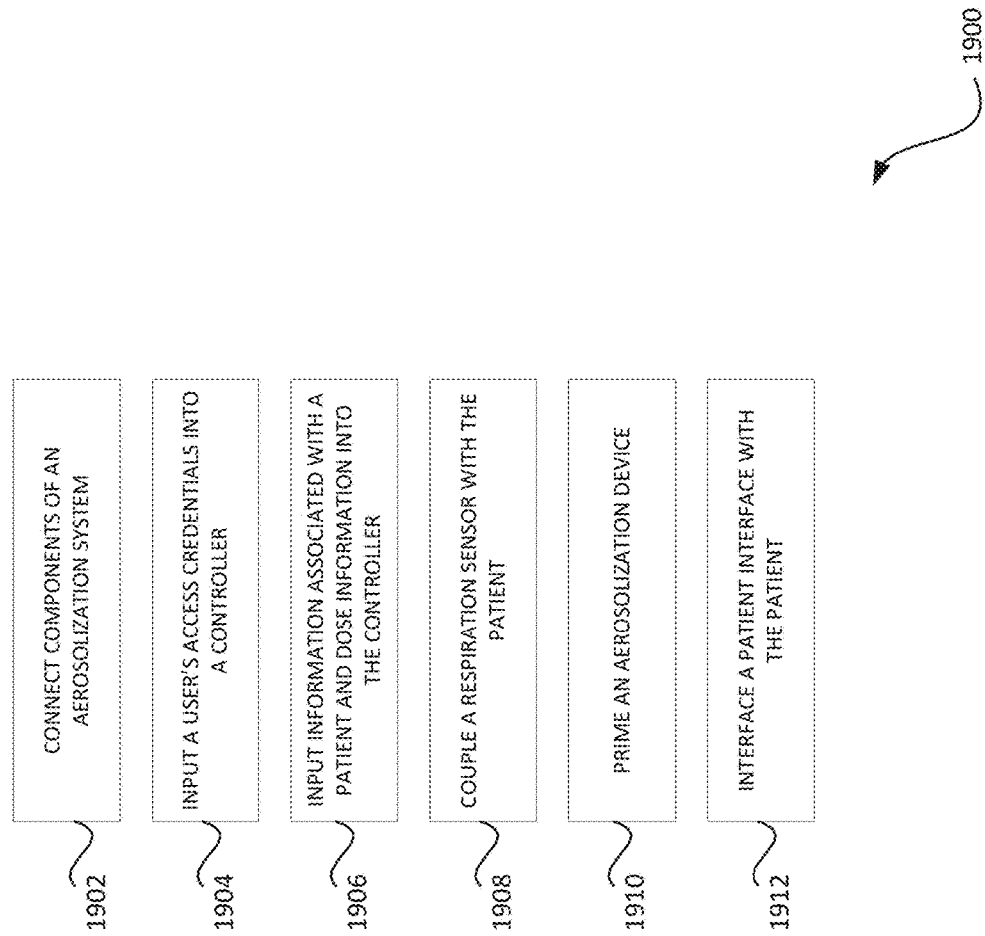
FIG. 19 is a flowchart of a process of initializing an aerosolization system.

FIG. 19 is a flowchart of a process 1900 for initializing an aerosolization system. Process 1900 may be performed using any of the aerosolization devices, processors, and/or respiration sensors described herein. Process 1900 may begin at block 1902 by connecting an aerosolization device with a controller, a respiration sensor, a medication source, and a respiration system. This may involve coupling a nebulizer cable between the aerosolization device and the controller (possibly via a pod or other adaptor), coupling an inspiratory limb of the respiration system with an inlet of the aerosolization device, coupling an expiratory limb of the respiration system with an outlet of the aerosolization device, coupling a cable of the respiration sensor with the controller (possibly via a pod or other adaptor), and/or coupling the aerosolization device with the medication source. In some embodiments, coupling the aerosolization device with the medication source may include coupling a fluid supply line between the medication source and the aerosolization device. In some embodiments, the medication source is a vented vial access device (VVAD) that is coupled with the fluid supply line.

At block 1904, a user's access credentials are input into the controller, ensuring that only authorized users have access to the aerosolization system and the ability to administer medicament. The access credential may include one or more of a user identifier, a password, a possession-based credential, and a biometric credential. Information associated with a patient and dose information may be input into the controller at block 1906. This may include information such as a patient identifier, a weight of the patient, a dosage level, and the like. At block 1908, the respiration sensor may be coupled with a patient. This may involve adhering the sensor to the patient's abdomen. In some embodiments, a detection of breath may be configured after coupling the respiration sensor with the patient. At block 1910, the aerosolization device may be primed. This may include aerosolizing a portion of medicament prior to interfacing the patient interface with the patient's airways to ensure the device is functioning properly. At block 1912, the aerosolization device may be interfaced with the patient's airways. For example, nasal prongs may be inserted into the nostrils of the infant. In some embodiments, the patient interface may need to be secured to the aerosolization device prior to interfacing the device with the patient. In some embodiments, one or more straps and/or foam pads may be positioned and/or secured about the infant to secure the aerosolization device in place. Once secured in place, a user may initiate delivery of a dosage to the infant and/or may review a user interface of the controller to confirm that delivery of aerosolized doses are in sync with the infant's inhalations.

In some embodiments, the process 1900 may also include performing a start-up sequence upon powering on the controller. The start-up sequence may cycle through a number of audio alarms, visual alarms, or both audio and video alarms to ensure the controller is functioning properly prior to use.

EXAMPLES

Figure 20:
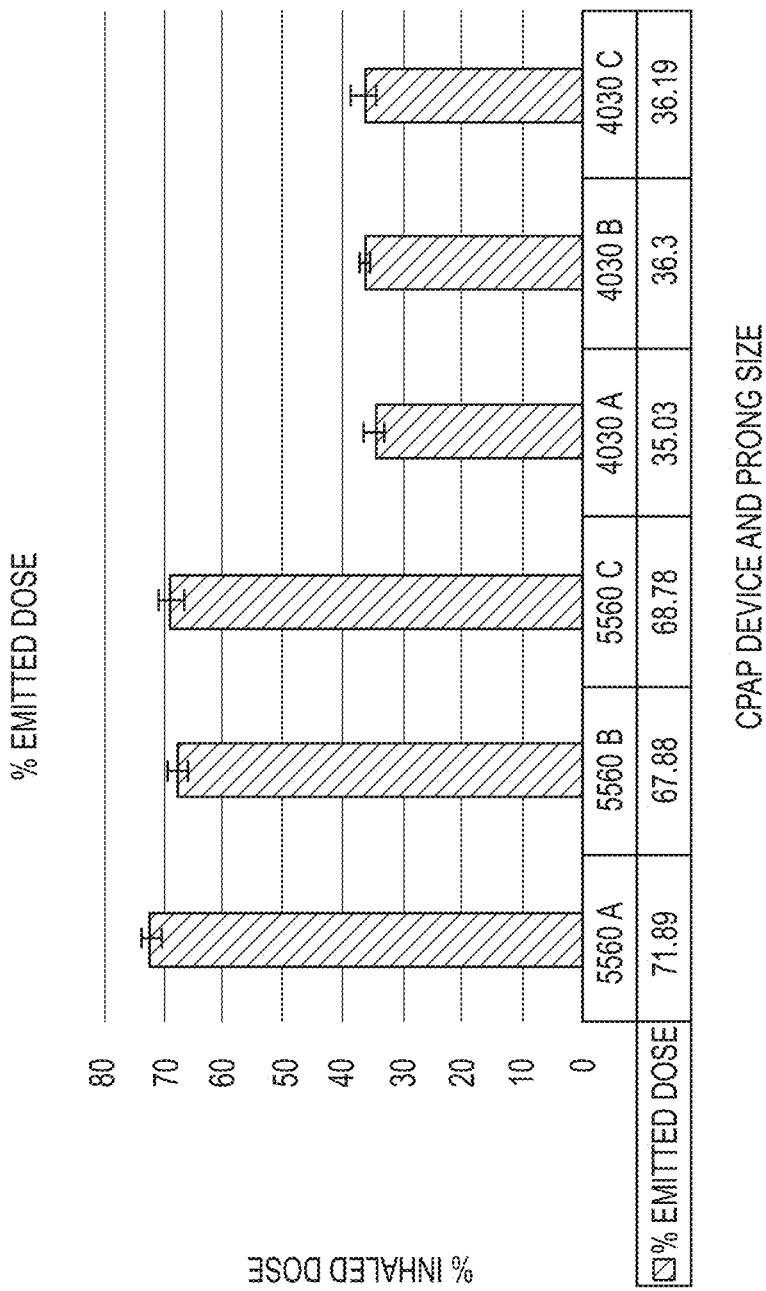
FIG. 20 is a bar graph illustrating emitted dose rates using an aerosolization system according to embodiments.

In vitro experiments were conducted to determine the effective emitted dose of medicament using an aerosolization device in accordance with the present invention. Simulated infant inhalations were performed using a modified Harvard Apparatus sinusoidal small animal ventilator and an Ingmar Lung Simulator interfaced with a patient adaptor (here in the form of nasal prongs) of an aerosolization device similar to that described in FIGS. 6-6D. Simulations were performed using two different sizes of nasal prongs, with a larger nasal prong (5560) and a smaller nasal prong (4030). As seen in the bar graph illustrated in FIG. 20, the larger the prong size, the higher the emitted dose. Notably, the larger nasal prong (5560) resulted in emitted doses of between 68% and 72% emitted dose while the smaller nasal prong (4030) resulted in emitted doses of between about 35% and 37%.

Figure 21:
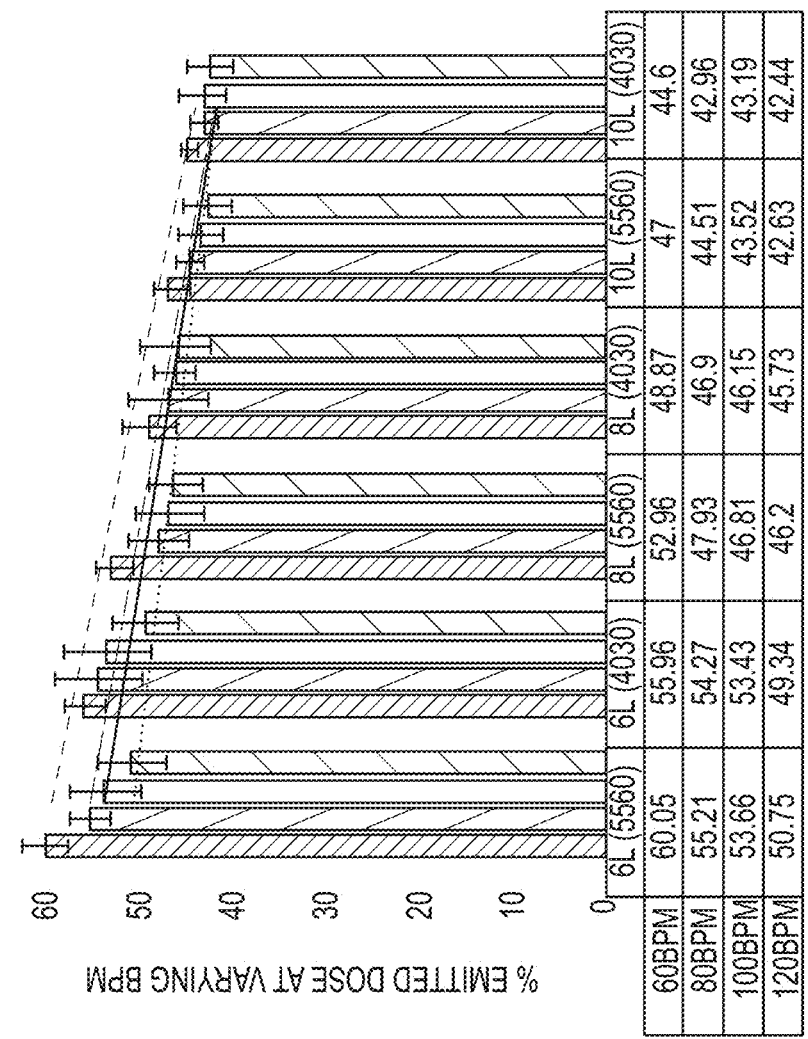
FIG. 21 is a bar graph illustrating emitted dose rates as a function of breathing rate and flow rate using an aerosolization system according to embodiments.

The air flow was then set to 6 liters per minute (LPM), 8 LPM, and 10 LPM and with breathing rates of 60 breaths per minute (BPM), 80 BPM, 100 BPM, and 120 BPM. Emitted dose rates were then measured at each combination of air flow rate and breathing rate. As illustrated in FIG. 21, gas flow has an effect on delivery efficiency, with greater flow rates leading to slightly lower delivery efficiencies. For example, at lower flow rates (6 LPM), the larger nasal prongs (5560) resulted in approximately 50% to about 60% emitted dose at the extreme ends of the tested breathing rates, while at higher flow rates (10 LPM) the emitted dose ranged from about 42% to about 47%. It is noted that as the breathing rates increased, the difference in efficiency associated with greater flow rates becomes less pronounced. For example, the range of emitted dose rates at 60 BPM was about 44% to about 60%, while at 120 BPM the emitted dose rates ranged from about 42% to about 51%. Based on these results, it was determined that the aerosol generators described herein enables consistent inhaled dose of medicament across a clinically relevant range of respiratory rates (60-120 BPM) and CPAP flows (6-10 LPM) commonly used with bubble and vent CPAP systems.

Embodiments of the present invention also provide systems and methods for delivering surfactants (or other medicaments) to infants, particularly preterm infants, in a non-invasive manner. In order to achieve effective and efficient administration of medical aerosols to preterm infants, a combination of attributes is required: 1) sufficiently small aerosol particles, 2) breath synchronized aerosol delivery, and 3) placement of the aerosol generator proximal to the infant's airway (within about 1-8 cm) with baffling of continuous gas flow to minimize flow through the immediate patient aerosol generator/interface area during periods of aerosol generation. By satisfying these conditions, surfactant delivery rates exceeding 40% and up to about 60% are achievable, which provide significant improvements over conventional efficiency rates of less than 10%.

Figure 23:
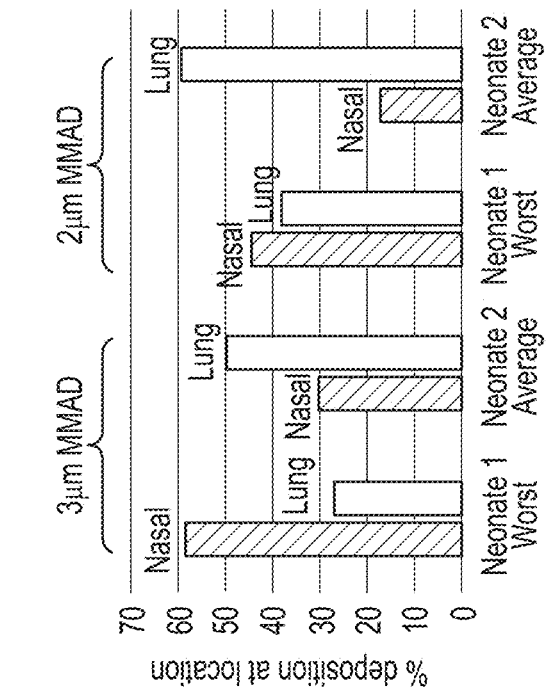
FIG. 23 is a graph illustrating deposition rates vs. particle size.
Figure 22:
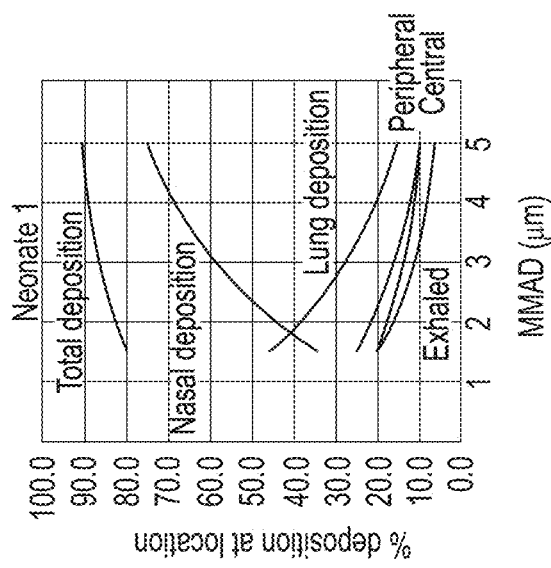
FIG. 22 is a graph illustrating deposition rates vs. particle size.
Figure 25:
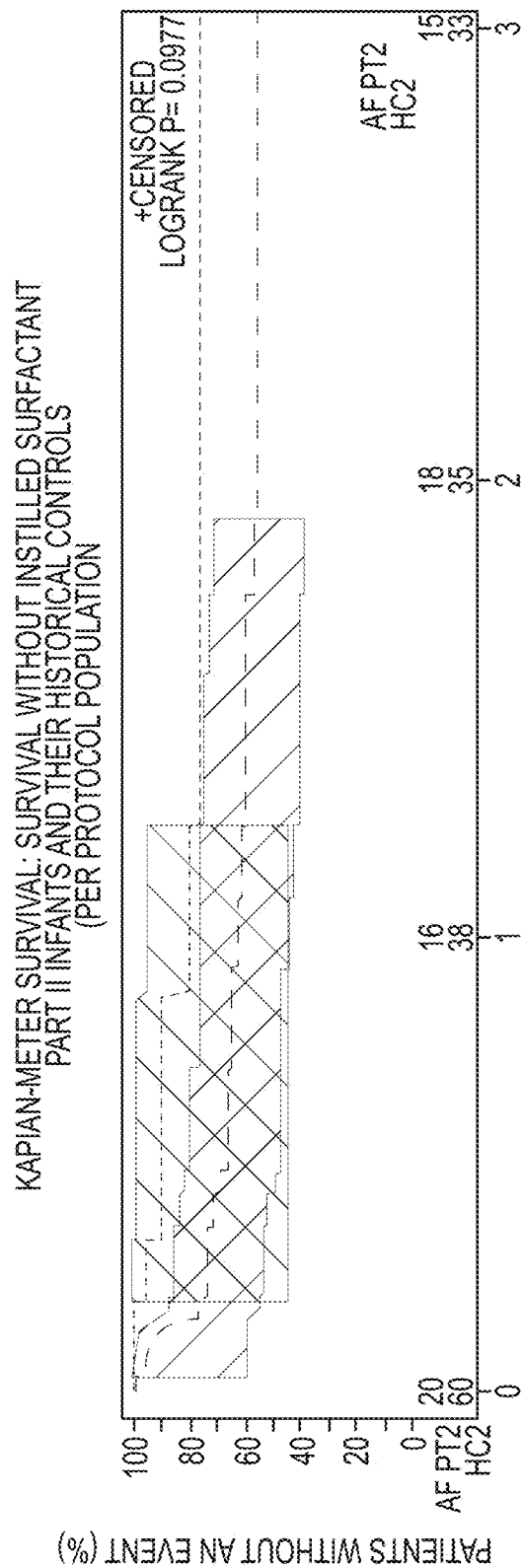
FIG. 25 is a graph showing survival rates without instilled surfactant according to a study.

Due to the breathing physiology of preterm infants, in order to properly delivery aerosolized surfactant to an infant in a non-invasive it is necessary to utilize nasal delivery techniques, such as nasal prongs that are insertable within the nasal passages of the infant. Using such delivery techniques, it is desirable to deliver aerosol particles that are less than about 2 µm, as particles larger than this are typically impacted out in the interface of the aerosolization device and/or in the airways prior to being dispersed in the infant's lungs. This is shown in FIGS. 22 and 23, which demonstrate particle deposition rates for various particle sizes (using MMAD and a GSD of 2.2) for neonates, with neonate 1 being 4 months old and neonate 2 being preterm 28 weeks. FIG. 22 illustrates that as particle size decreases the lung deposition increased (FIG. 22 only shows results for neonate 1), with lung deposition surpassing 40% as particle sizes fall below 2 µm. Notably, for particles larger than 2 µm the nasal deposition is typically between about 50%-70%, which represents particles that are not delivered to the infant's lungs. FIG. 23 illustrates lung vs. nasal deposition rates for both neonates using a 3 µm MMAD and a 2 µm MMAD aerosol. Here, for both neonates improved lung deposition is observed for the aerosol of 2 µm MMAD, with deposition rates being just under 40% for neonate 1 and just under 60% for neonate 2. These results demonstrate the need for smaller aerosol particles in order to maximize delivery efficiency.

Conventional nasal delivery techniques typically utilize particles having a 4-7 µm MMAD, with a geometric standard deviation of approximately 2.0 or higher. This is due to the viscous nature of most surfactants, which makes it very difficult to aerosolize undiluted surfactant into particles of sufficiently small sizes at sufficiently high aerosolization rates to be effective using conventional jet nebulizers, specialty jet nebulizers, mesh nebulizers, heated capillary generators, and the like. As such conventional delivery techniques see impaction rates that reduce the available mass of aerosol in a given dose by up to 80%. Only 40-60% of the remaining aerosol (that portion made up of particles having less than about 2 µm) would then reach the lower airways of the lungs, resulting in a total efficiency rate of approximately 10% of the initial emitted dose from the aerosol generator.

Embodiments of the present invention provide systems and methods that generate sufficiently small aerosol particles using aerosolization devices such as those described in relation to FIGS. 1-8 above. In particular, embodiments utilize aerosolization devices that include aerosol generators that leverage the capabilities of a PDAP mesh (such as disclosed in U.S. Patent Publication No. 2016/0130715, previously incorporated by reference) to consistently generate aerosolized surfactant having less than about 3 µm (and more preferably, a range of about 1.5 µm to about 2.5 µm)

at output rates of between about 0.1 ml/min and 0.6 ml/min. By leveraging the capabilities of such aerosol generators, embodiment of the present invention are able to provide sufficiently small particle sizes for effective and efficient delivery of surfactant to the lungs. For example, even with an aerosol having an MMAD of less than 3 µm achieves a trans-nasal pulmonary efficiency of about 40-60% of the nominal dose of surfactant.

As noted above, to fully maximize delivery efficiency, it is also useful to synchronize the aerosol delivery with the infant's inhalations. This helps ensure that surfactant is not wasted when aerosolized during exhalation and/or periods between breaths. For example, infants typically have inspiratory:expiratory ratios ranging from about 1:1 to about 1:3. Accordingly, aerosolized surfactant is typically only inhaled for about 25-50% of the time. In conventional systems, this aerosol is typically carried by a gas flow of between about 6-10 LPM with a bubble CPAP, which exceeds the infant's peak inspiratory flows and results in wasting up to half the aerosolized medicament.

Embodiments of the invention may tie the activation of the aerosol generator to the infant's breath. As described above, this may be done using one or more breath and/or flow sensors to tracking the patient's breathing pattern and/or a ventilation cycle. A controller then uses this information to predict when subsequent inhalations will begin and times delivery of fluid from the fluid source to the aerosol generator and/or activation of the aerosol generator to be approximately synchronized with the infant's inhalation. In some embodiments, the detection of inhalations may be done using a respiration sensor capsule attached to the infant's abdomen. The respiration sensor capsule may detect movement of the abdomen associated with inhalations, which typically occurs just before the inhalation itself occurs, making the respiration sensor capsule particularly useful in determining inhalation timing for synchronization of aerosol generation.

The effectiveness of the respiration sensor capsule in detecting inhalations is demonstrated in FIG. 24. Here, separate flow sensors were interfaced with an infant's airway and a respiration sensor capsule secured to the infant's abdomen. The infant weighed 1,500 g and had a respiratory rate of 70 BPM. The plot in FIG. 24 shows that the sensor signal from the respiration sensor capsule detected each inhalation and exhalation that was detected by the flow sensor, with the respiration sensor capsule detecting the beginning of the inhalation slightly before the flow sensor, which enables time for the controller to activate the aerosol generator. These results confirm that the use of a respiration sensor capsule may be particularly useful for synchronizing breaths and aerosol generation. FIG. 24 also demonstrates that this particular set of inhalations was over a period of 5 seconds, with inhalations only taking up approximately ⅓ of the time period. Thus, without synchronizing breath and aerosol delivery, over ⅔ of the dose of aerosolized surface would be wasted.

In some embodiments, the aerosolization devices described herein include an aerosol generator capable of coupling to a variety of artificial respiration systems. The aerosol generator may receive liquid medicament from a fluid source through a fluid delivery conduit. In operation, fluid from the fluid source is advanced with a pump through the fluid delivery conduit to the aerosol generator where the fluid is aerosolized before and/or while the patient inhales. In some embodiments, the fluid delivery conduit may be primed with fluid before treatment to ensure rapid delivery (e.g., preloading fluid in aerosol generator). The pump may controlled with a controller, which times delivery and dosage of the fluid.

The controller includes one or more processors that execute instructions stored on one or more memory to drive operation of the pump and the aerosol generator. For example, the memory may include instructions that indicate the amount of fluid to be pumped to the aerosol generator in each dose for each actuation of the aerosol generator, how much fluid is to be pumped over a specific period of time or times, etc. The stored instructions may be based on a size of the patient, age of the patient, sex of the patient, type of medicament, fluid additives, desired amount of aerosol, etc. The memory also includes instructions for activating the aerosol generator. As illustrated, the controller connects to the aerosol generator with a cable (i.e., electric cable), although in some embodiments the controller may be wirelessly connected to the aerosol generator. The cable carries a signal that activates a piezoelectric (or other) actuator inside the aerosol generator. As the piezoelectric actuator operates, it vibrates a vibratable member that then aerosolizes the fluid for delivery to the patient (i.e., through inhalation). The memory may therefore include instructions for controlling when the piezoelectric actuator starts, stops, vibration frequency or frequencies, etc.

The aerosolization systems described herein may increase treatment effectiveness by timing the creation of the aerosol. For example, the aerosol delivery system may begin aerosolizing the medicament before the patient inhales. In this way, the aerosol delivery system takes advantage of the increased airflow at the start of inhalation. This increases the medicament delivery to the patient as the inhaled air carries the medicament farther into the patient's lungs. The aerosol delivery system may also aerosolize medicament as soon as inhalation is detected (e.g., for spontaneous breathing).

The aerosol delivery system coordinates delivery of the medicament using one or more breath sensors to determine when a patient inhales and for how long. These breath sensors may communicate with the controller through wired connections and/or wireless connections. In some embodiments, the aerosol delivery system may use a combination of breath sensors to provide redundancy and/or more accurate monitoring of the patient's breathing cycle. As just one example, the aerosol delivery system may use a flow sensor in combination with a radar sensor to monitor both airflow and chest movement. As another example, the aerosol delivery system may use a flow sensor, a radar sensor, and plethysmography sensor to monitor the breathing cycle. It will be appreciated that any number and/or any combination of breath sensors may be utilized in a given application to monitor the patient's breathing cycle.

In some embodiments, the flow sensor couples to a gas delivery conduit to sense changes in airflow during inhalation (e.g., mandatory, assisted, or spontaneous breathing). In some embodiments, the flow sensor may also couple to a gas return conduit to detect the start and end of exhalation. And in still other embodiments, the aerosol delivery system may include flow sensors that couple to the gas delivery conduit and the gas return conduit. As the controller receives data from the flow sensor(s), the controller may monitor breathing patterns to predict when the patient is going to breath. The ability to predict when inhalation begins enables the aerosol delivery system to prepare aerosolized medicament for immediate inhalation. More specifically, the aerosol delivery system is able to preload fluid on a vibratable member in the aerosol generator so that the fluid can be aerosolized before inhalation. Because flow detection is not a lagging indicator, the flow sensor can rapidly detect unusual or spontaneous inhalation for aerosol delivery (e.g., less than 10 milliseconds from the start of inhalation).

Predicting the patient's inhalation may begin by using one or more breath and/or flow sensors to tracking the patient's breathing pattern and/or a ventilation cycle (if a patient is mandatorily ventilated). The controller then uses the tracked data to predict when subsequent inhalations will begin. This allows the controller to direct the pump to deliver fluid from the fluid source to the aerosol generator prior to an inhalation. The controller may also signal the aerosol generator to begin aerosolizing the fluid at a proper time, such as within a predetermined time period (e.g., +/−0.5 seconds) before and/or during the predicted inhalation. In this way, aerosol is ready for the patient at the start of inhalation. While the aerosol delivery system is able to predict the breath cycle to produce aerosol for the patient, the aerosol delivery system is also able to recognize spontaneous/irregular breathing not part of the normal pattern using the breath sensors. Once a spontaneous breath is recognized, the aerosol delivery system may immediately pump fluid to the aerosol generator for delivery to the patient.

Example 1

A two part trial was conducted to determine safety and tolerability of dose of inhaled surfactant in preterm infants at risk for worsening RDS, while receiving nCPAP. Part I (10 infants) involved treating patients with a single dose and Part II involved multiple doses. 31 preterm infants in total who required nCPAP (machine CPAP) were enrolled into the study. Infants were initially stabilized on nCPAP/nIMV, by adjusting CPAP and FiO2 as needed to maintain clinical blood gases (CBGs) and oxygen saturation (SpO2) per clinical guidelines. Once the infant had been stabilized, AeroFact™, a bovine lung surfactant, was administered by nCPAP within two hours after birth.

The AeroFact™ dosing strategy was to administer a single aerosol dose to the infant, which was equivalent to an instilled dose of 108 mg/kg (allowing for 50% delivery efficiency from a nominal dose of 216 mg/kg). Oxygenation and ventilation parameters were monitored as outlined in the protocol until an effect was observed (as defined by protocol). Infants continued to be on nCPAP after the dose was administered. Clinical observation, indices of respiratory support, and co-morbidities of prematurity of the infants were monitored until the time of discharge from Neonatal Intensive Care Unit (NICU).

After successful completion of Part I and recommendation by an Independent Data Safety Monitoring Board (DSMB), sites were permitted to begin enrollment into Part II of the study.

Part II of the study was conducted in a separate group of preterm infants, also on nCPAP and at risk for worsening RDS.

An initial nominal dose of 216 mg/kg of aerosolized SF-RI 1 was administered. Oxygenation and ventilation parameters were monitored as outlined in the protocol and aerosol delivery was stopped at the time of completion of the intended dose.

Infants were to continue nCPAP. Re-dosing of AeroFact™ (nominal dose of 216 mg/kg) occurred if the Respiratory Severity Score (RSS; mean airway pressure×fraction of inspired oxygen) to maintain SpO2 between 90% and 95% (as measured by pulse oximetry)≥2.0 and at least (1) 2 hours elapsed since the end of the first dose and (2) 4 hours elapsed since the end of either the second or third dose. Up to 3 additional doses of AeroFact™ within 96 hours were allowed.

Ten (10) patients were enrolled in Part I and 21 patients were enrolled in Part II of the study and comprised both the ITT and the Safety Populations. The historical controls groups had 30 and 63 patients for Part I and Part II, respectively.

Per the protocol, all 10 patients (100%) in Part I received 1 dose of the study drug. In Part II, 13 patients (61.9%) received 1 dose of study drug, 4 patients (19%) received 2 doses of study drug, 4 patients (19%) received 3 doses of study drug, and there were no patients who received 4 doses of study drug.

The incidence of AeroFact™ patients who experienced 1 or more AE(s) was 7 (70%) in Part I and 13 (61.9%) in Part II. There were no AEs which were assessed by the Investigator as related to the study drug, device, or procedure, and there were no AEs which led to premature discontinuation from the study drug or of the patient from the study.

Generally, the incidence of AEs associated with dosing tolerance in the first 24 hours were low.

The number of patients with any co-morbidity of prematurity was 6 (60%) in Part I of the study compared with 20 (66.7%) in Part I historical controls, and 12 (57.14%) in Part II of the study compared with 31 (49.21%) in historical controls. Generally, the incidence of post-dose co-morbidities of prematurity and AEs was low and consistent between the patients treated with AeroFact™ and historical controls.

Conclusion

Administration of AeroFact™, up to 4 doses within 96 hours of life, was shown to be safe and well tolerated in patients ranging from 26²⁄₇ weeks to 30⁴⁄₇ weeks of gestational age and with weights between 640 to 1,664 grams.

The need for rescue therapy by instilled bolus surfactant was lower in Part II of the study compared with matching historical controls; 5 AeroFact™ patients (25%) in Part II required rescue with surfactant bolus instillations vs. 27 patients (45%) who required instillations in the matching historical control group as illustrated in the chart shown in FIG. 25; this corresponded to a relative risk of 0.56, in favor of AeroFact™ treatment.

Based on this study, it was concluded that the incidence of post-dose comorbidities of prematurity and adverse events (AE) was low and consistent between the patients treated using the aerosolization system of FIG. 17 vs. the historical controls. There were no treatment emergent adverse effects (TEAE) which were assessed as being related to the study drug, device, or procedure. During Day 1 to Day 4 of the study, following the dosing protocol, there was 1 occurrence of moderate nasal congestion in Part 1, with 5 occurrences of moderate nasal congestion and 1 occurrence of severe nasal congestion in Part 2. One patient in Part 1 and one patient in Part 2 had fatal serious adverse events (SAE) (culture-proven sepsis), which were not related to the study drug, the device, or the procedure and did not emerge during the treatment period. Generally, the incidence of AEs associated with dosing tolerance within the first 24 hours was low. The incidence of AEs for dosing using the aerosolization system of FIG. 17 only vs. dosing using the aerosolization system with a bolus surfactant demonstrated comparability.

Example 2

An active test lung was driven by a ventilator to provide a way to trigger an AF2b device respiration sensor (similar to that shown in FIG. 16) as well as simulate the breathing pattern of an infant. A mechanical ventilator (Pulmonetic Systems) was used to drive a Training/Test Lung (Michigan Instruments, Inc.). The training/test lung was driven on the adult side with a test lung balloon attached to the air circuit using a T-piece, to provide representation of the subtle abdominal movement of a neonate during respiration. The AF2b respiration sensor (which would normally be attached to the infant) was attached to the lung balloon. The small deflections of the balloon during inspiration/expiration cycles triggers the sensor for breath actuation of the device. The adult training/test lung was mechanically coupled to the infant training/test lung, which was then used to simulate the actual respiration of an infant. By adjusting the ventilator settings, different infant breath patterns can be simulated. A gas flow analyzer (IMT Analytics) was used to confirm the infant respiration parameters. Table 1 outlines the parameters of the Active Lung/Ventilator Test.

TABLE 1

Active Lung/Ventilator Test Settings.

| Breath Setting | Tidal Volume (mL) | Respiratory Rate (BPM) | I:E Ratio |
|---|---|---|---|
| Low | 10 | 40 | 1:2.5 |
| Medium | 8 | 60 | 1:2.0 |
| High | 5 | 80 | 1:1.0 |

Aerodynamic Particle Sizing by Next Generation Impactor

Next Generation Impactor (NGI) testing was performed per USP<1601>, using an NGI chilled in a refrigerator at 4-8° C. for >90 mins before used and sampled at a flowrate of 15 L/min. Each NGI run was performed with approximately 0.5 mL of AlveoFact™ formulation. During testing, the NGI was kept in a cooling chamber (maintained at 5° C.) while drawing in ambient air with the AF2b device outside the cooling chamber. The nebulizer as described in accordance with FIGS. 6-6D (without nasal prongs) was attached to the NGI induction port using a T-piece with an adaptor. Inspiratory and expiratory limbs were left open while the open end of the T-piece was blocked off. NGI samples were assayed gravimetrically per AS00006.

Study Outline

TABLE 2

Test Outline

| Nebulizer S/N | Breath Setting | NGI [N] |
|---|---|---|
| 189970-0071 | Low | 1 |
| | Medium | 1 |
| | High | 1 |
| 189970-0087 | Low | 1 |
| | Medium | 1 |
| | High | 1 |
| 189972-0046 | Low | 1 |
| | Medium | 1 |
| | High | 1 |

Results

Results showed comparable aerodynamic particle size for all ventilator settings tested (low, medium, and high) for all three nebulizers tested. Mean MMAD and GSD (three nebulizers) for low, medium and high settings are 2.3 μm and 1.5, respectively, as shown in Table 3 below.

TABLE 3

Summary Table of Results.

| Device ID | CPAP Setting | MMAD (μm) | GSD | FPD54-MOC (mg) | FPDS5-MOC (mg) | Recovery (% Nominal) | FPF < 3.3 μm (% NGI recovery) | FPF < 5.4 μm (% NGI Recovery) |
|---|---|---|---|---|---|---|---|---|
| 189972-0046 | Low | 2.0 | 1.5 | 13.5 | 12.3 | 54.6 | 89 | 97 |
| | Medium | 2.1 | 1.6 | 13.0 | 11.6 | 52.0 | 88 | 98 |
| | High | 2.2 | 1.5 | 14.6 | 12.9 | 59.0 | 86 | 97 |
| 189970-0087 | Low | 2.5 | 1.5 | 14.5 | 11.5 | 59.1 | 76 | 96 |
| | Medium | 2.4 | 1.5 | 13.7 | 11.3 | 56.3 | 79 | 95 |
| | High | 2.4 | 1.5 | 14.2 | 11.6 | 57.5 | 79 | 97 |
| 189970-0071 | Low | 2.3 | 1.5 | 13.2 | 11.2 | 53.2 | 83 | 97 |
| | Medium | 2.4 | 1.5 | 14.0 | 11.8 | 58.1 | 80 | 95 |
| | High | 2.2 | 1.5 | 14.0 | 12.0 | 56.6 | 83 | 97 |
| Overall Mean, Low | | 2.3 | 1.5 | 13.7 | 11.7 | 55.6 | 83 | 97 |
| Overall Mean, Medium | | 2.3 | 1.5 | 13.6 | 11.6 | 55.5 | 82 | 96 |
| Overall Mean, High | | 2.3 | 1.5 | 14.3 | 12.2 | 57.7 | 83 | 97 |

TABLE 3-continued

Summary Table of Results.

| Device ID | CPAP Setting | MMAD (μm) | GSD | FPD54-MOC (mg) | FPDS5-MOC (mg) | Recovery (% Nominal) | FPF < 3.3 μm (% NGI recovery) | FPF < 5.4 μm (% NGI Recovery) |
|---|---|---|---|---|---|---|---|---|
| SD, Low | | 0.23 | 0.01 | 0.66 | 0.58 | 3.06 | 6 | 1 |
| SD, Medium | | 0.18 | 0.03 | 0.55 | 0.27 | 3.14 | 5 | 2 |
| SD, High | | 0.14 | 1.03 | 0.31 | 0.68 | 1.23 | 3 | 0 |

Figure 26:
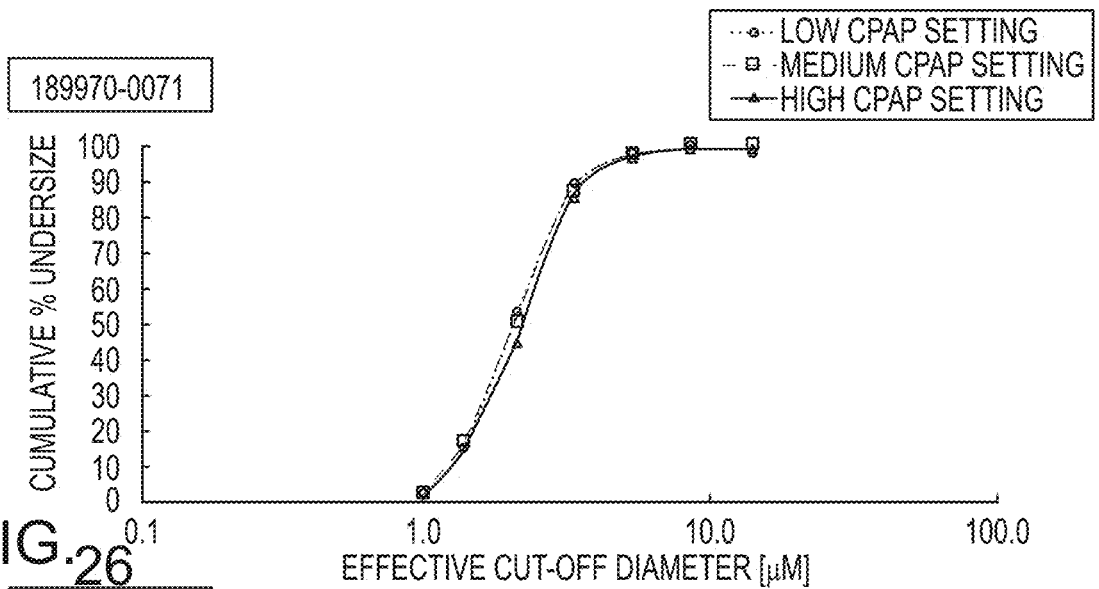
FIG. 26 is a graph showing impactor particle size distributions according to a study.
Figure 27:
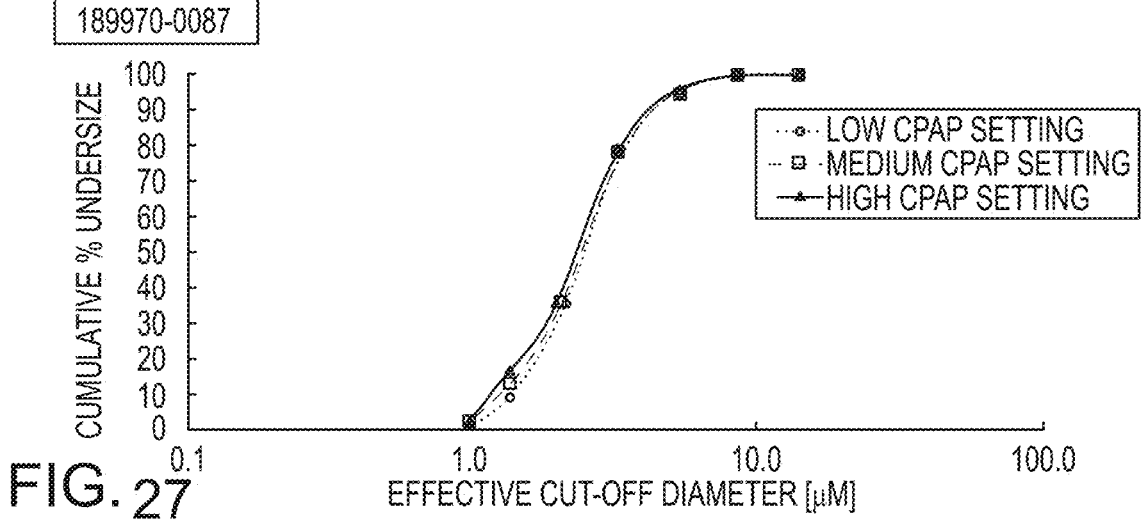
FIG. 27 is a graph showing impactor particle size distributions according to a study.
Figure 28:
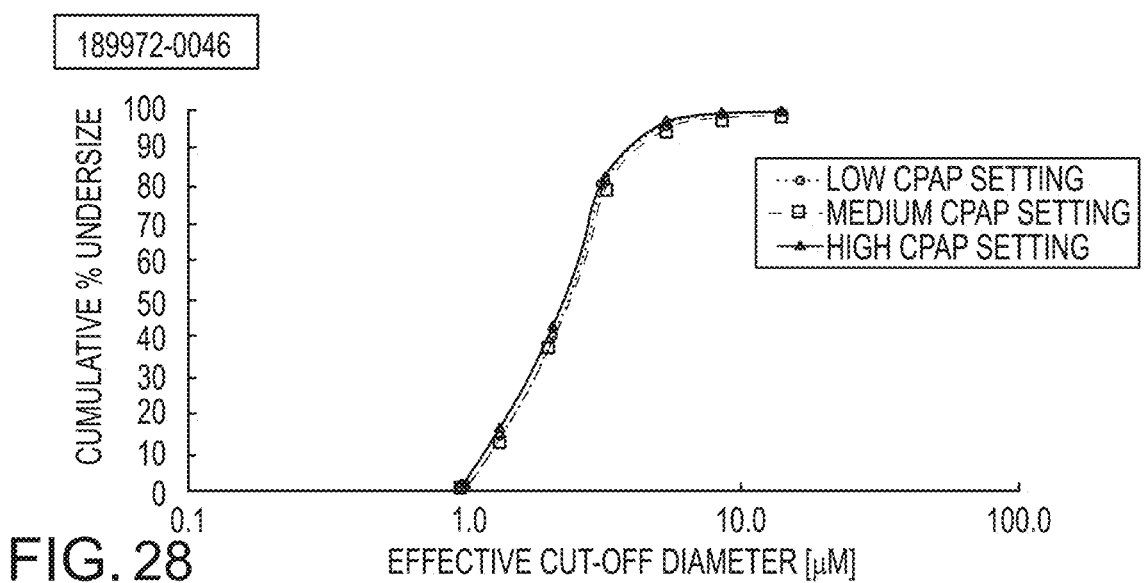
FIG. 28 is a graph showing impactor particle size distributions according to a study.

The results further demonstrate that the aerodynamic particle size distribution were comparable regardless of ventilator setting for each of the tested nebulizers as shown in FIGS. 26-28, which show consistent results across each CPAP setting (low, medium, high).

Figure 29:
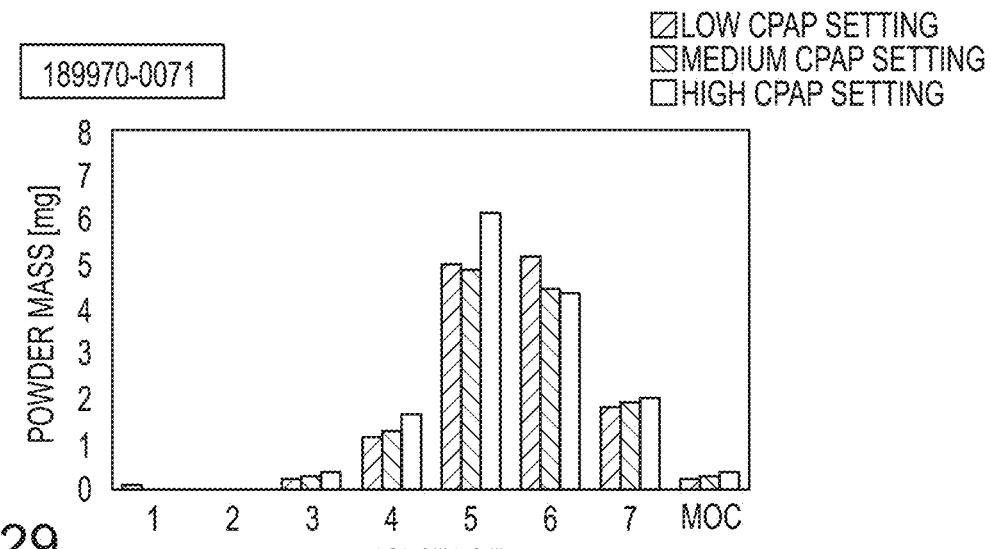
FIG. 29 is a graph showing powder mass distribution across different CPAP settings according to a study.
Figure 30:
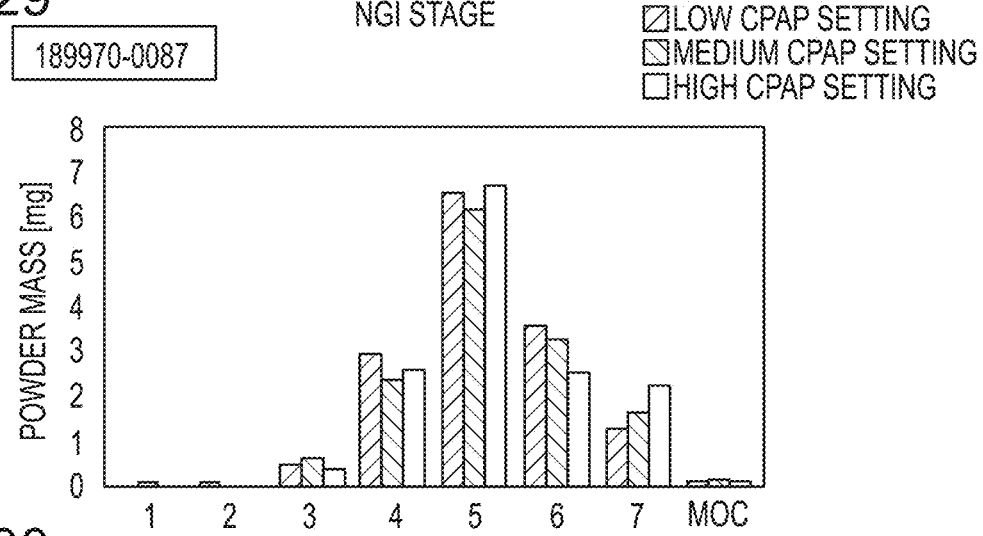
FIG. 30 is a graph showing powder mass distribution across different CPAP settings according to a study.
Figure 31:
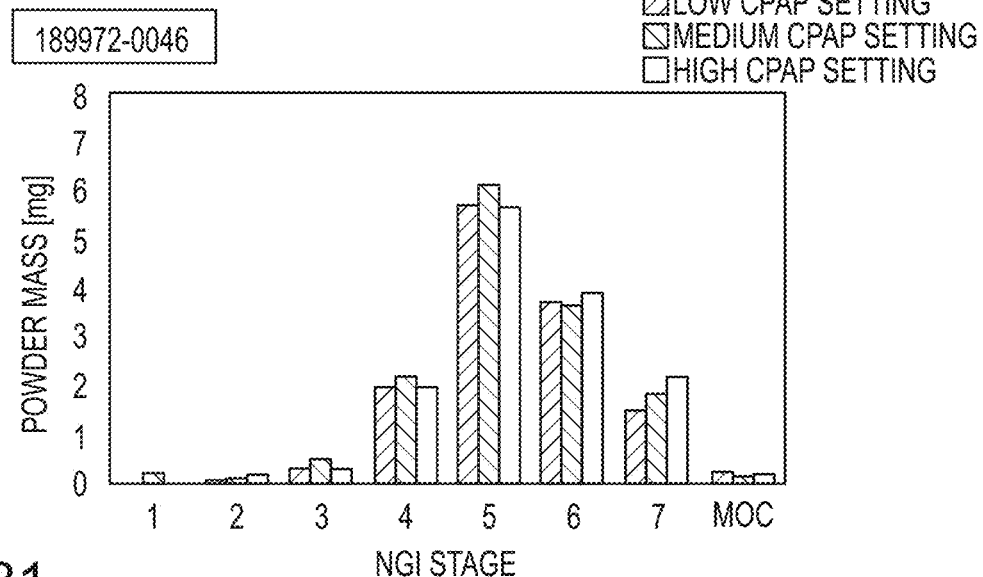
FIG. 31 is a graph showing powder mass distribution across different CPAP settings according to a study.

Additionally, stage by stage NGI mass values are shown in Tables 4-6 and in FIGS. 29-31. The stage cut-off diameters indicate the maximum size of particle that can pass through each stage of the NGI, with masses of particles passing through each stage at each CPAP setting.

TABLE 4

Summary of NGI Stage Masses for Nebulizer 189972-0046.

| Stage | Stage Cut-Off Diameter Undersize (μm) | Low Mass (mg) | Medium Mass (mg) | High Mass (mg) |
|---|---|---|---|---|
| 1 | 14.1 | 0.13 | 0.00 | 0.00 |
| 2 | 8.61 | 0.00 | 0.00 | 0.05 |
| 3 | 5.39 | 0.26 | 0.31 | 0.40 |
| 4 | 3.30 | 1.19 | 1.32 | 1.68 |
| 5 | 2.08 | 4.99 | 4.91 | 6.14 |
| 6 | 1.36 | 5.21 | 4.45 | 4.39 |
| 7 | 0.98 | 1.86 | 1.95 | 2.05 |
| MOC | <0.98 | 0.28 | 0.32 | 0.34 |

TABLE 5

Summary of NGI Stage Masses for Nebulizer 189970-0087.

| Stage | Stage Cut-Off Diameter Undersize (μm) | Low Mass (mg) | Medium Mass (mg) | High Mass (mg) |
|---|---|---|---|---|
| 1 | 14.1 | 0.00 | 0.06 | 0.00 |
| 2 | 8.61 | 0.08 | 0.00 | 0.00 |
| 3 | 5.39 | 0.52 | 0.64 | 0.44 |
| 4 | 3.30 | 2.98 | 2.37 | 2.63 |
| 5 | 2.08 | 6.54 | 6.17 | 6.68 |
| 6 | 1.36 | 3.61 | 3.29 | 2.53 |
| 7 | 0.98 | 1.27 | 1.64 | 2.24 |
| MOC | <0.98 | 0.06 | 0.19 | 0.14 |

TABLE 6

Summary of NGI Stage Masses for Nebulizer 189970-0071.

| Stage | Stage Cut-Off Diameter Undersize (μm) | Low Mass (mg) | Medium Mass (mg) | High Mass (mg) |
|---|---|---|---|---|
| 1 | 14.1 | 0.00 | 0.19 | 0.02 |
| 2 | 8.61 | 0.07 | 0.08 | 0.16 |
| 3 | 5.39 | 0.32 | 0.51 | 0.27 |
| 4 | 3.30 | 1.95 | 2.22 | 1.97 |
| 5 | 2.08 | 5.75 | 6.18 | 5.74 |
| 6 | 1.36 | 3.74 | 3.66 | 3.92 |
| 7 | 0.98 | 1.54 | 1.87 | 2.17 |
| MOC | <0.98 | 0.20 | 0.11 | 0.18 |

Conclusions

Based on the results, the aerodynamic particle size of AlveoFact® generated from the AF2b PDAP' device was shown to be independent of simulated spontaneous breath setting. Specifically, regardless of the CPAP setting, the aerosol particles were less than 3 μm, more specifically in the range of between 2.0 and 2.5 μm, with very small geometric standard deviation (GSD) of 1.5-1.6. The Fine Particle Fraction of particles less than 3.3 μm across all CPAP settings was approximately 83%. The study further illustrated that across the range of CPAP settings, consistent particle delivery is provided.

Additionally, stage by stage NGI mass values are shown in Tables 4-6 and in FIGS. 29-31. This data demonstrates that for each impactor stage, the powder masses were consistent across the various CPAP settings.

Testing has also demonstrated that the aerosol droplet size was consistent throughout delivery of a full dose at a CPAP flow of 6 LPM at 50 psi. The test settings are depicted in Table 7 below.

TABLE 7

DIR90-178/152 - Aerosol Droplet Size (medium nasal prongs)

| | | Active Lung/Ventilation settings | | | Bubble CPAP settings | | | Aerosol |
|---|---|---|---|---|---|---|---|---|
| Dosing Time | CPAP Setting | Respiratory Rate [BPM] | Tidal Vol [mL] | I:E Ratio | CPAP Flow at 50 psi | PEEP [cm H₂0] | Humidifier settings | Test NGI (N) |
| Beginning | Mid | 60 | 8 | 1:2 | 6 LPM | 5 | 37 ± 2° C. | 3 |
| End | Mid | 60 | 8 | 1:2 | 6 LPM | 5 | 37 ± 2° C. | 3 |

Table 8 below demonstrates that the MMAD produced by each aerosolization device was very consistent from the beginning of a dose to the end of a maximum dose (4 vials of 108 mg), with MMADs under 3.0 µm (between 2.5 to 3.0 µm) for each aerosolization device, with GSD of between 1.4 and 1.5. This showed that the usage of the mesh did not result in an enlargement of the pores of the mesh, thereby ensuring that the PDAP mesh was viable to generate aerosolized particles with an MMAD of less that about 3.0 µm for a lifespan that covers the maximum allowed doses of surfactant.

TABLE 8

NGI Results for DIR90-178/152 Aerosol Droplet Size

| Device ID | Dose Time | MMAD (µm) | GSD |
|---|---|---|---|
| 189966-0013 | Beginning | 2.7 | 1.5 |
|  | End | 2.6 | 1.4 |
| 189966-0060 | Beginning | 2.6 | 1.4 |
|  | End | 2.6 | 1.5 |
| 189962-0052 | Beginning | 3.0 | 1.5 |
|  | End | 2.5 | 1.4 |

Table 9 indicates the test parameters for testing for inhaled dose efficiency with nasal prong diameters of different sizes.

TABLE 9

DIR90-178/004 - Nasal Prong Adapters

| Nasal Prong Size | CPAP Setting | Active Lung/Ventilation settings | | | Bubble CPAP settings | | | Aerosol Test Delivered Dose (N) |
|---|---|---|---|---|---|---|---|---|
| | | Respiratory Rate [BPM] | Tidal Vol [mL] | I:E Ratio | Bubble CPAP Flow at 50 psi | PEEP [cm H$_2$O] | Humidifier settings | |
| BC3520 (Small) | High | 80 | 5 | 1:1 | 6 LPM | 8 | 37 ± 2° C. | 3 |
| BC4030 (Medium) | High | 80 | 5 | 1:1 | 6 LPM | 8 | 37 ± 2° C. | 3 |
| BC4540 (Large) | High | 80 | 5 | 1:1 | 6 LPM | 8 | 37 ± 2° C. | 3 |

As shown in the results of Table 10 below, the delivered dose for the various sized nasal prongs was consistent, between 42%-57% (which substantially exceeds the delivered dose of conventional devices of approximately 6%. Results show a mean DD of 51, 45 and 50% for the small, medium and large prongs respectively. This demonstrates that there is no significant effect on DD due to prong size.

TABLE 10

Delivered Dose Results for DIR90-178/004 Nasal Prong Adapters Testing

| Nasal Prong Size | Device ID | DD (mg) | Mean DD (mg) | SD (mg) | RSD (%) | DD (%)[1] | Mean DD (%)[1] | SD (%)[1] |
|---|---|---|---|---|---|---|---|---|
| BC3520 (Small) | 189966-0103 | 14.53 | 13.1 | 1.3 | 10 | 57 | 51 | 5 |
|  | 189962-0034 | 12.66 | | | | 50 | | |
|  | 189962-0060 | 12.04 | | | | 47 | | |
| BC4030 (Medium) | 189966-0103 | 13.48 | 11.5 | 1.8 | 15 | 53 | 45 | 7 |
|  | 189962-0034 | 10.13 | | | | 40 | | |
|  | 189962-0060 | 10.81 | | | | 42 | | |
| BC4540 (Large) | 189966-0103 | 14.65 | 12.9 | 1.6 | 12 | 57 | 50 | 6 |
|  | 189962-0034 | 11.63 | | | | 46 | | |
|  | 189962-0060 | 12.31 | | | | 48 | | |

[1]calculated

Table 11 provides test settings for determining the effectiveness of the aerosolization device to deliver aerosolized doses in various orientations. The aerosolization device was tested at 0° (infant on its back), 90° (infant on its side), and 180° (infant on its stomach), with delivered doses being measured at each orientation.

TABLE 11

DIR90-178/002 - Orientation (medium nasal prongs)

| Orientation | Active Lung/Ventilation settings | | | | Bubble CPAP settings | | | Aerosol Test |
|---|---|---|---|---|---|---|---|---|
| | CPAP Setting | Respiratory Rate [BPM] | Tidal Vol [mL] | I:E Ratio | Bubble CPAP Flow at 50 psi | PEEP [cm $H_2O$] | Humidifier settings | Delivered Dose (N) |
| 0° | Mid | 60 | 8 | 1:2 | 6 LPM | 5 | 37 ± 2° C. | 3 |
| ±90° | Mid | 60 | 8 | 1:2 | 6 LPM | 5 | 37 ± 2° C. | 3 |
| 180° | Mid | 60 | 8 | 1:2 | 6 LPM | 5 | 37 ± 2° C. | 3 |

Table 12 provides the results of the orientation testing. Results show that there was no orientation effect on DD for both dosing positions, 0° (supine) and 90° (laying on side) with a mean of 69% and 70% respectively. At the 180° (face down) position the AF2b device was able to maintain breath actuated aerosolization for the entire 0.5 mL dose for all three devices with a mean DD was 46%. Both results demonstrate that the system reliably generated aerosol in all orientations tested.

TABLE 12

Delivered Dose Results for DIR90-178/002 Orientation Testing

| Orientation | Device ID | DD (mg) | Mean DD (mg) | SD (mg) | RSD (%) | DD (%)[1] | Mean DD (%)[1] | SD (%)[1] |
|---|---|---|---|---|---|---|---|---|
| 0° | 189962-0039 | 18.36 | 17.6 | 0.8 | 4 | 72 | 69 | 3 |
| | 189966-0014 | 17.71 | | | | 69 | | |
| | 189966-0105 | 16.86 | | | | 66 | | |
| 90° | 189962-0039 | 19.13 | 17.8 | 1.2 | 7 | 75 | 70 | 5 |
| | 189966-0014 | 17.66 | | | | 69 | | |
| | 189966-0105 | 16.71 | | | | 66 | | |
| 180° | 189962-0039 | 11.14 | 11.8 | 0.7 | 6 | 44 | 46 | 3 |
| | 189966-0014 | 12.47 | | | | 49 | | |
| | 189966-0105 | 11.80 | | | | 46 | | |

[1]% calculated based on a nominal 0.5 mL dose of SF-RI 1 (empirically determined to contain 25.5 mg dried content of SF-RI 1).

The methods, systems, and devices discussed above are examples. Some embodiments were described as processes depicted as flow diagrams or block diagrams. Although each may describe the operations as a sequential process, many of the operations can be performed in parallel or concurrently. In addition, the order of the operations may be rearranged. A process may have additional steps not included in the figure. Furthermore, embodiments of the methods may be implemented by hardware, software, firmware, middleware, microcode, hardware description languages, or any combination thereof. When implemented in software, firmware, middleware, or microcode, the program code or code segments to perform the associated tasks may be stored in a computer-readable medium such as a storage medium. Processors may perform the associated tasks.

It should be noted that the systems and devices discussed above are intended merely to be examples. It must be stressed that various embodiments may omit, substitute, or add various procedures or components as appropriate. Also, features described with respect to certain embodiments may be combined in various other embodiments. Different aspects and elements of the embodiments may be combined in a similar manner. Also, it should be emphasized that technology evolves and, thus, many of the elements are examples and should not be interpreted to limit the scope of the invention.

Specific details are given in the description to provide a thorough understanding of the embodiments. However, it will be understood by one of ordinary skill in the art that the embodiments may be practiced without these specific details. For example, well-known structures and techniques have been shown without unnecessary detail in order to avoid obscuring the embodiments. This description provides example embodiments only, and is not intended to limit the scope, applicability, or configuration of the invention. Rather, the preceding description of the embodiments will provide those skilled in the art with an enabling description for implementing embodiments of the invention. Various changes may be made in the function and arrangement of elements without departing from the spirit and scope of the invention.

The methods, systems, devices, graphs, and tables discussed above are examples. Various configurations may omit, substitute, or add various procedures or components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims. Additionally, the techniques discussed herein may provide differing results with different types of context awareness classifiers.

While illustrative and presently preferred embodiments of the disclosed systems, methods, and machine-readable media have been described in detail herein, it is to be understood that the inventive concepts may be otherwise variously embodied and employed, and that the appended claims are intended to be construed to include such variations, except as limited by the prior art.

Unless defined otherwise, all technical and scientific terms used herein have the same meaning as commonly or conventionally understood. As used herein, the articles "a" and "an" refer to one or to more than one (i.e., to at least one) of the grammatical object of the article. By way of example, "an element" means one element or more than one element. "About" and/or "approximately" as used herein when referring to a measurable value such as an amount, a temporal duration, and the like, encompasses variations of ±20% or ±10%, ±5%, or +0.1% from the specified value, as such variations are appropriate to in the context of the systems, devices, circuits, methods, and other implementations described herein. "Substantially" as used herein when referring to a measurable value such as an amount, a temporal duration, a physical attribute (such as frequency), and the like, also encompasses variations of ±20% or ±10%, ±5%, or +0.1% from the specified value, as such variations are appropriate to in the context of the systems, devices, circuits, methods, and other implementations described herein. As used herein, including in the claims, "and" as used in a list of items prefaced by "at least one of" or "one or more of" indicates that any combination of the listed items may be used. For example, a list of "at least one of A, B, and C" includes any of the combinations A or B or C or AB or AC or BC and/or ABC (i.e., A and B and C). Furthermore, to the extent more than one occurrence or use of the items A, B, or C is possible, multiple uses of A, B, and/or C may form part of the contemplated combinations. For example, a list of "at least one of A, B, and C" may also include AA, AAB, AAA, BB, etc.

Having described several embodiments, it will be recognized by those of skill in the art that various modifications, alternative constructions, and equivalents may be used without departing from the spirit of the invention. For example, the above elements may merely be a component of a larger system, wherein other rules may take precedence over or otherwise modify the application of the invention. Also, a number of steps may be undertaken before, during, or after the above elements are considered. Accordingly, the above description should not be taken as limiting the scope of the invention.

Also, the words "comprise", "comprising", "contains", "containing", "include", "including", and "includes", when used in this specification and in the following claims, are intended to specify the presence of stated features, integers, components, or steps, but they do not preclude the presence or addition of one or more other features, integers, components, steps, acts, or groups.

What is claimed:

1. An aerosolization system, comprising:
a respiration system comprising an inspiratory limb and an expiratory limb;
an aerosolization device, comprising:
an aerosol chamber having a first end and a second end;
an aerosol generator positioned at the first end of the aerosol chamber, the aerosol generator comprises a vibratable mesh, wherein:
the aerosol generator comprises a reservoir that is configured to receive a volume of liquid medicament for aerosolization by the aerosol generator; and
the vibratable mesh of the aerosol generator is configured to aerosolize the volume of medicament into particles having a mass mean aerodynamic diameter (MMAD) of less than about 3 μm at a rate of at least 0.1 ml/min;
a patient interface that is positioned proximate the second end of the aerosol chamber; and
a respiratory adaptor that is configured to couple the aerosolization device with the respiration system, wherein:
the respiratory adaptor comprises a diversion mechanism that is configured to divert a portion of airflow from the respiration system into the aerosol chamber via at least one airway;
the at least one airway introduces the portion of airflow into the aerosol chamber proximate the first end and the aerosol generator; and
the aerosol chamber is configured to mix the portion of airflow with aerosolized medicament from the aerosol generator;
at least one breath sensor that is configured to detect an inhalation of a patient; and
a controller that is configured to actuate the aerosol generator to aerosolize the volume of medicament in synchronization with the detected inhalation.

2. The aerosolization system of claim 1, wherein:
the patient interface is positioned between about 1 cm and 8 cm from the aerosol generator.

3. The aerosolization system of claim 1, wherein:
the portion of airflow is respiratory flow and is less than an amount of air that continues to an expiratory limb of the respiration system.

4. The aerosolization system of claim 1, wherein:
the diversion mechanism comprises at least one baffle that defines the at least one airway; and
the at least one baffle is configured to divert the portion of airflow into the aerosol chamber via the at least one airway and to divert an additional portion of airflow from the inspiratory limb to the expiratory limb.

5. The aerosolization system of claim 4, wherein:
the at least one baffle comprises a first baffle that defines a first airway and a second baffle that defines a second airway.

6. The aerosolization system of claim 5, wherein:
the first airway is provided at a lateral end of the first baffle;
the second airway is provided beyond a distal edge of the second baffle; and
the lateral end and the distal edge extend in different directions such that the respiratory flow moves in multiple directions to pass the first baffle and the second baffle.

7. The aerosolization system of claim 1, wherein:
the aerosolization device further comprises a conduit that is configured to deliver the volume of liquid medicament from the reservoir to the aerosol generator.

8. The aerosolization system of claim 7, wherein:
a distalmost tip of the conduit has a diameter; and
the distalmost tip of the conduit is positioned at a distance from the vibratable mesh of the aerosol generator that is less than or equal to the diameter.

9. The aerosolization system of claim 1, wherein:
synchronization of the aerosolization of the volume of medicament comprises aerosolizing a portion of the volume of medicament within at least a portion of a first 50%-80% of each of a successive number of inhalations such that chase air is provided within at least a portion of a final 20% of each of the successive number of inhalations.

10. The aerosolization system of claim 1, wherein:
the at least one breath sensor comprises a respiration sensor capsule configured to be interfaced with the patient's abdomen.

11. The aerosolization system of claim 1, wherein:
the controller is removable from the aerosolization device.

12. The aerosolization system of claim 1, wherein:
the aerosolization device is configured to aerosolize and deliver aerosolized particles of the medicament while the patient interface is oriented in each of a downward position, a side-facing position, and an upward position.

13. The aerosolization system of claim 1, further comprising:
a feed line that is configured to supply the volume of the medicament from a source to the reservoir.

14. The aerosolization system of claim 1, wherein:
the patient interface comprises nasal prongs or a nasal mask.

15. The aerosolization system of claim 1, wherein:
the medicament comprises a surfactant.

16. A method of delivering aerosolized medicament to an infant, comprising:
diverting a portion of airflow from a respiration system into an aerosol chamber of an aerosolization device via at least one airway, wherein the at least one airway introduces the portion of airflow into the aerosol chamber proximate an aerosol generator of the aerosolization device;
detecting an inhalation of an infant using one or more breath sensors; and
aerosolizing, using a vibratable mesh of the aerosolization generator, a volume of medicament into particles having a mass mean aerodynamic diameter (MMAD) of less than about 3 μm at a rate of at least 0.1 ml/min based on the detected inhalation, wherein the medicament is aerosolized within about 1 to 8 cm from a patient interface; and
mixing the portion of airflow with the aerosolized medicament within the aerosol chamber.

17. The method of delivering aerosolized medicament to an infant of claim 16, wherein:
aerosolizing the volume of the medicament comprises:
delivering the volume of the medicament from a reservoir to a mesh of the aerosolization device; and
vibrating the mesh to aerosolize the volume of the medicament.

18. The method of delivering aerosolized medicament to an infant of claim 17, wherein:
the volume of the medicament is delivered from the reservoir to the mesh via a conduit having a distalmost tip with a diameter; and
the distalmost tip of the conduit is positioned at a distance from the mesh is less than or equal to the diameter.

19. The method of delivering aerosolized medicament to an infant of claim 16, wherein:
aerosolizing the volume of the medicament comprises aerosolizing a portion of the volume of the medicament within at least a portion of a first 80% of each of a successive number of inhalations such that chase air is provided within at least a portion of a final 20% of each of the successive number of inhalations.

20. The method of delivering aerosolized medicament to an infant of claim 16, wherein:
the one or more breath sensors comprise a respiration sensor capsule interfaced with the patient's abdomen.

21. The method of delivering aerosolized medicament to an infant of claim 16, further comprising:
coupling the aerosolization device with the respiration system.

22. The method of delivering aerosolized medicament to an infant of claim 16, wherein:
the portion of airflow is respiratory flow and is less than an amount of air that continues to an expiratory limb of the respiration system.

23. The method of delivering aerosolized medicament to an infant of claim 16, wherein:
the portion of airflow is diverted using at least one baffle that defines the at least one airway; and
the at least one baffle is configured to divert the portion of airflow into the aerosol chamber via the at least one airway and to divert an additional portion of airflow from an inspiratory limb to an expiratory limb.

24. The method of delivering aerosolized medicament to an infant of claim 23, wherein:
the at least one baffle comprises a first baffle that defines a first airway and a second baffle that defines a second airway.

25. The method of delivering aerosolized medicament to an infant of claim 24, wherein:
the first airway is provided at a lateral end of the first baffle;
the second airway is provided beyond a distal edge of the second baffle; and
the lateral end and the distal edge extend in different directions such that the airflow moves in multiple directions to pass the first baffle and the second baffle.

26. The method of delivering aerosolized medicament to an infant of claim 16, wherein:
the patient interface comprises nasal prongs or a nasal mask.

27. The method of delivering aerosolized medicament to an infant of claim 16, further comprising:
delivering the aerosolized medicament to the infant's airway via the patient interface.

28. A method of initializing an aerosolization system, comprising:
connecting an aerosolization device with a controller, a respiration sensor, a medication source, and a respiration system;
inputting a user's access credentials into the controller;
inputting information associated with a patient and dose information into the controller;
coupling the respiration sensor with the patient;
priming the aerosolization device;
interfacing a patient interface with the patient's airways;
diverting a portion of airflow from the respiration system into an aerosol chamber of the aerosolization device via at least one airway, wherein the at least one airway introduces the portion of airflow into the aerosol chamber proximate an aerosol generator of the aerosolization device;
aerosolizing, using a vibratable mesh of the aerosolization generator, a volume of medicament into particles having a mass mean aerodynamic diameter (MMAD) of less than about 3 μm at a rate of at least 0.1 ml/min; and mixing the portion of airflow with the aerosolized medicament within the aerosol chamber.

29. The method of initializing an aerosolization system of claim 28, further comprising:
performing a start-up sequence that cycles through a plurality of audio alarms, visual alarms, or both audio and visual alarms.

30. The method of initializing an aerosolization system of claim 28, wherein:
the access credentials include one or more of a user identifier, a password, a possession-based credential, and a biometric credential.

31. The method of initializing an aerosolization system of claim 28, wherein:
the respiration sensor is adhered to the patient's abdomen.

32. The method of initializing an aerosolization system of claim 28, further comprising:
confirming a detection of breath after coupling the respiration sensor with the patient.

33. The method of initializing an aerosolization system of claim 28, wherein:
the medication source comprises a vented vial access device (VVAD) that is coupled with a fluid supply line.

34. The method of initializing an aerosolization system of claim 28, wherein:
connecting the aerosolization device with the controller, the respiration sensor, the medication source, and the respiration system comprises coupling a fluid supply line between the medication source and the aerosolization device.

35. The method of initializing an aerosolization system of claim 28, wherein:
priming the aerosolization device comprises aerosolizing a portion of medicament prior to interfacing the patient interface with the patient's airways.

36. The method of initializing an aerosolization system of claim 28, further comprising:
coupling the patient interface to the aerosolization device.

37. The method of initializing an aerosolization system of claim 28, wherein:
the patient interface is secured to patient via one or both of at least one strap and a foam pad that is configured to rest against the patient's head.

38. The method of initializing an aerosolization system of claim 28, further comprising:
delivering a dose of the aerosolized medicament to the patient via the patient interface.

39. The method of initializing an aerosolization system of claim 38, further comprising:
confirming that a timing of the delivered dose is in sync with a detected inhalation.

* * * * *